US008143447B2

(12) United States Patent
Moore et al.

(10) Patent No.: US 8,143,447 B2
(45) Date of Patent: Mar. 27, 2012

(54) TREATMENT OF CANCER

(75) Inventors: Jerome Moore, Issaquah, WA (US);
Bruce Keyt, Hillsborough, CA (US);
John Burnier, Pacifica, CA (US); Barry M. Sherman, Hillsborough, CA (US);
Max Totrov, San Diego, CA (US);
Valeria S. Ossovskaya, San Francisco, CA (US)

(73) Assignee: BiPar Sciences, Inc., South San Francisco, CA (US)

( * ) Notice: Subject to any disclaimer, the term of this patent is extended or adjusted under 35 U.S.C. 154(b) by 317 days.

(21) Appl. No.: 11/850,626

(22) Filed: Sep. 5, 2007

(65) Prior Publication Data
US 2008/0103104 A1 May 1, 2008

Related U.S. Application Data

(60) Provisional application No. 60/842,474, filed on Sep. 5, 2006.

(51) Int. Cl.
*C07C 233/65* (2006.01)
*C07C 323/42* (2006.01)
*C07C 323/62* (2006.01)

(52) U.S. Cl. ........................................ 564/162; 562/431

(58) Field of Classification Search .................. 564/162; 562/431
See application file for complete search history.

(56) References Cited

U.S. PATENT DOCUMENTS

| | | | |
|---|---|---|---|
| 2,006,735 A | 7/1935 | Fischer et al. |
| 2,937,204 A | 5/1950 | Harris et al. |
| 2,669,583 A | 2/1954 | Clinton et al. |
| 3,161,564 A | 12/1964 | Morehouse |
| 3,228,833 A | 1/1966 | Crounse et al. |
| 4,604,463 A | 8/1986 | Miyasaka et al. |
| 4,923,885 A | 5/1990 | Hupe et al. |
| 5,032,617 A | 7/1991 | Lee et al. |
| 5,041,653 A | 8/1991 | Lee et al. |
| 5,162,532 A | 11/1992 | Comins et al. |
| 5,177,075 A | 1/1993 | Sato et al. |
| 5,191,082 A | 3/1993 | Comins et al. |
| 5,200,524 A | 4/1993 | Comins et al. |
| 5,215,738 A | 6/1993 | Lee et al. |
| 5,223,608 A | 6/1993 | Chou et al. |
| 5,232,735 A | 8/1993 | Kurtz et al. |
| 5,243,050 A | 9/1993 | Comins et al. |
| 5,247,089 A | 9/1993 | Comins et al. |
| 5,262,564 A | 11/1993 | Kun et al. |
| 5,283,352 A | 2/1994 | Bäckström et al. |
| 5,321,140 A | 6/1994 | Comins et al. |
| 5,420,319 A | 5/1995 | Okamoto et al. |
| 5,434,254 A | 7/1995 | Chou et al. |
| 5,464,871 A | 11/1995 | Kun et al. |
| 5,473,074 A | 12/1995 | Kun et al. |
| 5,482,833 A | 1/1996 | Pero et al. |
| 5,482,975 A | 1/1996 | Kun et al. |
| 5,484,951 A | 1/1996 | Kun et al. |
| 5,516,941 A | 5/1996 | Kun et al. |
| 5,519,053 A | 5/1996 | Kun et al. |
| 5,583,155 A | 12/1996 | Kun et al. |
| 5,631,038 A | 5/1997 | Kurtz et al. |
| 5,631,231 A | 5/1997 | Kurtz et al. |
| 5,631,232 A | 5/1997 | Kurtz et al. |
| 5,631,240 A | 5/1997 | Kurtz et al. |
| 5,631,252 A | 5/1997 | Kurtz et al. |
| 5,631,272 A | 5/1997 | Kurtz et al. |
| 5,631,292 A | 5/1997 | Kurtz et al. |
| 5,631,294 A | 5/1997 | Kurtz et al. |
| 5,631,295 A | 5/1997 | Kurtz et al. |
| 5,631,299 A | 5/1997 | Kurtz et al. |
| 5,633,282 A | 5/1997 | Collins et al. |
| 5,637,618 A | 6/1997 | Kurtz et al. |
| 5,639,788 A | 6/1997 | Kurtz et al. |
| 5,641,795 A | 6/1997 | Kurtz et al. |
| 5,641,799 A | 6/1997 | Kurtz et al. |
| 5,641,811 A | 6/1997 | Kurtz et al. |
| 5,641,812 A | 6/1997 | Kurtz et al. |
| 5,643,894 A | 7/1997 | Kurtz et al. |
| 5,643,941 A | 7/1997 | Kurtz et al. |
| 5,643,945 A | 7/1997 | Kurtz et al. |
| 5,643,955 A | 7/1997 | Kurtz et al. |
| 5,643,956 A | 7/1997 | Kurtz et al. |
| 5,646,122 A | 7/1997 | Kurtz et al. |
| 5,650,403 A | 7/1997 | Kurtz et al. |
| 5,652,260 A | 7/1997 | Kun et al. |
| 5,652,367 A | 7/1997 | Kun et al. |
| 5,654,311 A | 8/1997 | Kurtz et al. |
| 5,665,755 A | 9/1997 | Kurtz et al. |
| 5,670,518 A | 9/1997 | Kun et al. |
| 5,700,792 A | 12/1997 | Kurtz et al. |

(Continued)

FOREIGN PATENT DOCUMENTS

CN 1768732 A 5/2006

(Continued)

OTHER PUBLICATIONS

Lee et al, Tetrahedron Letters, 2001, 1167-1169.*
Astrazeneca International. Gefitinib (IRESSA™) Lung Cancer ISEL Trial shows no overall survival advantage in a highly refractory population. Press release, Dec. 17, 2004. Available at: http://www.astrazeneca.com/pressrelease/4245.aspx Last accessed Mar. 4, 2008.
Banker, et al. Ed. Modern Pharmaceutics. Third Edition, Marcel Dekker. New York. 1996:596.
Bigler, et al. Evaluation of tamoxifen in persistent or recurrent nonsquamous cell carcinoma of the cervix: a Gynecologic Oncology Group study. International Journal of Gynecological Cancer 2004;14(5):871-874.
Chen, et al. Potential for selective modulation of glutathione in cancer chemotherapy. Chem Biol Interact. 1998; 111-112:263-75.
Chustecka, Z. Adding Bevacizumab Not Beneficial in Pancreatic Cancer. 2007 Gastrointestinal Cancers Symposium. Presented Jan. 20, 2007.

(Continued)

*Primary Examiner* — Shailendra Kumar
(74) *Attorney, Agent, or Firm* — Morrison & Foerster LLP

(57) ABSTRACT

The present invention provides compositions of matter, kits and methods for their use in the treatment of cancer. In particular, the invention provides compositions and methods for treating cancer in a subject by inhibiting a poly-ADP-ribose polymerase, as well as providing formulations and modes of administering such compositions.

4 Claims, 5 Drawing Sheets

U.S. PATENT DOCUMENTS

| | | | |
|---|---|---|---|
| 5,703,053 A | 12/1997 | Kurtz et al. |
| 5,719,151 A | 2/1998 | Shall et al. |
| 5,734,056 A | 3/1998 | Burk et al. |
| 5,736,576 A | 4/1998 | Kun et al. |
| 5,753,674 A | 5/1998 | Kun et al. |
| 5,756,510 A | 5/1998 | Griffin et al. |
| 5,770,599 A | 6/1998 | Gibson |
| 5,783,599 A | 7/1998 | Kun et al. |
| 5,837,729 A | 11/1998 | Bourinbaiar |
| 5,866,608 A | 2/1999 | Kurtz et al. |
| 5,874,444 A | 2/1999 | West et al. |
| 5,877,185 A | 3/1999 | Kun et al. |
| 5,908,861 A | 6/1999 | Kun |
| 5,922,775 A | 7/1999 | Kun et al. |
| 5,959,133 A | 9/1999 | Ohnishi |
| 5,981,575 A | 11/1999 | Kuhajda et al. |
| 6,004,978 A | 12/1999 | Kun et al. |
| 6,008,250 A | 12/1999 | Kurtz et al. |
| 6,015,792 A | 1/2000 | Kurtz et al. |
| 6,015,827 A | 1/2000 | Griffin et al. |
| 6,017,958 A | 1/2000 | Kun et al. |
| 6,100,283 A | 8/2000 | Griffin et al. |
| 6,121,278 A | 9/2000 | Jackson et al. |
| 6,156,739 A | 12/2000 | Griffin et al. |
| 6,169,104 B1 | 1/2001 | Tusé et al. |
| 6,201,020 B1 | 3/2001 | Zhang et al. |
| 6,235,748 B1 | 5/2001 | Li et al. |
| 6,277,990 B1 | 8/2001 | Jagtap et al. |
| 6,303,629 B1 | 10/2001 | Kun |
| 6,310,082 B1 | 10/2001 | Griffin et al. |
| 6,316,455 B1 | 11/2001 | Griffin et al. |
| 6,316,495 B1 | 11/2001 | Kun et al. |
| 6,326,517 B1 | 12/2001 | Kume et al. |
| 6,380,193 B1 | 4/2002 | Li et al. |
| 6,387,902 B1 | 5/2002 | Zhang et al. |
| 6,395,749 B1 | 5/2002 | Li et al. |
| 6,407,079 B1 | 6/2002 | Müller et al. |
| 6,423,696 B1 | 7/2002 | Collins et al. |
| 6,426,415 B1 | 7/2002 | Jackson et al. |
| 6,448,271 B1 | 9/2002 | Lubisch et al. |
| 6,476,048 B1 | 11/2002 | Szabo et al. |
| 6,495,541 B1 | 12/2002 | Webber et al. |
| 6,514,983 B1 | 2/2003 | Li et al. |
| 6,531,491 B1 | 3/2003 | Kania et al. |
| 6,548,494 B1 | 4/2003 | Webber et al. |
| 6,653,316 B1 | 11/2003 | South et al. |
| 6,664,269 B2 | 12/2003 | Martin et al. |
| 6,677,333 B1 | 1/2004 | Seko et al. |
| 6,723,733 B2 | 4/2004 | Li et al. |
| 6,903,098 B1 | 6/2005 | Lubisch et al. |
| 6,924,284 B2 | 8/2005 | Beaton et al. |
| 6,989,388 B2 | 1/2006 | Pellicciari et al. |
| 7,179,484 B2 | 2/2007 | Singh |
| RE39,608 E | 5/2007 | Lubisch et al. |
| 7,405,227 B2 | 7/2008 | Kun et al. |
| 7,538,252 B2 | 5/2009 | Ossovskaya et al. |
| 2002/0028815 A1 | 3/2002 | Ator et al. |
| 2002/0142334 A1 | 10/2002 | Brown et al. |
| 2002/0156050 A1 | 10/2002 | Li et al. |
| 2002/0164633 A1 | 11/2002 | Szabo et al. |
| 2004/0034078 A1 | 2/2004 | Skalitzky et al. |
| 2004/0077667 A1 | 4/2004 | Matsuoka et al. |
| 2004/0198693 A1 | 10/2004 | DeNinno et al. |
| 2004/0248879 A1 | 12/2004 | Canan-Koch et al. |
| 2004/0249841 A1 | 12/2004 | Cameron et al. |
| 2005/0004038 A1 | 1/2005 | Lyon et al. |
| 2005/0020595 A1 | 1/2005 | Kalish et al. |
| 2005/0026933 A1 | 2/2005 | Greenberger et al. |
| 2005/0054631 A1 | 3/2005 | Jiang et al. |
| 2005/0059824 A1 | 3/2005 | Vaidyanathan et al. |
| 2005/0080096 A1 | 4/2005 | Ishida et al. |
| 2005/0113283 A1 | 5/2005 | Solow-Cordero et al. |
| 2005/0142621 A1 | 6/2005 | Thompson et al. |
| 2005/0171036 A1 | 8/2005 | Arakawa et al. |
| 2005/0171101 A1 | 8/2005 | Yamamoto et al. |
| 2005/0182040 A1* | 8/2005 | Imazaki et al. .......... 514/210.01 |
| 2005/0227919 A1 | 10/2005 | Ashworth et al. |
| 2005/0287120 A1 | 12/2005 | Fisher et al. |
| 2006/0063767 A1 | 3/2006 | Javaid et al. |
| 2006/0074073 A1 | 4/2006 | Steinfeldt et al. |
| 2006/0084650 A1 | 4/2006 | Doug et al. |
| 2006/0094676 A1 | 5/2006 | Lahav et al. |
| 2006/0100198 A1 | 5/2006 | Liu et al. |
| 2006/0204981 A1 | 9/2006 | Li et al. |
| 2006/0229289 A1 | 10/2006 | Zhu et al. |
| 2006/0229351 A1 | 10/2006 | Zhu et al. |
| 2007/0015814 A1 | 1/2007 | Kun et al. |
| 2007/0015837 A1 | 1/2007 | Kun et al. |
| 2007/0265324 A1 | 11/2007 | Wernet et al. |
| 2007/0281948 A1 | 12/2007 | Peukert et al. |
| 2007/0292883 A1 | 12/2007 | Ossovskaya et al. |
| 2008/0025990 A1 | 1/2008 | Ludwig |
| 2008/0039633 A1 | 2/2008 | Jung et al. |
| 2008/0076737 A1 | 3/2008 | Ossovskaya et al. |
| 2008/0076778 A1 | 3/2008 | Ossovskaya et al. |
| 2008/0103104 A1 | 5/2008 | Kun et al. |
| 2008/0103208 A1 | 5/2008 | Ossovskaya et al. |
| 2008/0167345 A1 | 7/2008 | Jones et al. |
| 2008/0171786 A1 | 7/2008 | Bruggemeier et al. |
| 2008/0176946 A1 | 7/2008 | Ossovskaya et al. |
| 2008/0262062 A1 | 10/2008 | Ossovskaya et al. |
| 2008/0293795 A1 | 11/2008 | Donawho et al. |
| 2008/0319054 A1 | 12/2008 | Kun et al. |
| 2009/0076122 A1 | 3/2009 | Kun et al. |
| 2009/0123419 A1 | 5/2009 | Sherman et al. |
| 2009/0131529 A1 | 5/2009 | Sherman et al. |
| 2009/0149397 A1 | 6/2009 | Ossovskaya et al. |
| 2009/0149417 A1 | 6/2009 | Ossovskaya et al. |
| 2009/0275608 A1 | 11/2009 | Ossovskaya et al. |
| 2009/0291924 A1 | 11/2009 | Ossovskaya et al. |
| 2010/0160442 A1 | 6/2010 | Ossovskaya et al. |

FOREIGN PATENT DOCUMENTS

| | | |
|---|---|---|
| CN | 1768733 | 5/2006 |
| CN | 1768733 A | 5/2006 |
| CN | 101190211 A | 6/2008 |
| DE | 10 2005 023 834 A1 | 5/2006 |
| EP | 0 841 924 B1 | 5/1998 |
| EP | 1 127 052 B1 | 8/2001 |
| EP | 1348432 A1 | 10/2003 |
| EP | 1 500 643 A1 | 1/2005 |
| EP | 1 082 416 B1 | 3/2007 |
| FR | 2456731 | 12/1980 |
| GB | 1 463 575 | 2/1977 |
| GB | 2 447 796 B | 3/2009 |
| JP | 6-345723 * | 12/1994 |
| JP | 2000191612 | 7/2000 |
| JP | 2005336083 | 12/2005 |
| WO | WO-91/18591 A1 | 12/1991 |
| WO | WO-94/05664 A1 | 3/1994 |
| WO | WO-94/10202 A1 | 5/1994 |
| WO | WO 94/26730 A2 | 11/1994 |
| WO | WO 94/27584 A1 | 12/1994 |
| WO | WO 94/26730 A3 | 1/1995 |
| WO | WO 94/27584 A3 | 5/1995 |
| WO | WO 96/22791 A1 | 8/1996 |
| WO | WO-96/40210 A1 | 12/1996 |
| WO | WO 97/34593 A1 | 9/1997 |
| WO | WO-92/06687 A1 | 10/1997 |
| WO | WO 98/45253 A1 | 10/1998 |
| WO | WO-98/51307 A1 | 11/1998 |
| WO | WO-99/11624 A1 | 3/1999 |
| WO | WO-99/11628 A1 | 3/1999 |
| WO | WO 01/04086 A1 | 1/2001 |
| WO | WO 02/49992 A2 | 6/2002 |
| WO | WO 02/049992 A3 | 9/2002 |
| WO | WO 03/007955 A2 | 1/2003 |
| WO | WO-2008/030891 A2 | 3/2003 |
| WO | WO-2008/030891 A3 | 3/2003 |
| WO | WO 03/007955 A3 | 5/2003 |
| WO | WO-03/062392 A2 | 7/2003 |
| WO | WO-03/062392 A3 | 7/2003 |
| WO | WO-2005/012305 A2 | 2/2005 |
| WO | WO-2005/012305 A3 | 2/2005 |
| WO | WO-2005/054201 A1 | 6/2005 |
| WO | WO-2005/054209 A1 | 6/2005 |
| WO | WO-2005/054210 A1 | 6/2005 |

| | | |
|---|---|---|
| WO | WO-2005/058843 A1 | 6/2005 |
| WO | WO-2005/058843 C1 | 6/2005 |
| WO | WO-2005/097750 A1 | 10/2005 |
| WO | WO-2006/003146 A1 | 1/2006 |
| WO | WO-2006/003147 A1 | 1/2006 |
| WO | WO-2006/003148 A1 | 1/2006 |
| WO | WO-2006/003150 A1 | 1/2006 |
| WO | WO-2006/020681 A2 | 2/2006 |
| WO | WO-2006/020681 A3 | 2/2006 |
| WO | WO-2006/033006 A2 | 3/2006 |
| WO | WO-2006/033006 A3 | 3/2006 |
| WO | WO-2006/046735 A1 | 5/2006 |
| WO | WO-2006/067472 A1 | 6/2006 |
| WO | WO 2007/011962 A2 | 1/2007 |
| WO | WO-2007/107305 A2 | 9/2007 |
| WO | WO-2007/107305 A3 | 9/2007 |
| WO | WO 2007/011962 A3 | 12/2007 |
| WO | WO 2008/030883 A2 | 3/2008 |
| WO | WO-2008/089272 A1 | 7/2008 |
| WO | WO-2008/107478 A1 | 9/2008 |
| WO | WO-2008/147418 A1 | 12/2008 |
| WO | WO-2009/064444 A2 | 5/2009 |
| WO | WO-2009/064738 A2 | 5/2009 |
| WO | WO-2009/073869 A1 | 6/2009 |
| WO | WO-2009/100159 A2 | 8/2009 |
| WO | WO-2009/100159 A3 | 8/2009 |
| WO | WO-2010/091140 A1 | 8/2010 |

OTHER PUBLICATIONS

Crowson, et al. A phase II study to evaluate tamoxifen in pancreatic adenocarcinoma. Eur J Surg Oncol. 1986;12(4):335-6.

Dongiovanni, et al. Gefitinib (ZD1839): Therapy in selected patients with non-small cell lung cancer (NSCLC)? Lung Cancer. Feb. 1, 2008 [Epub ahead of print] Availabel at: http://www.ncbi.nlm.nih.gov/pubmed/18243402 Last accessed Mar. 5, 2008.

Duell, et al. A population-based study of the Arg399GIn polymorphism in X-ray repair cross-complementing group 1 (XRCCI) and risk of pancreatic adenocarcinoma. Cancer Res 2002;62:4630-6.

Early Breast Cancer Trialists' Collaborative Group. Tamoxifen for early breast cancer. The Cochrane Database of Systematic Reviews 2008 Issue 1. Available at: http://www.cochrane.org/reviews/en/ab000486.html. Last accessed Mar. 4, 2008.

Edwards, et al. Resistance to therapy caused by intragenic deletion in BRCA2. Nature. 2008;451(7182):1111-5.

Erowid. Introduction to the Federal Controlled Substance Analogue Act. 2001. Available at ttp://www.erowid.org/psychoactives/law/analog/analog_info1.shtml. Accessed Oct. 13, 2006. (4 pages).

Fierce Biotech. Avastin encounters rare failure for pancreatic cancer. Fierce Biotech Web site. Jun. 26, 2006. Available at: http://www.fiercebiotech.com/story/avastin-encounters-rare-failure-for-pancreatic-cancer/2006-06-27 Last accessed Mar. 4, 2008.

Fisher, et al. Endometrial cancer in tamoxifen-treated breast cancer patients: findings from the National Surgical Adjuvant Breast and Bowel Project (NSABP) B-14. J Natl Cancer Inst 1994; 86:527-37.

Gurpide, E. Endometrial Cancer: Biochemical and Clinical Correlates. J Natl Cancer Inst 1991;83(6): 405-416.

Hegi, et al. MGMT gene silencing and benefit from temozolomide in glioblastoma. N. Engl J Med. 2005 10;352(10):997-1003.

Ishii, et al. Efficacy of temozolomide is correlated with 1p loss and methylation of the deoxyribonucleic acid repair gene MGMT in malignant gliomas. Neurol Med Chir (Tokyo). Aug. 2007;47(8):341-9.

Kume, et al. Mutations in the serine protease inhibitor Kazal type 1 (SPINK1) gene in Japanese patients with pancreatitis. Pancreatology 2005;5:354-60.

Kurman, R.J. Blaustein's Pathology of the Female Genital Tract. 4th ed. Springer-Verlag. New-York 1994.

Li, et al. Pancreatic cancer. Lancet 2004;363:1049-57.

Marchesi, et al. Triazene compounds: mechanism of action and related DNA repair systems. Pharmacol Res. Oct. 2007;56(4):275-87.

National Cancer Institute. Bevacizumab Combined With Chemotherapy Improves Progression-Free Survival for Patients With Advanced Breast Cancer. U.S. National Institutes of Health. 2005. Available at: http://www.cancer.gov/newscenter/pressreleases/AvastinBreast. Last Accessed Mar. 4, 2008.

Paez, et al. EGFR mutations in lung cancer: correlation with clinical response to gefitinib therapy. Science. 2004 4;304(5676):1497-500.

Palmer, et al. Hypoxia-selective antitumor agents. 9. Structure-activity relationships for hypoxia-selective cytotoxicity among analogues of 5-[N,N-bis(2-chloroethyl)amino]-2,4-dinitrobenzamide. J Med Chem. 1994; 37(14):2175-84. (p. 2175 only).

Pao, et al. EGF receptor gene mutations are common in lung cancers from "never smokers" and are associated with sensitivity of tumors to gefitinib and erlotinib. Proc Natl Acad Sci U S A. Sep. 7, 2004;101(36):13306-11.

Porta, et al. Serum concentrations of organochlorine compounds and K-ras mutations in exocrine pancreatic cancer. PANKRAS II Study Group. Lancet 1999;354:2125-9.

Roche—Media News. US Phase III study of Avastin in advanced pancreatic cancer does not meet primary endpoint. Basel, Jun. 27, 2006. Roche Web site. Available at: http://www.roche.com/home/media/med-cor/med-cor-2006/med-cor-2006-06-27.htm?printout=1 Last accessed Mar. 4, 2008.

Sakai, et al. Secondary mutations as a mechanism of cisplatin resistance in BRCA2-mutated cancers. Nature. Feb. 10, 2008;451:1116-21.

Shah, et al. Selenium disrupts estrogen receptor (alpha) signaling and potentiates tamoxifen antagonism in endometrial cancer cells and tamoxifen-resistant breast cancer cells. Mol Cancer Ther. 2005;4(8):1239-49.

Shaw, et al. Practice parameters in adults with suspected or known supratentorial nonoptic pathway low-grade glioma. Neurosurg. Focus. 4(6), Article 10, 1998.

Tuma, et al. Targeting DNA Repair in BRCA Mutation Carriers. Oncology Times. Sep. 25, 2007;29(18):52-53.

Wiewrodt, et al. MGMT in primary and recurrent human glioblastomas after radiation and chemotherapy and comparison with p53 status and clinical outcome. Int J Cancer. Mar. 15, 2008;122(6):1391-9.

Williams, et al. Tamoxifen for relapse of ovarian cancer. Cochrane Database of Systematic Reviews 1998, Issue 2. Available at: http://www.cochrane.org/reviews/en/ab001034.html Last accessed Mar. 4, 2008.

Wolff, M. E. Ed. Burger's Medicinal Chemistry and Drug Discovery. Fifth Edition. vol. 1: Principles and Practice. John Wiley & Sons. 1995:975-977.

Aachmann, F. L. et al. (2003). "Structural Background of Cyclodextrin-Protein Interactions," Prot. Eng. 16(12):905-912.

Arnold, N. et al. (May 1996). "Overrepresentation of 3q and 8q Material and Loss of 18q Material Are Recurrent Findings in Advanced Human Ovarian Cancer," Genes Chromosomes Cancer, 16(1):46-54.

Arnone, C. et al. (Apr. 18, 1997). Nucleophilic Substitution Reactions of 1-Halogeno-4-COR-2- Nitrobenzenes and 1-Halogen-6-COR-2 Nitrobenzenes with Sodium Benzenethiolate and Piperidine. Can an Inverted Built-In Solvation be Responsible for the Peculiar Activation by an o-Carboxamido Group in $S_nAr$ Reactions With an Anionic Nucleophile? J. Org. Chem. 62(10):3093-3097.

Audebert, M. et al. (Dec. 31, 2004)."Involvement of Poly(ADP-Ribose) Polymerase-1 and XRCC1/DNA Ligase III in an Alternative Route for DNA Double-Strand Breaks Rejoining," J. Biol. Chem. 279(53):55117-55126. Epub Oct. 21, 2004.

Ayhan, A. et al. (2006). "Topotecan as a Second-Line Therapy in Patients With Ovarian and Primary Peritoneal Cancer: Initial Response and Long-Term Follow-Up," Eur. J. Gynaecol Oncol. 27(6):603-606.

Bale, A. E. et al. (1997). "The Nevoid Basal Cell Carcinoma Syndrome: Genetics and Mechanism of Carcinogenesis," Cancer Invest. 15(2):180-186.

Ball, H. G. et al. (Aug. 1996). "A Phase II Trial of Paclitaxel in Patients With Advanced or Recurrent Adenocarcinoma of the Endometrium: A Gynecologic Oncology Group Study," Gynecologic Oncology 62(2):278-281.

Banasik, M. et al. (1992). "Specific Inhibitors of Poly(ADP-Ribose) Synthetase and Mono(ADP-Ribosyl)Transferase," J. Biol. Chem. 267:1569-1575.

Bauer, P. I. et al. (2002). "Anti-Cancer Action of 4-Iodo-3-Introbenzamide in Combination With Buthionine Sulfoximine: Inactivation of Poly(ADP-Ribose) Polymerase and Tumor Glycolysis and the Appearance of a Poly(ADP-Ribose) Polymerase Protease," *Biochem. Pharmacol.* 63(3):455-462.

Bauer, P. I. et al. (2005). "The Influence of ATP on Poly(ADP-Ribose) Metabolism," *Int'l. J. Mol. Med.* 16:321-324.

Bello, M. J. et al. (Jan. 15, 1990). "Chromosome Aberrations in Metastatic Ovarian Cancer: Relationship With Abnormalities in Primary Tumors," *Int. J. Cancer* 45(1):50-54.

Ben-Hur, E. et al. (1984). "Inhibitors of Poly (ADP-Ribose) Synthesis Enhance Radiation Response by Differentially Affecting Repair of Potentially Lethal Versus Sublethal Damage," *British Journal of Cancer* 49:34-42.

Bentle, M. S. et al. (2006). "New Tricks for Old Drugs: the Anticarcinogenic Potential of DNA Repair Inhibitors," *J. Mol. Histol.* 37(5-7):203-218.

Berchuck, A. et al. (Jan. 1991). "Overexpression of HER-2/Neu in Endometrial Cancer is Associated With Advanced Stage Disease," *Am. J. Obstet. Gynecol.* 164(1 Pt. 1):15-21.

Berger, N. (1985). "Poly(ADP-Ribose) in the Cellular Response to DNA Damage," *Radiation Research* 101:4-14.

Berkow, R. ed., (Aug. 1987). "Chapter 105. Oncology—Treatment and Prognosis," in *The Merck Manual of Diagnosis and Therapy*, 15th ed. Merck & Co., Inc., pp. 1218-1225 and Table of Contents.

Bhattacharjee, A. et al. (Nov. 20, 2001). "Classification of Human Lung Carcinomas by mRNA Expression Profiling Reveals Distinct Adenocarcinoma Subclasses," *Proc. Natl. Acad. Sci. USA* 98(24):13790-13795. (Epub. Nov. 13, 2001).

Bonadonna, G. et al. (Jan. 1998). "Primary Chemotherapy in Operable Breast Cancer: Eight-Year Experience at the Milan Cancer Institute," *J. Clin. Oncol.* 16(1):93-100.

Borczuk, A. C. et al. (Nov. 2003). "Non-Small-Cell Lung Cancer Molecular Signatures Recapitulate Lung Development Pathways," *Am. J. Pathol.* 163(5):1949-1960.

Bouchard, V. et al. (Jun. 2003). "PARP-1, a Determinant of Cell Survival in Response to DNA Damage," *Exp. Hematol;.* 31(6):446-454.

Bryant, H.E. et al. (Apr. 14, 2005). "Specific Killing of BRCA2-Deficient Tumours with Inhibitors of Poly(ADP-Ribose) Polymerase," *Nature* 434(7035):913-917; and *Erratum in Nature* (May 17, 2007) 447(7142):346.

Buki, K. G. et al. (1991). "Destabilization of $Zn^{2+}$Coordination in ADP-Ribose Transferase (Polymerizing) by 6-Nitroso-1,2-Benzopyrone Coincidental With Inactivation of the Polymerase but not the DNA Binding Function," *FEBS Lett.* 290:181-185.

Buki, K.G. et al. (1992). "Inactivation of the Polymerase but not the DNA Binding Function of ADPRT by Destabilization of one of its $Zn^{2+}$Coordination Centers by 6-Nitroso-1,2-Benzopryone," in *ADP-Ribosylation Reactions*, Poirier, G.G. et al., eds., Springer-Verlag: New York, NY, pp. 329-333.

Cepeda, V. et al. (2006). "Poly(ADP-ribose) Polymerase-1 (PARP-1) Inhibitors in Cancer Chemotherapy," *Rec. Pat. Anti-Cancer Drug Discov.* 1:39-53.

Chakraborty, A. K. et al. (Mar. 1, 2008). "Co-Targeting Insulin-Like Growth Factor I Receptor and HER2: Dramatic Effects of HER2 Inhibitors on Nonoverexpressing Breast Cancer," *Cancer Res.* 68(5):1538-1545.

Chang, J. W. et al. (May 2000). "Correlation of Genetic Instability With Mismatch Repair Protein Expression and P53 Mutations in Non-Small Cell Lung Cancer," *Clin. Cancer Research* 6(5):1639-1646.

Chang, P. et al. (Dec. 2, 2004). "Poly(ADP-ribose) is Required for Spindle Assembly and Structure," *Nature* 432(7017):645-649.

Chen, Q.-R. et al. (2007). "Diagnosis of the Small Round Blue Cell Tumors Using Multiplex Polymerase Chain Reaction," *Journal of Molecular Diagnostics* 9(1):80-88.

Chevallier, B. et al. (1993). "Inflammatory Breast Cancer. Pilot Study of Intensive Chemotherapy (FEC-HD) Results in a High Histologic Response Rate," *Am. J. Clin. Oncol.* 16:223-228.

Chin, K. et al. (Dec. 2006). "Genomic and Transcriptional Aberrations Linked to Breast Cancer Pathophysiologies," *Cancer Cell* 10(6)529-541.

Christie, M. et al. (2006). "Molecular Pathology of Epithelial Ovarian," *Journal of the British Menopause Society* 12(2):57-63.

Chu, S. et al. (Aug. 24, 2007). "Poly(ADP-Ribose) Polymerase-1 Regulates Vimentin Expression in Lung Cancer Cells," *Am. J. Physiol.: Lung, Cell. Mol. Physiol.* 293:L1127-L1134.

Chuang, A. J. et al. (1994). "Comparison of the Cytotoxic and Antiretroviral Effects of 3-Nitrosobenzamide and 4-Iodo-3-Nitrobenzamide," *Proc. West. Pharmacol. Soc.* 37:117-119.

Classen, S. et al. (Sep. 16, 2003). "Structure of the Topoisomerase II ATPase Region and its Mechanism of Inhibition by the Chemotherapeutic Agent ICRF-187," *Proc. Natl. Acad. Sci. USA* 100(19):10629-10634, including Erratum published on Nov. 25, 2003, *Proc. Natl. Acad. Sci. USA* 100(24):14510-14511.

Cleator, S. et al. (Mar. 2007). "Triple-Negative Breast Cancer: Therapeutic Options," *Lancet Oncol.* 8:235-244.

Clinical Trials. US Government (2008). Evaluation of Paclitaxel (Taxol, NSC #673089), Carboplatin (Paraplatin, NSC #241240), and BSI-201 (NSC #746045, IND #71,677) in the Treatment of Advanced, Persistent, or Recurrent Uterine Carcinosarcoma, Verified by BiPar Sciences, Jul. 2009, first received: May 28, 2008 Last Updated: Jul. 23, 2009, located at http://clinicaltrials.gov/ct2/show/NCT00687687, last visited on Sep. 18, 2009.

Comen, E. A. et al. (May 20, 2008). "Prevalence of *BRCA1* and *BRCA2* Mutations in Jewish Women with Triple Negative Breast Cancer," 44th *Annual Meeting of the American Society of Clinical Oncology*, May 30-Jun. 3, 2008, Chicago, IL, a supplement to the *J. Clin. Oncol.* 26(15S):749s, Abstract 22002, which can be located at <http://www.jco.ascopubs.org/cgi/mgca...>, last visited on Jun. 14, 2009, eight pages total.

Cosi, C. et al. (1994). "Poly(ADP-Ribose) Polymerase: Early Involvement in Glutamate-Induced Neurotoxicity in Cultured Cerebellar Granule Cells," *J. Neurosci. Res.* 39:38-46.

Cosi, C. et al. (2002). "New Inhibitors of Poly(ADP-Ribose) Polymerase and Their Therapeutic Targets," *Exp. Opin. Therapeut. Pat.* 12(7):1047-1071.

Costantino, G. et al. (2001). "Modeling of Poly(ADP-Ribose)Polymerase (PARP) Inhibitors. Docking of Ligands and Quantitative Structure-Activity Relationship Analysis," *J. Med. Chem.* 44(23): 3786-3794.

Curtin, J. P. et al. (Nov. 2001). "Paclitaxel in the Treatment of Carcinosarcoma of the Uterus: A Gynecologic Oncology Group Study," *Gynecologic Oncology* 83(2):268-270.

D'Adda Di Fagagna, F. et al. (Sep. 1999). "Functions of Poly(ADP-Ribose) Polymerase in Controlling Telomere Length and Chromosomal Stability," *Nature Genetics* 23(1):76-80.

D Amours, D. et al. (Sep. 1, 1999). "Poly (ADP-Ribosyl)ation Reactions in the Regulation of Nuclear Functions," *Biochem J.* 342(Part 2):249-268.

Deger, R. B. et al. (Jul. 15, 1997). "Karyotic Analysis of 32 Malignant Epithelial Ovarian Tumors," *Cancer Genet. Cytogenet.* 96(2):166-173.

Delattre, O. et al. (Sep. 10, 1992). "Gene Fusion With an *ETS* DNA-Binding Domain Caused by Chromosome Translocation in Human Tumours," *Nature* 359(6391):162-165.

Delattre, O. et al. (Aug. 4, 1994). "The Ewing Family of Tumors—A Subgroup of Small-Round-Cell Tumors Defined by Specific Chimeric Transcripts," *N. Engl. J. Med.* 331(5):294-299.

Dent, R. et al. (Aug. 1, 2007). "Triple-Negative Breast Cancer: Clinical Features and Patterns of Recurrence," *Clin. Cancer Res.* 13(15 Pt 1):4429-4434.

De Soto, J. A. et al. (Jul. 15, 2006). "PARP-1 Inhibitors: Are They the Long-Sought Genetically Specific Drugs for BRCA1/2-Associated Breast Cancers?" *Int. J. Med. Sci.* 3(4):117-123.

De Soto, J. et al. (2006). "The Inhibition and Treatment of Breast Cancer with Poly (ADP-Ribose) Polymerase (PARP-1) Inhibitors," *Int. J. Biol. Sci.* 2(4):179-185.

Diebold, J. et al. (Apr. 2000). "20q13 and Cyclin D1 in Ovarian Carcinomas. Analysis by Fluorescence *in Situ* Hybridization," *J. Pathol.* 190(5):564-571.

Donawho, C. K. et al. (May 1, 2007). "ABT-888, an Orally Active Poly(ADP-Ribose) Polymerase Inhibitor that Potentiates DNA-Damaging Agents in Preclinical Tumor Models," *Clin. Cancer Res.* 13(19):2728-2737.

Donawho, C. K. et al. (2008). "The PARP Inhibitor, ABT-888 Overcomes Resistance in Temozolomide-Refractory Prostate and Breast Xenograft Tumors Implanted in Metastatic Sites In Vivo," Meeting Poster No. 555 (one page), and Palma, J. et al. (Oct. 24, 2008). "The PARP Inhibitor, ABT-888 Overcomes Resistance in Temozolomide-Refractory Prostate and Breast Xenograft Tumors Implanted in Metastatic Sites In Vivo," $20^{th}$ EORTC-NCI-AACR, Symposium on Molecular Targets and Cancer Therapeutics, European Journal of Cancer Supplements 6(12):175, poster No. 555.

Donegan, W. L. et al., eds., (1988). Cancer of the Breast, $3^{rd}$ Edition, W. B. Saunders: Philadelphia, PA, in Chapter 17 entitled Endocrine Therapy of Breast Cancer, by C. G. Cardinal, pp. 504-506.

Dracopoli, N. C. et al. (Aug. 1, 1987). "Loss of Heterozygosity at Autosomal and X-Linked Loci During Tumor Progression in a Patient With Melanoma," Cancer Research 47(15):3995-4000.

Drew, Y. et al. (Sep. 2008). "The Potential of PARP Inhibitors in Genetic Breast and Ovarian Cancers," Ann. N.Y. Acad. Sci. 1138:136-145.

Durkacz, B. W. et al. (Feb. 7, 1980). "(ADP-Ribose)$_n$ Participates in DNA Excision Repair," Nature 283:593-596.

Ellis, M.K. et al. (Apr. 15, 1992). "Reactions of Nitrosonitrobenzenes with Biological Thiols: Identification and Reactivity of Glutathion-S-yl Conjugates," Chem. Biol. Interactions 82(2):151-163.

Eyer, P. et al. (1980). "Biotransformation of Nitrosobenzene in the Red Cell and the Role of Glutathione," Xenobiotica 10(7/8):517-526.

Farmer, H. et al. (Apr. 14, 2005). "Targeting the DNA Repair Defect in BRCA Mutant Cells as a Therapeutic Strategy," Nature 434(7035):917-921.

Filmus, J. et al. (Jan. 1987). "Epidermal Growth Factor Receptor Gene-Amplified MDA-468 Breast Cancer Cell Line and its Nonamplified Variants," Mol. Cell. Biol. 7(1):251-257.

Fisher, B. et al. (Jul. 1997). "Effect of Preoperative Chemotherapy on Local-Regional Disease in Women With Operable Breast Cancer: Findings From the National Surgical Adjuvant Breast and Bowel Project B-18," J. Clin. Oncol. 15(7):2483-2493.

Fisher, B. et al. (Aug. 1998). "Effect of Preoperative Chemotherapy on the Outcome of Women With Operable Breast Cancer," J. Clin. Oncol. 16(8):2672-2685.

Flemming, G. F. (Jun. 1, 2004). "Phase III Trial of Doxorubicin plus Cisplatin With or Without Paclitaxel Plus Filgrastim in Advanced Endometrial Carcinoma: A Gynecologic Oncology Group Study," J. Clin. Oncol. 22(11):2159-2166; and comment in Curr. Oncol. Rep. (Nov. 2004). 6(6):455.

Flemming, G. F. et al. (Aug. 2004). "Phase III Randomized Trial of Doxorubicin + Cisplatin Versus Doxorubicin + 24-h Paclitaxel + Filgrastim in Endometrial Carcinoma, A Gynecologic Oncology Group Study," Ann. Oncol. 15(8):1173-1178.

Fletcher, J. A. et al. (Mar. 1991). "Ovarian Granulosa-Stromal Cell Tumors Are Characterized by Trisomy 12," Am. J. Pathol. 138(3):515-520.

Fong, P. C. et al. (2006). "Phase I Pharmacokinetic (PK) and Pharmacodynamic (PD) Evaluation of a Small Molecule Inhibitor of Poly ADP-Ribose Polymerase (PARP), KU-0059436 (Ku) in Patients (p) With Advanced Tumours," Supplement to Journal of Clinical Oncology, 2006 ASCO Annual Meeting Proceedings, Part I. vol. 24, No. 18S, Part I of II, (Jun. 20, 2006), p. 126s, abstract No. 3022.

Gäken, J. O. et al. (Jun. 1996). "Efficient Retroviral Infection of Mammalian Cells is Blocked by Inhibition of Poly(ADP-Ribose) Polymerase Activity," Journal of Virology 70(6):3992-4000.

Gallion, H. H. et al. (Sep. 1990). "Chromosome Abnormalities in Human Epithelial Ovarian Malignancies," Gynecol. Oncol. 38(3):473-477.

Garber, M. E. et al. (Nov. 20, 2001). "Diversity of Gene Expression in Adenocarcinoma of the Lung," Proc. Natl. Acad. Sci. USA 98(24):13784-13789. (Epub Nov. 13, 2001) and Erratum in Proc. Natl. Acad. Sci. USA (Jan. 22, 2002). 99(2):1098.

Garber, J. E. et al. (Dec. 14-17, 2006). "Neo-Adjuvant Cisplatin (CDDP) in 'Triple-Negative' Breast Cancer (BC)," Breast Cancer Research and Treatment, Special Issue, $29^{th}$ San Antonio Breast Cancer Symposium 2006; vol. 100, Poster Session III, p. S149, Abstract No. 3074.

Goldstein, J. (Feb. 13, 2008). "Latest Avastin Breast Cancer Study Unlikely to Sway FDA," The Wall Street Journal located at http://blogs.wsj.com/health/2008/02/13/latest-avastin-breast-cancer-study-unlikely-to-sway-fda/, last visited on Feb. 15, 2008, 3 pages total.

Greenfacts.org. Definition of Solid Cancer, located at http://222.greenfacts.org/glossary/pqrs/solid-cancer.htm, last visited Jul. 18, 2009, one page total.

Griffin, R. J. et al. (Sep. 1995). "Novel Potent Inhibitors of the DNA Repair Enzyme Poly(ADP-Ribose)Polymerase (PARP)," Anticancer Drug Design 10(6):507-514.

Griffin, R. J. et al. (Jan. 10, 1996). "Novel Benzimidazole and Quinazolinone Inhibitors of the DNA Repair Enzyme Poly(ADP-Ribose)Polymerase," Pharmaceutical Sciences 2(1):43-47.

Griffin, R. J. et al. (1998). Resistance-Modifying Agents. 5. Synthesis and Biological Properties of Quinazolinone Inhibitors of the DNA Repair Enzyme Poly(ADP-Ribose) Polymerase (PARP). J. Med. Chem. 41:5247-5256.

Gudmundsdottir, K. et al. (Sep. 25, 2006). "The Roles of BRCA1 and BRCA2 and Associated Proteins in the Maintenance of Genomic Stability," Oncogene 25(43):5864-5874.

Hakam, A. et al. (Feb. 1987). "Catalytic Activities of Synthetic Octadeoxyribonucleotides as Coenzymes of Poly(ADP-Ribose) Polymerase and the Identification of a New Enzyme Inhibitory Site," FEBS Lett. 212(1):73-78.

Harris, N. L. et al. (Dec. 1999). "World Health Organization Classification of Neoplastic Diseases of the Hematopoietic and Lymphoid Tissues: Report of the Clinical Advisory Committee Meeting-Airlie House, Virginia, Nov. 1997," J. Clin. Oncol. 17(12)3835-3849.

Hassa, P. O. et al. (Dec. 7, 2001). "The Enzymatic and DNA Binding Activity of PARP-1 Are Not Required for NF-kB Coactivator Function," J. Biol. Chem. 276(49):45588-45597.

Hassa, P. O. et al. (Sep. 2006). "Nuclear ADP-Ribosylation Reactions in Mammalian Cells: Where Are We Today and Where Are We Going?" Microbiol. Mol. Biol. Rev. 70(3):789-829.

Heighway, J. et al. (Oct. 31, 2002). "Expression Profiling of Primary Non-Small Cell Lung Cancer for Target Identification," Oncogene 21(50):7749-7763.

Helleday, T. et al. (Mar. 2008). "DNA Repair Pathways as Targets for Cancer Therapy," Nat. Rev. Cancer. 8(3):193-204.

Hellström, I. et al. (Mar. 15, 2001). "Over-expression of HER-2 in Ovarian Carcinomas," Cancer Res. 61(6):2420-2423.

Henderson, Z. et al. (Aug. 25, 1981). "Primary Structure of the Low Molecular Weight Nucleic Acid-binding Proteins of Murine Leukemia Viruses," J. Biol. Chem. 256(16):8400-8403.

Herceg, Z. et al. (Jun. 2, 2001). "Functions of Poly(ADP-Ribose) Polymerase (PARP) in DNA Repair, Genomic Integrity and Cell Death," Mutat. Res. 477(1-2):97-110.

Hickman, J. A. (Sep. 1975). "Protection Against the Effects of the Antitumour Agent CB 1954 by Certain Imidazoles and Related Compounds," Biochemical Pharmacology 24(17):1947-1952.

Higashi, T. et al. (1983). "Retrospects and Prospects," Glutathione: Storage, Transport and Turnover in Mammals, eds., Sakamoto, Y. et al. Japan Sci. Soc. Press, Tokyo,/VNU Science Press, Utrecht, pp. 3-9.

Hod, Y. (Dec. 1992). "A Simplified Ribonuclease Protection Assay," Biotechniques 13(6):852-854.

Höglund, M. et al. (Jun. 15, 2003). "Ovarian Carcinoma Develops Through Multiple Modes of Chromosomal Evolution," Cancer Research 63(12):3378-3385.

Homesley, H. D. et al. (Feb. 10, 2007). "Phase III Trial of Ifosfamide With or Without Paclitaxel in Advanced Uterine Carcinosarcoma: A Gynecologic Oncology Group Study," J. Clin. Oncol. 25(5):526-531.

Honkoop, A. H. et al. (1998). "Prognostic Role of Clinical, Pathological and Biological Characteristics in Patients with Locally Advanced Breast Cancer," Br. J. Cancer 77(4):621-626.

Hubert, A. et al. (Aug.-Sep. 2004). "PARP-1, PARP-2 and ATM in the DNA Damage Response: Functional Synergy in Mouse Development," DNA Repair (Amst). 3(8-9):1103-1108.

Hwang, S. J. et al. (Aug. 2003). "Lung Cancer Risk in Germline p53 Mutation Carriers: Association Between an Inherited Cancer Predisposition, Cigarette Smoking, and Cancer Risk," Hum. Genet. 113(3):238-243. Epub. Jun. 11, 2003.

Irvin, Jr. et al. (Dec. 2008). "What is Triple-Negative Breast Cancer?" *Eur. J. Cancer* 44(18):2799-2805.

Iwabuchi, H. et al. (Dec. 15, 1995). "Genetic Analysis of Benign, Low-Grade, and High-Grade Ovarian Tumors," *Cancer Res.* 55(24):6172-6180.

Jacob, D. A. et al. (2007). "Combination Therapy of Poly (ADP-Ribose) Polymerase Inhibitor 3-Aminobenzamide and Gemcitabine Shows Strong Antitumor Activity in Pancreatic Cancer Cells," *J. Gastroenterol. Hepatol.* 22:738-748.

Jagtap, P. et al. (2002). "Novel Phenanthridinone Inhibitors of Poly (Adenosine 5'-Diphosphate-Ribose) Synthetase: Potent Cytoprotective and Antishock Agents," *Crit. Care Med.* 30(5):1071-1082.

Jagtap, P. et al. (May 2005). "Poly(ADP-Ribose) Polymerase and the Therapeutic Effects of its Inhibitors," *Nature Rev. Drug Disc.* 4:421-440.

Jemal, A. et al. (Jan./Feb. 2003). Cancer Statistics 2003). *CA Cancer J. Clin.* 53(1):5-26.

Jenkins, R. B. et al. (Nov. 1993). "Cytogenetic Studies of Epithelial Ovarian Carcinoma," *Cancer Genet. Cytogenet.* 71(1):76-86.

Jeon, I. S. et al. (Mar. 16, 1995). "A Varian Ewing's Sarcoma Translocation (7;22) Fuses the *EWS* Gene to the ETS Gene *ETV1*," *Oncogene* 10(6):1229-1234.

Jones, C. et al. (Oct. 2008). "PARP Inhibitors and Cancer Therapy—Early Results and Potential Applications," *Br. J. Radiol.* 81 Spec No. 1:S2-S5.

Kandel, M. J. et al. (2006). "Prevalence of BRCA1 Mutations in Triple Negative Breast Cancer (BC)," *2006 ASCO Annual Meeting, Supplemental to the Journal of Clinical Oncology*, Jun. 20, 2006, Part I, vol. 24, No. 18S, abstract No. 508.

Karczewski, J. M. et al. (1999). "Prevention of Oxidant-Induced Cell Death in Caco-2 Colon Carcinoma Cells after Inhibition of Poly(ADP-Ribose) Polymerase and $Ca^{2+}$ Chelation: Involvement of a Common Mechanism," *Biochem. Pharmacol.* 57:19-26.

Khalid, M. N. et al. (Apr. 2006). "Long Circulating Poly(Ethylene Glycol)-Decorated Lipid Nanocapsules Deliver Docetaxel to Solid Tumors," *Pharm. Res.* 23(4):752-758.

Kiechle, M. et al. (Feb. 1, 2001). "Comparative Genomic Hybridization Detects Genetic Imbalances in Primary Ovarian Carcinomas as Correlated With Grade of Differentiation," *Cancer* 91 (3):534-540.

Kiechle-Schwarz, M. et al. (Nov. 1994). "Recurrent Cytogenetic Aberrations and Loss of Constitutional Heterozygosity in Ovarian Carcinomas," *Gynecol. Oncol.* 55(2):198-205.

Kim, M. Y. et al. (Dec. 17, 2004). "$NAD^+$-Dependent Modulation of Chromatin Structure and Transcription by Nucleosome Binding Properties of PARP-1," *Cell* 119(6):803-814.

Kindler, H. L. (2007) "A Double-Blind, Placebo-Controlled, Randomized Phase III Trial of Gemcitabine (G) Plus Bevacizumab (B) Versus Gemcitabine plus Placebo (P) in Patients (pts) with Advanced Pancreatic Cancer (PC): A Preliminary Analysis of Cancer and Leukemia Group B (CALGB) 80303," Gastrointestintal Cancers Symposium: Mutidisciplinary Approaches to the Prevention, Diagnosis, and Therapy of GI Cancers, Jan. 19-21, 2007, Orlando, Florida, p. 319, abstract 108.

Kirsten, E. et al. (2000). "Cancer Cell Selectivity of 5-Iodo-6-Aminobenzopyrone (INH2BP) and Methyl 3-5-Diiodo-4(4'-Methoxyphenol) Benzoate (DIME)," *Int'l J. Mol. Med.* .5(3):279-281.

Kiyohara, C. et al. (Sep. 2002). "Genetic Polymorphisms and Lung Cancer Susceptibility: A Review," *Lung Cancer* 37(3):241-256.

Ko, A. H. (Feb. 17, 2003), "Cancer of the Pancreas," published by Cancer Supportive Care Programs, article located at http://www.cancersupportivecare.com/pancreas/html, last visited on Sep. 23, 2009, 5 pages total.

Kosower, E.M. (1976). "Chemical Properties of Glutathione," Chapter 1 in *Glutathione Metabolism and Function*, Arias, M. et al., eds., Raven Press: New York, NY, Kroc Foundation Series, vol. 6, pp. 1-15.

Kuerer H. M., et al. (1998). "Pathologic Tumour Response in the Breast Following Neoadjuvant Chemotherapy Predicts Axillary Lymph Node Status," *Cancer J. Sci. Am.* 4:230-236.

Kuerer H. M. et al. (Feb. 1999). "Clinical Course of Breast Cancer Patients With Complete Pathologic Primary Tumour and Axillary Lymph Node Response to Doxorubicin-Based Neoadjuvant Chemotherapy," *J. Clin. Oncol.* 17(2):460-469.

Kun, E. et al. (1983). "Biochemical Basis of the Regulatory Role of Polyadenosine Diiphosphoribose," *Advances in Enzyme Regulation* 21:177-199.

Kun, E. et al. (Mar.-Jun. 2001). "Cell Biological Functions of PARP-1: An Overview," *Ital. J. Biochem.* 50(1-2):15-18.

Kun, E. et al. (2003). "Synergistic Anticancer Action of Reversibly and Irreversibly Acting Ligands of Poly (ADP-Ribose) Polymerase," *Int'l J. Mol. Med.* 11(2):191-193.

Kun, E. et al. (2006). "Quantitative Correlation Between Cellular Proliferation and Nuclear Poly (ADP-Ribose) Polymerase (PARP-1)," *Int'l J. Mol. Med.* 17:293-300.

Lau, A. et al. (Oct. 21-24, 2008). Pre-Clinical Activity of the PARP Inhibitor Olaparib (AZD2281) in Homologous Recombination Repair Deficient Triple Negative Breast Cancer, Poster at *20th EORTC-NCI-AACR Symposium on "Molecular Targets and Cancer Therapeutics*," Oct. 21-24, 2008, Geneva, Switzerland, two pages.

Lee-Jones, L. (Aug. 2003). "Ovary: Germ Cell Tumors," *Atlas of Genetics and Cytogenetics in Oncology and Haematology*, pp. 591-605, located at http://atlasgeneticsoncology.org/Tumors/OvarianGermCellID5067.pdf, last visited on Sep. 25, 2009, 15 pages total.

Lee-Jones, L. (Nov. 2003). "Ovary: Sex Cord-Stromal Tumors," *Atlas of Genetics and Cytogenetics in Oncology and Haematology*, 8(1):125-131, located at http://AtlasGeneticsOncology.org/Tumors/OvarSexCordStromID5223.html, last visited on Sep. 25, 2009, 15 pages total.

Lee-Jones, L. (Dec. 2003). "Ovary: Epithelial Tumors," *Atlas Genet Cytogenet Oncol Haematol* 8(2):256-302, located at http://atlasgeneticsoncology.org/Tumors/OvaryEpithTumID5230.pdf, 51 pages total.

Leslie, K. K. et al. (2005). "Tyrosine Kinase Inhibitors in Endometrial Cancer," *International Journal of Gynecological Cancer* 15:409-411, abstract No. 0020.

Lev, D. C. et al. (Aug. 2003). "Dacarbazine Causes Transcriptional up-Regulation of Interleukin 8 and Vascular Endothelial Growth Factor in Melanoma Cells; A Possible Escape Mechanism From Chemotherapy," *Mol. Cancer Therap.* 2(8):753-763.

Lever, A. et al. (1989). "Identification of a Sequence Required for Efficient Packaging of Human Immunodeficiency Virus Type 1 RNA into Virus," *J. Virol.* 63(9):4085-4087.

Lewis, G. D. et al. (Sep. 1993). "Differential Responses of Human Tumor Cell Lines to Anti-p185HER2 Monoclonal Antibodies," *Cancer Immunol. Immunother.* 37(4):255-263.

Li, J.-H. et al. (2001). "Synthesis of Substituted 5[*H*]phenanthridin-6-ones as Potent Poly(ADP-Ribose)Polymerase-1 (PARP1) Inhibitors," *Bioorg. Med. Chem. Lett.* 11:1687-1690.

Loesch, D. M. (Dec. 8-11, 2005). "Phase II Trial of Gemcitabine Plus Carboplatin (plus Trastuzumab in HER-2 Positive Patients) in Metastatic Breast Cancer Patients," *Breast Cancer Research and Treatment, Special Issue 28th annual San Antonio Breast Cancer Symposium 2005*, San Antonio, Texas, vol. 94, Supplement 1, p. S280, Poster Session VI, Abstract No. 6092.

Marsit, C. J. et al. (Jan. 29, 2004). "Inactivation of the Fanconi Anemia/BRCA Pathway in Lung and Oral Cancers: Implications for Treatment and Survival," *Oncogene* 23(4):1000-1004.

Mayr, D. et al. (Sep. 2002). "Characteristic Pattern of Genetic Aberrations in Ovarian Granulosa Cell Tumors," *Mod. Pathol.* 15(9):951-957.

Mazzon, E. et al. (2001). "GPI 6150, a Poly (ADP-Ribose) Polymerase Inhibitor, Exhibits an Anti-Inflammatory Effect in Rat Models of Inflammation," *Eur. J. Pharmacol.* 415:85-94.

McCabe, N. et al. (Aug. 15, 2006). "Deficiency in the Repair of DNA Damage by Homologous Recombination and Sensitivity to Poly(ADP-ribose) Polymerase Inhibition," *Cancer Res.* 66(16):8109-8115.

McLaughlin, P. et al. (Aug. 1998). "Rituximab Chimeric Anti-CD20 Monoclonal Antibody Therapy for Relapsed Indolent Lymphoma: Half of Patients Respond to a Four-Dose Treatment Program," *J. Clin. Oncol.* 16(8):2825-2833.

McCluggage, W. G. (May 2002). "Malignant Biphasic Uterine Tumors: Carcinosarcomas or Metaplastic Carcinomas?" *J. Clin. Pathol.* 55(5):321-325.

Ménissier De Murcia, J. et al. (Jul. 8, 1997). "Requirement of Poly(ADP-Ribose) Polymerase in Recovery From DNA Damage in Mice and in Cells," *Proc. Natl. Acad. Sci. USA* 94(14):7303-7307.

Meric, C. et al. (Apr. 1989). "Characterization of Moloney Murine Leukemia Virus Mutants with Single-Amino-Acid Substitutions in the Cys-His Box of the Nucleocapsid," *J. Virol.* 63(4):1558-1568.

Mitsuuchi, Y. et al. (Oct. 30, 2002). "Cytogenetics and Molecular Genetics of Lung Cancer," *Am. J. Med. Genet.* 115(3):183-188.

Miller, D. S. et al. (Aug. 2005). "Phase II Evaluation of Topotecan in Carcinosarcoma of the Uterus: A Gynecologic Oncology Group Study," *Gynecologic Oncology* 98(2):217-221.

Mrózek, K. et al. (Mar. 1990). "Trisomy of Chromosome 12 in a Case of Thecoma of the Ovary," *Gynecol. Oncol.* 36(3):413-416.

Mugneret, F. et al. (Jun. 1988). "Chromosomes in Ewing's Sarcoma. II. Nonrandom Additional Changes, Trisomy 8 and der(16)t(1:16)," *Cancer Genet. Cytogenet.* 32(2):239-245.

Nahleh, Z. et al. (Nov. 2007). "Trastuzumab not for Ductal Carcinoma in Situ?" *Anticancer Drugs* 18(10):1231-1235.

Nahta, R. et al. (May 2006). "Mechanisms of Disease: Understanding Resistance to HER2-Targeted Therapy in Human Breast Cancer," *Nat. Clin. Pract. Oncol.* 3(5):269-280.

Narod, S. A. et al. (Sep. 2004). "*BRCA1* and *BRCA2*: 1994 and beyond," *Nat. Rev. Cancer* 4(9):665-676.

Nguewa, P. A. et al. (2003). "Pharmacological Modulation of Poly(ADP-Ribose) Polymerase-Mediated Cell Death: Exploitation In Cancer Chemotherapy," *Mol. Pharmacol.* 64(5):1007-1014.

Nitta, K. et al. (Mar. 1987). "Antitumor Activity of New Derivatives of Camptothecin," *Gan To Kagaku Ryoho.* 14(3 Pt 2):850-857. This article is in Japanese with English abstract on p. 857.

Nomura, F. et al. (May 2000). "Enhancement of Poly-Adenosine Diphosphate-Ribosylation in Human Hepatocellular Carcinoma," *J. Gastroenterol. Hepatol.* 15(5):529-535.

Ogston, K. N. et al. (2003). "A New Histological Grading System to Assess Response of Breast Cancers to Primary Chemotherapy: Prognostic Significance and Survival," *Breast* 12:320-327.

Olver, I. N. (Feb. 2008). "Trastuzumab as the Lead Monoclonal Antibody in Advanced Breast Cancer: Choosing Which Patient and When," *Future Oncol.* 4(1):125-131.

Omura, G. A. et al. (Aug. 15, 1983). "A Randomized Study of Adriamycin With and Without Dimethyl Triazenoimidazole Carboxamide in Advanced Uterine Sarcomas," *Cancer* 52(4):626-632.

Oosting-Lenstra, S. F. et al. (Dec. 2007). "Failure of CHOP with Rituximab for Lymphomatoid Granulomatosis," *Neth. J. Med.* 65(11):442-447.

(OSI)™ Pharmaceuticals, (Aug. 9, 2005). "Tarceva® (Erlotinib) Tablets NDA 21-743, S003, Supplemental NDA: Pancreatic Cancer, Briefing Document, ODAC Meeting Sep. 13, 2005," PDF located at http://www.fda.gov/ohrms/dockets/AC/05/briefing/2005-4174B1_03_01-OSI-Tarceva.pdf, 66 pages total, last visited Sep. 25, 2009.

Parker, R. M. C. et al. (1999). "mRNA: Detection by in Situ and Northern Hybridization," *Methods in Molecular Biology, Chapter 14*, 106:247-283.

Pedersen, M. I. et al. (Feb. 1, 1986). "Nonrandom Chromosome Structural Aberrations and Oncogene Loci in Human Malignant Melanoma," *Cancer Genet. Cytogenet.* 20(1-2):11-27.

Pejovic, T. et al. (May 1990). "Trisomy 12 is a Consistent Chromosomal Aberration in Benign Ovarian Tumors," *Genes Chromosomes Cancer* 2(1):48-52.

Pejovic, T. et al. (Jan. 1992). "Chromosome Aberrations in 35 Primary Ovarian Carcinomas," *Genes Chromosomes Cancer* 4(1):58-68.

Pejovic, T. et al. (Feb. 1995). "Genetic Changes in Ovarian Cancer," *Ann. Med.* 27(1):73-78.

Perkins, E. et al. (May 15, 2001). "Novel Inhibitors of Poly(ADP-Ribose) Polymerase/PARP1 and PARP2 Identified Using a Cell-Based Screen in Yeast," *Cancer Res.* 61:4175-4183.

Plummer, R. et al. (2005). "First in Human Phase I Trial of the PARP Inhibitor AG-014699 With Temozolomide (TMZ) in Patients (pts) With Advanced Solid Tumors, 2005 41$^{st}$ Annual Meeting of the American Society of Clinical Oncology, May 13-17, 2005, Orlando Florida, 2005 Annual Meeting Proceedings Part I, (a supplement to the Journal of Clinical Oncology," vol. 23, No. 16S, Part I of II (Jun. 1 Supplement), p. 208s, abstract No. 3065.

Plummer, R. et al. (2006)."First and Final Report of a Phase II Study of the Poly(ADP-Ribose) Polymerase (PARP) Inhibitor, AG014699, in Combination With Temozolomide (TMZ) in Patients With Metastatic Malignant Melanoma (MM)," 2006 42$^{nd}$ Annual Meeting of the American Society of Clinical Oncology, Jun. 2-6, 2006, Atlanta, GA, Supplement to the *Journal of Clinical Oncology*, Part I of II, vol. 24, No. 18S (Jun. 20, 2006) p. 456s, abstract No. 8013.

Powles, T. J. et al. (Mar. 1995). "Randomized Trial of Chemoendocrine Therapy Started Before or After Surgery for Treatment of Primary Breast Cancer," *J. Clin. Oncol.* 13(3):547-552.

Ramonas, K. et al. (2005). "Treatment of Transgenic Murine Retinoblastoma With 4-Iodo-3-Nitrobenzamide (INO$_2$BA), a Novel Chemotherapeutic Agent," *Invest. Ophthalmol. Vis. Sci.* 46(5):E-Abstract 3422-B975, 2 pages total.

Ratnam, K. et al. (Mar. 1, 2007). "Current Development of Clinical Inhibitors of Poly(ADP-Ribose) Polymerase in Oncology," *Clin. Cancer Res.* 13(5):1383-1388.

Rattan, S. I. et al. (Jun. 15, 1994). "Kinetin Delays the Onset of Ageing Characteristics in Human Fibroblasts," *Biochem. Biophys. Res. Comm.* 201(2):665-672.

Razzak, A. R. et al. (2008). "Heterogeneity of Breast Cancer and Implications of Adjuvant Chemotherapy," *Breast Cancer* 15(1):31-34.

Reis-Filho, J. S. et al. (2008). "Triple Negative Tumours: a Critical Review," *Histopathol.* 52:108-118.

Ries, L.A.G., et al. (eds). (2007) SEER Cancer Statistics Review, 1975-2004, National Cancer Institute. Bethesda, MD, based on Nov. 2006 SEER data submission, posted to the SEER web site, 2007, located at http://seer.cancer.gov/csr/1975_2004/.

Richmond, A. et al. (Mar. 1986). "Growth Factor and Cytogenetic Abnormalities in Cultured Nevi and Malignant Melanomas," *J. Invest. Dermatol.* 86(3):295-302.

Roberts, C. G. et al. (Sep. 1990). "Cytogenetic Study of Solid Ovarian Tumors," *Cancer Genet. Cytogenet.* 48(2):243-253.

Rottenberg, S. et al. (Nov. 4, 2008). "High Sensitivity of BRCA1-Deficient Mammary Tumors to the PARP Inhibitor AZD2281 Alone and in Combination With Platinum Drugs," *Proc. Natl. Acad. Sci. USA* 105(44):17079-17084.

Said, S. I. et al. (May 1996). "Excitotoxicity in the Lung: N-Methyl-D-Aspartate-Induced, Nitric Oxide-Dependent, Pulmonary Edema is Attenuated by Vasoactive Intestinal Peptide and by Inhibitors of Poly(ADP-Ribose) Polymerase," *Proc. Natl. Acad. Sci. USA* 93:4688-4692.

Sataloff, D. M. et al. (Mar. 1995). "Pathologic Response to Induction Chemotherapy in Locally Advanced Carcinoma of the Breast: a Determinant of Outcome," *J. Am.Coll. Surg.* 180(3):297-306.

Schlicker, A. et al. (Jan. 1, 1999). "4-Amino-1,8-Naphthalimide: a Novel Inhibitor of Poly(ADP-Ribose) Polymerase and Radiation Sensitizer," *Int. J. Radiat. Biol.* 75(1):91-100.

Schreiber, V. et al. (Jul. 2006). "Poly(ADP-ribose): Novel Functions for an Old Molecule," *Nat. Rev. Mol. Cell Biol.* 7(7):517-528.

Seracchioli, R. et al. (Jun. 2001). "Conservative Treatment of Recurrent Ovarian Fibromas in a Young Patient Affected by Gorlin Syndrome," *Hum. Reprod.* 16(6):1261-1263.

Serra, V. et al. (Oct. 1, 2008). "NVP-BEZ235, a Dual PI3K/mTOR Inhibitor, Prevents PI3K Signaling and Inhibits the Growth of Cancer Cells with Activating PI3K Mutations," *Cancer Res.* 68(19):8022-8030.

Silverberg, S. G. et al. (1991). "Carcinomas," in Tumors of the Uterine Corpus and Gestational Trophoblastic Disease, Atlas of Tumor Pathology, in 3$^{rd}$ Series, Fascicule 3, Washington D. C., Armed Forces Institute of Pathology, pp. 166-179.

Simbulan-Rosenthal, C. M. et al. (Oct. 10, 2000). "Misregulation of Gene Expression in Primary Fibroblasts Lacking Poly(ADP-Ribose) Polymerase," *Proc. Nat'l Acad. Sci. USA* 97(21):11274-11279.

Simbulan-Rosenthal, C. M. et al., (Nov. 20, 2003). "PARP-1 Binds E2F-1 Independently of its DNA Binding and Catalytic Domains, and Acts as a Novel Coactivator of E2F-1-Mediated Transcription During Re-Entry of Quiescent Cells into S Phase," *Oncogene* 22(52):8460-8471.

Simon, R. (Mar. 1989). "Optimal Two-Stage Designs for Phase II Clinical Trials," *Control Clin. Trials* 10(1):1-10.

Singh, N. (Jun. 14, 1991). "Enhanced Poly ADP-Ribosylation in Human Leukemia Lymphocytes and Ovarian Cancers," *Cancer Lett.* 58(1-2):131-135.

Shall, S. et al. (May 11, 1999). "Preparation of Aminobenzamides and Related Compounds as Inhibitors of Poly(ADP-Ribose)-Metabolizing Enzymes," *Chemical Abstracts* 116(19):193929e.

Slayton, R. E. et al. (Jun. 1987). "Phase II Trial of Etoposide in the Management of Advanced or Recurrent Mixed Mesodermal Sarcomas of the Uterus: A Gynecologic Oncology Group Study," *Cancer Treatment Reports* 71(6):661-662.

Sonoda, G. et al. (Dec. 1997b). "Comparative Genomic Hybridization Detects Frequent Overrepresentation of Chromosomal Material From 3q26, 8q24, and 20q13 in Human Ovarian Carcinomas," *Genes Chromosomes Cancer* 20(4):320-328.

Soriano, F. G. et al. (Jan. 2001). "Diabetic Endothelial Dysfunction: The Role of Poly(ADP-Ribose) Polymerase Activation," *Nature Medicine* 7(1):108-113.

Sorlie, T. et al. (Jul. 8, 2003). "Repeated Observation of Breast Tumor Subtypes in Independent Gene Expression Data Sets," *Proc. Natl. Acad. Sci. USA* 100(14):8418-8423. Epub Jun. 26, 2003.

Stephenson, C. F. et al. (Nov. 1992). "Cytogenetic and Pathologic Aspects of Ewing's Sarcoma and Neuroectodermal Tumors," *Hum. Pathol.* 23(11):1270-1277.

Stryer, L. (1981). *Biochemistry*, Second Edition, W.H. Freeman and Company: San Francisco, CA, Part II, Chapter 15 entitled "Pentose Phosphate Pathway and Glucogenesis," pp. 343-345.

Sutton, G. P. et al. (Aug. 1989). "Phase II Trial of Ifosfamide and Mesna in Mixed Mesodermal Tumors of the Uterus, (A Gynecologic Oncology Group Study)." *Am. J. Obstet. Gynecol.* 161 (2):309-312.

Sutton, G. et al. (Nov. 2000). "A Phase III Trial of Ifosfamide With or Without Cisplatin in Carcinosarcoma of the Uterus, A Gynecologic Oncology Group Study," *Gynecologic Oncology* 79(2):147-153, and comment in Gynecol. Oncol. (Nov. 2000) 79(2)145-146.

Suzuki, S. et al. (Oct. 1, 2000). "An Approach to Analysis of Large-Scale Correlations Between Genome Changes and Clinical Endpoints in Ovarian Cancer," *Cancer Research* 60(19):5382-5385.

Szabó, C. et al. (1997). "Regulation of Components of the Inflammatory Response by 5-Iodo-6-Amino-1,2Benzopyrone, an Inhibitor of Poly(ADP-Ribose) Synthetase and Pleiotropic Modifier of Cellular Signal Pathways," *International Journal of Oncology* 10(6):1093-1101.

Taetle, R. et al. (Jul. 1999). "Chromosome Abnormalities Adenocarcinoma: I. Nonrandom Chromosome Abnormalities from 244 Cases," *Genes Chromosomes Cancer* 25(3):290-300.

Tanner, M. M. et al. (May 2000). "Frequent Amplification of Chromosomal Region 20q12-q13 in Ovarian Cancer," *Clin. Cancer Research* 6(5):1833-1839.

Taruscio, D. et al. (Jun. 1993). "Detection of Trisomy 12 on Ovarian Sex Cord Stromal Tumors by Fluorescence in Situ Hybridization," *Diagn. Mol. Pathol.* 2(2):94-98.

Thigpen, J. T. et al. (Feb. 1986). "Phase II Trial of Cisplatin in the Treatment of Patients with Advanced or Recurrent Mixed Mesodermal Sarcomas of the Uterus: A Gynecologic Oncology Group Study," *Cancer Treatment Reports* 70(2):271-274.

Thigpen, J. T. et al. (Oct. 1, 2004). "Phase III Trial of Doxorubicin With or Without Cisplatin in Advanced Endometrial Carcinoma: A Gynecologic Oncology Group Study," *J. Clin. Oncol.* 22(19):3902-3908.

Thomas, H. D. et al. (2007). "Preclinical Selection of a Novel Poly(ADP-Ribose) Polymerase Inhibitor for Clinical Trial," *Mol. Cancer Ther.* 6(3):945-956.

Thompson, F. H. et al. (Mar. 1994). "Clonal Chromosome Abnormalities in 54 Cases of Ovarian Carcinoma," *Cancer Genet. Cytogenet.* 73(1):33-45.

Turc-Carel, C. et al. (Jun. 1988). "Chromosomes in Ewing's Sarcoma. I. An Evaluation of 85 Cases of Remarkable Consistency of t(11;22)(q24;q12)," *Cancer Genet. Cytogenet.* 32(2):229-238.

Virag, L. et al. (1999). "Inhibition of Poly(ADP-Ribose) Synthetase (PARS) and Protection Against Peroxynitrite-Induced Cytotoxicity by Zinc Chelation," *Br. J. Pharmacol.* 126:769-777.

Virag, L. (1999). "Requirement of Intracellular Calcium Mobilization for Peroxynitrite-Induced Poly(ADP-Ribose) Synthetase Activation and Cytotoxicity," *Mol. Pharmacol.* 56:824-833.

Virag, L. et al. (2001). "Purines Inhibit Poly(ADP-Ribose) Polymerase Activation and Modulate Oxidant-Induced Cell Death," *FASEB J.* 15:99-107.

Virag, L. et al. (2002). "The Therapeutic Potential of Poly(ADP-Ribose) Polymerase Inhibitors," *Pharmacol Rev.* 54(3):375-429.

Wang, Z. Q. et al. (1995). "Mice Lacking ADPRT and Poly(ADP-Ribosyl)ation Develop Normally but are Susceptible to Skin Disease," *Genes Dev.* 9:509-520.

Wang, Z.-Q. et al. (Sep. 15, 1997). "PARP is Important for Genomic Stability but Dispensable in Apoptosis," *Genes Dev.* 11(18):2347-2358.

Wasserman, E. J. et al. (2008). "Evolving Strategies for the Treatment of 'Triple-Negative' Breast Cancer," *American Society of Clinical Oncology Educational Book*, pp. 120-126.

Watson, C. Y. et al. (1998). "Synthesis of 3-Substituted Benzamides and 5-Substituted Isoquinolin- 1(2H)-ones and Preliminary Evaluation as Inhibitors of Poly(ADP-Ribose)Polymerase (PARP)," *Bioorg Med Chem.* 6:721-734.

Weisner, R. J. et al. (Aug. 1992). "Detection of Rare mRNAs via Quantitative RT-PCR," *Trends Genet.* 8(8):263-264.

White, A. W. et al. (2000). "Resistance-Modifying Agents. 9. Synthesis and Biological Properties of Benzimidazole Inhibitors of the DNA Repair Enzyme Poly(ADP-Ribose) Polymerase," *J. Med. Chem.* 43:4084-4097.

Winer, E. P. et al. (2007). "Optimizing Treatment of 'Triple-Negative' Breast Cancer," $30_{th}$ *Annual San Antonio Breast Cancer Symposium, selection from SABCS 2007: Improving Outcomes in Advanced and Metastatic Breast Cancer*, 4 pages total.

Yalcintepe, L. et al. (Mar. 2005). "Changes in NAD/ADP-Ribose Metabolism in Rectal Cancer," *Braz. J. Med. Biol. Res.* 38(3):361-365 (article in English).

Yang-Feng, T. L. et al. (Jul. 9, 1991). "Trisomy 12 and K-ras-2-Amplification in Human Ovarian Tumors," *Int. J. Cancer* 48(5):678-681.

Yanochko, G. M. et al. (Apr. 3, 2006). "Type I Insulin-Like Growth Factor Receptor Over-Expression Induces Proliferation and Anti-Apoptotic Signaling in a Three-Dimensional Culture Model of Breast Epithelial Cells," *Breast Cancer Res.* 8(2):R18, pp. 1-13.

Yoshida, S. et al. (Jan. 1991). "Production of 2-Methyl-4[3H]-Quinazolinone, an Inhibitor of Poly(ADP-Ribose) Synthetase, by Bacterium," *The Journal of Antibiotics* (Tokyo), 44(1):111-112.

Zabarovsky, E. R. et al. (Oct. 7, 2002). "Tumor Suppressor Genes on Chromosome 3p Involved in the Pathogenesis of Lung and Other Cancers," *Oncogene* 21(45):6915-6935.

Zhang, J. et al. (Nov. 30, 2000). "GPI 6150 Prevents $H_2O_2$ Cytotoxicity by Inhibiting Poly(ADP-Ribose) Polymerase," *Biochem. Biophys. Res. Comm.* 278(3):590-598.

Declaration of Non-Establishment of International Search Report mailed on May 13, 2009, for PCT Patent Application No. PCT/US2008/012757 filed on Nov. 12, 2008, for Sherman et al., 1 page.

Declaration of Non-Establishment of International Search Report mailed on Jun. 1, 2009, for PCT Patent Application No. PCT/US2008/083147 filed on Nov. 11, 2008, for Sherman et al., 1 page.

International Search Report mailed on Dec. 3, 2007, for PCT Application No. PCT/US07/71053 filed on Jun. 12, 2007, 1 page.

International Search Report mailed on Oct. 16, 2007, for PCT Application No. PCT/US06/27907 filed on Jul. 18, 2006, 1 page.

International Search Report mailed on Jun. 16, 2008, for PCT Application No. PCT/US07/77651 filed on Sep. 5, 2007, 1 page.

International Search Report mailed on Feb. 13, 2009, for PCT Application No. PCT/US08/85756 filed on Dec. 5, 2008, 1 page.

Written Opinion of the International Search Report Authority mailed on Oct. 16, 2007, for PCT Application No. PCT/US06/27907 filed on Jul. 18, 2006, 3 pages.

U.S. Appl. No. 12/496,593, filed Jul. 1, 2009, for Sherman et al.

U.S. Appl. No. 12/502,943, filed Jul. 14, 2009, for Sherman et al.

Bangham, A.D., et al. Diffusion of univalent ions across the lamellae of swollen phospholipids. J. Mol. Biol. 1965; 13: 238-252.

Chen, et al. Potential for selective modulation of glutathione in cancer chemotherapy. Chem Biol Interact. 1998; 111-112:263-75.

De Murcia, et al. Poly(ADP-ribose) polymerase: a molecular nick-sensor. Trends Biochem Sci. 1994; 19:172-176.

Desmarais, et al. Enzymological properties of poly(ADP-ribose)polymerase: characterization of automodification sites and NADase activity. Biochim. Biophys. Acta. 1991; 1078: 197-186.

El-Khamisy, et al. A requirement for PARP-1 for the assembly or stability of XRCC1 nuclear foci at sites of oxidative DNA damage. Nucleic Acid Res. 2003; 31(19): 5526-5533.

Fojo, et al. Amplification of DNA sequences in human multidrug-resistant KB carcinoma cells. Proc Natl Acad Sci U S A. 1985; 82(22):7661-5.

Goodman, et al. Eds. The Pharmacological Basic of Therapeutics. 11th ed. Brunton, et al. eds. McGraw-Hall. New York. 2006.

Gradwohl, et al. The second zinc-finger domain of poly(ADP-ribose) polymerase determines specificity for single-stranded breaks in DNA. Proc. Natl. Acad. Sci. USA 1990; 87:2990-2994.

Jaboin, et al. MS-27-275, an inhibitor of histone deacetylase, has marked in vitro and in vivo antitumor activity against pediatric solid tumors. Cancer Research. 2002; 62:6108-6115.

Kerley-Hamilton, et al. A p53-dominant transcriptional response to cisplatin in testicular germ cell tumor-derived human embryonal carcinoma. Oncogene 2005; 24:6090-6100.

Masson, et al. XRCC1 is specifically associated with poly(ADP-ribose) polymerase and negatively regulates its activity following DNA damage. Mol Cell Biol. 1998; 18(6):3563-3571.

Masutani, et al. Poly(ADP-ribose) and carcinogenesis. Genes, Chromosomes, and Cancer. 2003; 6: 339-348.

Mendeleyev, et al. Potential chemotherapeutic activity of 4-iodo-3-nitrobenzamide. Metabolic reduction to the 3-nitroso derivative and induction of cell death in tumor cells in culture. Biochem Pharmacol. 1995; 50(5):705-714.

O'Brien, et al. Investigation of the Alamar Blue (resazurin) fluorescent dye for the assessment of mammalian cell cytotoxicity. Eur J Biochem. 2000; 267(17):5421-6.

Okano, et al. Spatial and temporal cellular responses to single-strand breaks in human cells. Mol Cell Biol. 2003; 23(11): 3974-3981.

Park, et al. Induction of apoptosis and inhibition of cyclooxygenase-2 expression by N-methyl-N'-nitro-N-nitrosoguanidine in human leukemia cells. Anti-Cancer Drugs. 2005; 16(5):507-13.

Remington's Pharmaceutical Sciences. Latest edition. Mack Publishing Co. Easton, P.

Rice, et al. Induction of Endonuclease-Mediated Apoptosis in Tumor Cells by C-Nitroso- Substituted Ligands of Poly(ADP-Ribose) Polymerase. Proceedings of the National Academy of Sciences. 1992; 89:7703-7707.

Ruscetti, et al. Stimulation of the DNA-dependent protein kinase by poly(ADP-ribose) polymerase. J. Biol. Chem. 1998; 273; 14461-14467.

Saito, et al. A synthetic inhibitor of histone deacetylase, MS-27-275, with marked in vivo antitumor activity against human tumors. Proc. National Acad. Sci. 1999; 96:4592-4597.

Shall, et al. Poly(ADP-ribose) polymerase-1: what have we learned from the deficient mouse model? Mutat Res. 2000; 460(1):1-15.

Shen, et al. Multiple drug-resistant human KB carcinoma cells independently selected for high-level resistance to colchicine, adriarnycin, or vinblastine show changes in expression of specific proteins. J Biol Chem. Jun. 15, 1986;261(17):7762-70.

Simonin, et al. The carboxyl-terminal domain of human poly(ADP-ribose) polymerase. Overproduction in *Escherichia coli*, large scale purification, and characterization. J. Biol. Chem. 1993; 268: 13454-13461.

Szoka, et al. Procedure for preparation of liposomes with large internal aqueous space and high capture by reverse-phase evaporation. Proc. Nat'l Acad. Sci. 1978; 75(9): 4194-4198.

Anders, C. et al. (Oct. 2008). "Understanding and Treating Triple-Negative Breast Cancer," *Oncology* 22(11):1233-1243.

Andersen, B. et al. (Oct. 15, 2002). "The Effect of Glucose on the Potency of Two Distinct Glycogen Phosphorylase Inhibitors," *Biochem. J.* 367(Pt 2):443-450.

Balakumar, P. et al. (2006). "Effect of 3-Aminobenzamide, an Inhibitor of Poly(ADP-Ribose) Polymerase in Experimental Cardiac Hypertrophy," *Int. J. Pharmacol.* 2(5):543-548.

Blakeley, J. O. et al. (Jun. 5, 2010). "Poly (ADP-ribose) Polymerase-1 (PARP1) Inhibitor BSI-201 in Combination with Temozolomide (TMZ) in Malignant Glioma," *J. Clinical Oncol.* 28:15s, Abstact No. 2012, located at http:abstract.asco.org/AbstView__74__49865.html, 3 pages.

Boros, L. G. et al. (Mar. 6, 2002). "Metabolic Profiling of Cell Growth and Death in Cancer: Applications in Drug Discovery," *Drug Discovery Today* 7(6):364-372.

Bowman, K. J. et al. (Jan. 5, 2001). "Differential Effects of the Poly(ADP-Ribose) Polymerase (PARP) Inhibitor NU1025 on Topoisomerase I and II Inhibitor Cytotoxicity in L1210 Cells in Vitro," *Br. J. Cancer* 84(1):106-112.

Bryant, H.E. et al. (2004). "Poly(ADP-ribose) Polymerase Inhibitors as Potential Chemotherapeutic Agents," *Biochemical Society Transactions* 32(6):959-961.

Cancer.Org (2005). "What is Ovarian Cancer?" available online as of Feb. 5, 2005 as evidenced by the attached Internet Archive Report located at http://www.cancer.org/docroot/CRI/content/CRI_2_4_1X__What__is__ovarian__cancer__33.asp, 6 pages total.

Carey, L.A. (Sep. 3, 2010). "Directed Therapy of Subtypes of Triple Negative Breast Cancer," *The Oncologist* 15(Supplement 3 Preview):8-15.

Castro, M. et al. (2010). "Pharmacokinetics of BSI-201, a Poly (ADP-ribose) Polymerase-1 (PARP1) Inhibitor, in Cerebrospinal Fluid (CSF) of a Patient with Breast Cancer with Carcinomatous Meningitits," *J. Clin. Oncol.* 28-Supplemental, Abstrct No. e13559, 2 pages.

Comin-Anduix, B. et al. (Aug. 2001). "The Effect of Thiamine Supplementation on Tumour Proliferation. A Metabolic Control Analysis Study," *Eur. J. Biochem.* 268(15):4177-4182.

Curtin, N. J. (Mar. 15, 2005). "PARP Inhibitors for Cancer Therapy," *Expert. Rev. Mol. Med.* 7(4):1-20.

Delaney, C. A. et al. (Jul. 2000). "Potentiation of Temozolomide and Topotecan Growth Inhibition and Cytotoxicity by Novel Poly(Adenosine Diphosphoribose) Polymerase Inhibitors in a Panel of Human Tumor Cell Lines," *Clin. Cancer Res.* 6(7):2860-2867.

Fedier, A. et al. (May 2003). "The Effect of Loss of BRCA1 on the Sensitivity to Anticancer Agents in p53-Deficient Cells," *Int. J. Oncol.* 22(5):1169-1173, Abstract only located in PubMed, 1 page.

Goodman et al. (1996). *The Pharmacological Basis of Therapeutic*, 9th Edition, pp. 1225-1232, 1269-1271.

Herzog, T. J. (2002). "Update on the Role of Topotecan in the Treatment of Recurrent Ovarian Cancer," *Oncologist* 7(suppl. 5):3-10.

Hirai, K. et al. (Jul. 1983). "Aberration of Poly(Adenosine Diphosphate-Ribose) Metabolism in Human Colon Adenomatous Polyps and Cancers," *Cancer Research* 43:3441-3446.

Kang, S.P. et al. (Feb. 2008). "Triple Negative Breast Cancer: Current Understanding of Biology and Treatment Options," *Curr. Opin. Obstet. Gynecol.* 20(1):40-46.

Khan, Z A et al. (2006). "Therapeutic Targeting of Endothelial Dysfunction in Chromic Diabetic Complications," *Recent Patents in Cardiovascular Drug Discovery* 1:167-175.

Kopetz, S. et al. (May 20, 2008). "First Human Phase I Study of BSI-201, a Small Molecule Inhibitor of Poly ADP-ribose Polymerase (PARP) in Subjects with Advanced Solid Tumors," *J. Clin. Oncol* 26(Supplemental), Abstract No. 3577, 3 pages.

Kuhajda, F. P. et al. (Jul. 5, 1994). "Fatty Acid Synthesis: A Potential Selective Target for Antineoplastic Therapy," *Proc. Nat'l. Acad. Sci USA* 91(14):6379-6383.

Kuhajda, F. P. et al. (Mar. 28, 2000). "Synthesis and Antitumor Activity of an Inhibitor of Fatty Acid Synthase," *Proc. Nat'l. Acad. Sci USA* 97(7):3450-3454.

Lee, W.-N. et al. (Mar. 20, 1995). "Isotopomer Study of Lipogenesis in Human Hepatoma Cells in Culture: Contribution of Carbon and Hydrogen Atoms from Glucose," *Anal. Biochem.* 226(1):00-112.

Lee, W.-N. et al. (Sep.-Dec. 1996). "Mass Isotopomer Study of Glutamine Oxidation and Synthesis in Primary Culture of Astrocytes," *Dev. Neurosci.* 18(5-6):469-477.

Lee, W.-N. et al. (May 1998). "Mass Isotopomer Study of the Nonoxidative Pathways of the Pentose Cycle with [1,2-$^{13}C_2$] Glucose," *Am. J. Physiol. Endocrinol. Metab.* 274(5 Pt 1):E843-E851.

Lee, W.-N. et al. (Aug. 14, 1998). "Fatty Acid Cycling in Human Hepatoma Cells and the Effects of Troglitazone," *J. Biol. Chem.* 273(33):20929-20934.

Leimer, K. R. et al. (Aug. 21, 1977). "Complete Mass Spectra of N-Trifluoroacetyl-n-Butyl Esters of Amino Acids," *J. Chromatography* 141(2):121-144.

Loftus, T. M. et al. (Jun. 30, 2000). "Reduced Food Intake and Body Weight in Mice Treated with Fatty Acid Synthase Inhibitors," *Science* 288(5475):2379-2381.

Mahaney, J.J. et al. (May 20, 2008). "A Phase IB Study Evaluating BSI-201 in Combination with Chemotherapy in Subjects with Advanced Solid Tumours," *J. Clin. Oncol.* 26(Supplemental), Abstract No. 3579, 3 pages.

Martin, S.A. et al. (Feb. 2008, e-pub. Mar. 14, 2008). "DNA Repair Deficiency as a Therapeutic Target in Cancer," *Curr. Opin. Genet. Dev.* 18(1):80-86.

Melisi, D. et al. (Oct. 2007). "The Novel Poly(ADP-ribose) Polymerase (PARP)-1 Inhibitor, BSI-401, has Antitumor Activity and Potentiates Oxaliplatin Cytotoxic Activity in Human Pancreatic Cancer," *AACR-NCI-EORTC International Conference: Molecular Targets and Cancer Therapeutics,* San Francisco, CA, Oct. 22-26, 2007, Abstract B282, located at <http://www.aacrmeetingabstracts.org/cgi/content/meeting_abstract/2007/3_Molecular_Targets_Meeting/B282?maxtoshow=&HITS=10&hits=10&RESULTFORMAT=&author1=melisi&andor exactfulltext=and&searchid=1&FIRSTINDEX=0&sortspec=relevance&resourcetype=HWCIT>, last visited on Jul. 15, 2010, 2 pages.

Melisi, D. et al. (Jan. 2009). "Antitumour Efficacy of the Novel Poly(ADP-Ribose) Polymerase (PARP-1) Inhibitor BSI-401 and Synergism with Oxaliplatin (OX) in an Orthotopic Murine Model of Pancreatic Cancer (PCc)," *2009 Gastrointestinal Cancers Symposium,* located at <http://www.asco.org/ASCOv2/Meetings/Abstracts?&vmview=abst_detail_pl view&confID=63&abstractID=10481>, last visited on Jul. 12, 2010, Abstract No. 164, 4 pages.

Menendez, J. A. et al. (Apr. 1, 2005). "Does Endogenous Fatty Acid Metabolism Allow Cancer Cells to Sense Hypoxia and Mediate Hypoxic Vasodilation? Characterization of a Novel Molecular Connection Between Fatty Acid Synthase (FAS) and Hypoxia-Inducible Factor-1α (HIF-1α)-Related Expression of Vascular Endothelial Growth Factor (VEGF) in Cancer Cells Overexpressing Her-2/neu Oncogene," *J. Cell Biochem* 94(5):857-863.

Menendez, J. A. et al. (Jul./Aug. 2005). "Targeting Fatty Acid Synthase: Potential for Therapeutic Intervention in Her-2/neu-Overexpressing Breast Cancer," *Drug News & Perspective* 18(6):375-385.

O'Shaughnessy, J. et al. (Dec. 12, 2008). "Triple Negative Breast Cancer: A Phase 2, Multi-center, Open-label, Randomized Trial of Gemcitabine/Carboplatin (G/C), with or without BSI-201, a PARP Inhibitor," *San Antonio Breast Cancer Symposium Annual Meeting 2008,* San Antonio, Tx, located at <http://www.abstracts2view.com/sabcs/view.php?nu=SABCSO8L_612&terms=>, last visited on Jul. 12, 2010, 1 page.

O'Shaughnessy, J. et al. (2009). "Efficacy of BSI-201, A Poly (ADP-ribose) Polymerase-1 (PARP1) Inhibitor, in Combination with Gemcitabine/Carboplatin (G/C) in Patients with Metastatic Triple-Negative Breast Cancer (TNBC): Results of a Randomized Phase II Trial," *J. Clint. Oncol.* 27:182, Abstract No. 3, 4 pages.

O'Shaughnessy, J. et al. (Dec. 11, 2009). "Updated Results of a Randomized Phase II Study Demonstrating Efficacy and Safety fo BSI-201, A PARP Inhibitor, in Combination with Gemcitabine/Carboplatin in Metastatic Triple-Negative Breast Cancer," *San Antonio Breast Cancer Symposium,* San Antonio, Texas, Dec. 9-13, 2009, located at <http://www.posters2view.com/sabcs09/viewp.php?nu=3122>, last visited on Jul. 12, 2010, 1 page.

O'Shaughnessy, J. (2010). "Triple Negative Breast Cancer: The Emerging Treatment with BSI-201 (Iniparib)," *The Oncologist* 15(Supplement 3 Preview):1-7.

Ossvskaya, V. et al. (Oct. 2007). "PARP1 Gene Over-expression in Primary Human Cancers: A Potential Marker for PARP Inhibition," *AACR-NCI-EORTC International Conference: Molecular Targets and Cancer Therapeutics,* San Francisco, CA, Oct. 22-26, 2007, located at <http://www.aacrmeetingabstracts.org/cgi/content/meeting_abstract/2007/3_Molecular_Targets_Meeting/C125?maxtoshow=&HITS=10&hits=10&RESULTSFORMAT=&fulltext=bsi201&andorexactfulltext=and&searchid=1&FIRSTINDEX=0&sortspec=relevance&resourcetype =HWCIT>, last visited on Jul. 15, 2010, Abstract C125, 2 pages.

Ossovskaya, V. et al. (Nov. 2007). "The PARP1 Gene is Over-expressed in Triple Neagtive Breast Cancer," *European Journal of Cancer Supplements* 5(8):31, Abstract P57.

Ossovskaya, V. et al. (Apr. 2008). "Activity of BSI-201, a Potent Poly(ADP-ribose) Polymerase (PARP1) Inhibitor, Alone and in Combination with Topotecan in Human Ovarian Xenografts," *99th AACR Annual Meeting,* San Diego, CA, Apr. 12-16, 2008, Abstract No. 2311 located at <http://www.aacrmeetingabstracts.org/cgi/content/meeting_abstract/2008/1_Annual_Meeting/2311?maxtoshow=&HITS=10&hits=10&RESULTFORMAT=Mulltext=bsi201&andorexactfulltext=and&searchid=1&FIRSTINDEX=0&sortspec=relevance&resourcetype =HWCIT>, last visited on Jul. 15, 2010, 2 pages.

Ossovskaya, V. et al. (Apr. 22, 2009). "BSI-201 Enhances the Activity of Multiple Classes of Cytotoxic Agents and Irradiation in Triple Negative Breast Cancer," *2009 AACR Annual Meeting,* Denver, CO, Apr. 18-22, 2009, located at <http://www.abstractsonline.com/viewer/viewAbstractasp?CKey=%7BA98A01B0-1623-4F71-99C7-FCE19F299C1F% /07D&MKey=%/07BD007B270-E8F6-492D-803B-7582CE7A0988%07D&AKey=°/07B728BCE9C-121B-46B9-A8EE-DC51FDFC6C15°/07D&SKey=%07BCCA05FCE-642E-4E26-AD12-29C831335BE1%7D>, last visited on Jul. 12, 2010, 2 pages.

Pizer, E. S. et al. (Jun. 15, 1996). "Inhibition of Fatty Acid Synthesis Induces Programmed Cell Death in Human Breast Cancer Cells," *Cancer Res.* 56(12):2745-2747.

Powell, S. N. et al. (Sep. 1, 2003). "Roles of BRCA1 and BRCA2 in Homologous Recombination, DNA Replication Fidelity and the Cellular Response in Ionizing Radiation," *Oncogene* 22(37):5784-5791.

Rodon, J. et al. (Jan. 2009). "Development of PARP Inhibitors in Oncology," *Expert Opin. Investig. Drugs* 18(1):31-43.

Sabate, L. et al. (Jan. 12, 1995). "A Model of the Pentose Phosphate Pathway in Rat Liver Cells," *Mol. Cell Biochem.* 142(1):9-17.

Sestili, P. et al. (1990). "Structural Requirements for Inhibitors of Poly(ADP-ribose) Polymerase," *J. Cancer. Res. Clin. Oncol.* 116:615-622.

Shiu, K.K. et al. (Sep. 2008). "Development of Therapeutic Approaches to 'Triple Negative' Phenotype Breast Cancer," *Expert Opin. Ther. Targets* 12(9):1123-1137.

Woodhouse, B.C. et al. (Jul. 1, 2008, e-pub. May 12, 2008). "Poly ADP-ribose Polymerase-1: An International Molecule of Mystery," *DNA Repair (Amst.)* 7(7):1077-1076.

Zingarelli, B. et al. (1997). "Protection Against Myocardial lschemia and Reperfusion Injury by 3-Aminobenzamide, an Inhibitor of Poly (ADP-ribose) Synthetase," *Cardiovascular Research* 36:205-215.

Written Opinion of the International Search Authority mailed on Jun. 16, 2008, for PCT Application No. PCT/US07/77651 filed on Sep. 5, 2007, 4 pages.

International Search Report mailed on Jun. 18, 2008, for PCT Patent Application No. PCT/US07/77662 filed on Sep. 5, 2007, published on Mar. 13, 2008, for PCT Publication No. WO 2008/30891, 1 page.

Written Opinion mailed on Jun. 18, 2008, for PCT Patent Application No. PCT/US07/77662 filed on Sep. 5, 2007, published on Mar. 13, 2008, for PCT Publication No. WO 2008/30891, 4 pages.

Written Opinion of the International Search Authority mailed on Dec. 3, 2007, for PCT Application No. PCT/US07/71053 filed on Jun. 12, 2007, 5 pages.

Written Opinion mailed on Feb. 13, 2009, for PCT Application No. PCT/US08/85756 filed on Dec. 5, 2008, 4 pages.

International Search Report mailed on Sep. 10, 2009, for PCT Patent Application No. PCT/US09/033117, filed on Feb. 4, 2009, 3 pages.

Written Opinion mailed on Sep. 10, 2009, for PCT Patent Application No. PCT/US09/0331 17, filed on Feb. 4, 2009, 4 pages.

International Search Report mailed on Mar. 23, 2010, for PCT Patent Application No. PCT/US2010/023137 filed on Feb. 4, 2010, published on Aug. 12, 2010, as PCT Publication No. WO 2010/091140, 1 page.

Written Opinion mailed on Mar. 23, 2010, for PCT Patent Application No. PCT/US2010/023137 filed on Feb. 4, 2010, published on Aug. 12, 2010, as PCT Publication No. WO 2010/091140, 5 pages.
Supplementary European Search Report mailed on Jul. 6, 2010, for EP Patent Application No. 07841902.5, filed on Sep. 5, 2007, 5 pages.
Supplementary European Search Report mailed on Jul. 8, 2010, for EP Patent Application No. 07875034.6, filed on Jun. 12, 2007, 14 pages.
Non Final Office Action mailed on Jul. 30, 2010, for U.S. Appl. No. 12/165,437, filed on Jun. 30, 2008, 10 pages.
Non Final Office Action mailed on Aug. 11, 2009, for U.S. Appl. No. 12/269,024, filed on Nov. 11, 2008, 13 pages.
Non Final Office Action mailed on Mar. 4, 2010, for U.S. Appl. No. 12/269,833, filed Nov. 12, 2008., 77 pages.
International Preliminary Report on Patentability mailed on Jun. 17, 2010, for PCT Application No. PCT/US08/085756 filed on Dec. 5, 2008, 6 pages.
U.S. Appl. No. 12/748,209 filed Mar. 26, 2010, for Ossovskaya et al.
Bakke, J. E. et al. (Jan. 1, 1988). "Metabolism of 2,6-Dichlorobenzamide in Rats and Mice," *Xenobiotica* 18(7):817-829.
Balendiran, G. K. et al. (Jan. 1, 2004). "The Role of Glutathione in Cancer," *Cell Biochemistry and Function* 22:343-352.
Behrens, P. et al. (2001). "Invasive Properties of Serous Human Epithelial Ovarian Tumors are Related to Ets-1, MMP-1 and MMP-9 Expression," *Int. J. Mol. Med.* 8:149-154.
Behrens, P. et al. (2001). "The Ets-1 Transcription Factor is Up-Regulated Together with Mmp 1 and Mmp 9 in the Stroma of Pre-Invasive Breast Cancer," *J. Pathol.* 194:43-50.
Bischoff, J. R. et al. (Nov. 1999). "The Aurora/Ipl1p Kinase Family: Regulators of Chromosome Segregation and Cytokinesis," *Trends Cell Biol.* 9:454-459.
Blakeley, J. O. et al. (Jun. 5, 2010). "Poly (ADP-ribose) Polymerase-1 (PARP1) Inhibitor BSI-201 in Combination with Temozolomide (TMZ) in Malignant Gilmoa," *J. Clin. Oncol.* 28(15)(May 20 Supplement):2012, also located at *ASCO Annual Meeting Proceedings* (Post-Meeting Edition) located at http://meeting.ascopubs.org/cgi/content/abstract/28/15_suppl/2012, 3 pages.
Bohula, E. A. et al. (Oct. 2003). "Targeting the Type 1 Insulin-like Growth Factor Receptor as Anti-Cancer Treatment," *Anti-Cancer Drugs* 14(9):669-682.
Bold, R. J. et al. (Sep. 2001). "Chemosensitization of Pancreatic Cancer by Inhibition of the 26S Proteasome," *J. Surg. Res.* 100(1):11-17.
Canova-Davis, E. et al. (Feb. 1976). "Chemical Modification of the Tryptophan Residue in Adrenocorticotropin," *Biochem.* 15(4):921-927.
Chang, W. et al. (Dec. 14, 2001). "The Sequence-specific DNA Binding of NF-$_K$B is Reversibly Regulated by the Automodification Reaction of Poly (ADP-ribose) Polymerase 1," *J. Biol. Chem.* 276(50):47664-47670.
Clinical Trial Registry NCT 00298675 (Mar. 2006). "Phase 1/1b Dose Escalation Study Evaluating BSI-201 as a Single Agent and in Combination With Irinotecan in Subjects With Advanced Solid Tumors," located at http://clinicaltrials.gov/ct2/show/NCT00298675, last visited on Oct. 27, 2010, first received on Mar. 1, 2006; last updated on Jun. 14, 2010, 5 pages.
Clinical Trial Registry NCT 00422682 (Jan. 2007). "A Study Evaluating BSI-201 in Combination With Chemotherapeutic Regimens in Subjects With Advanced Solid Tumors," located at http://clinicaltrials.gov/ct2/show/NCT00422682, last visited on Oct. 27, 2010, first received on Jan. 12, 2007, last updated on Jun. 14, 2010, 6 pages.
Clinical Trial Registry NCT 00540358 (Oct. 2007). "A Phase 2 Trial of Standard Chemotherapy, With or Without BSI-201, in Patients With Triple Negative Metastatic Breast Cancer," located at http://clinicaltrials.gov/ct2/show/NCT00540358, last visited on Oct. 27, 2010, first received on Oct. 4, 2007, last updated on Jun. 14, 2010, 7 pages.
Clinical Trial Registry NCT 00687765 (May 2008). "Study of the Poly (ADP-ribose) Polymerase-1 (PARP-1) Inhibitor BSI-201 in Patients With Newly Diagnosed Malignant Glioma," located at http://clinicaltrials.gov/ct2/show/NCT00687765, last visited on Oct. 27, 2010, first received on May 28, 2008, last updated on Jun. 14, 2010, 6 pages.

Clinical Trial Registry NctCT 00687687 (May 2008). "Evaluation of Paclitaxel (Taxol, NSC #673089), Carboplatin (Paraplatin, NSC #241240), and BSI-201 (NSC #746045, IND #71,677) in the Treatment of Advanced, Persistent, or Recurrent Uterine Carcinosarcoma," located at http://clinicaltrials.gov/ct2/show/NCT00687687, last visited on Oct. 27, 2010, first received on May 28, 2008, last updated on Jun. 14, 2010, 5 pages.
Clinical Trial Registry NCT 00677079 (May 2008). "Single Arm Study of BSI-201 in Patients With BRCA-1 or BRCA-2 Associated Advanced Epithelial Ovarian, Fallopian Tube, or Primary Peritoneal Cancer," located at http://clinicaltrials.gov/ct2/show/NCT00677079, last visited on Oct. 27, 2010, first received on May 9, 2008, last updated on Jun. 14, 2010, 5 pages.
Clinical Trial Registry NCT 00813956 (Dec. 2008). "A Phase 2 Study of Standard Chemotherapy Plus BSI-201 (a PARP Inhibitor) in the Neoadjuvant Treatment of Triple Negative Breast Cancer," located at http://clinicaltrials.govict2/show/NCT00813956, last visited on Oct. 27, 2010, first received on Dec. 19, 2008, last updated on Jun. 14, 2010, 5 pages.
Clinical Trial Registry NCT 00938652 (Jul. 10, 2009). "A Phase 3, Multi-Center Study of Gemcitabine/Carboplatin, With or Without BSI-201, in Patients With ER-, PR-, and Her2- Negative Metastatic Breast Cancer," located at http://clinicaltrials.gov/ct2/show/NCT00938652, last visited on Oct. 27, 2010, first received on Jul. 10, 2009, last updated on Jun. 14, 2010, 7 pages.
Clinical Trial Registry NCT 01033292 (Dec. 2009). "A Single-Arm Study Evaluating Carboplatin/Gemcitabine in Combination With BSI-201 in Patients With Platinum-Resistant Recurrent Ovarian Cancer," located at http://clinicaltrials.gov/ct2/show/NCT01033292, last visited on Oct. 27, 2010, first received on Dec. 14, 2009, last updated on Jun. 14, 2010, 6 pages.
Clinical Trial Registry NCT 01033123 (Dec. 2009). "A Single-Arm Study Evaluating Carboplatin/Gemcitabine in Combination With BSI-201 in Patients With Platinum-Sensitive Recurrent Ovarian Cancer," located at http://clinicaltrials.gov/ct2/show/NCT01033123, last visited on Oct. 27, 2010, first received on Dec. 14, 2009, last updated on Jun. 14, 2010, 6 pages.
Clinical Trial Registry NCT 01045304 (Jan. 2010). "Study of SAR240550 (BSI-201) in Combination With Gemcitabine/Carboplatin, in Patients With Metastatic Triple Negative Breast Cancer," located at http://www.clinicaltrials.gov/ct2/show/NCT01045304, last visited on Oct. 27, 2010, first received on Jan. 7, 2010, last updated on Sep. 2, 2010, 7 pages.
Clinical Trial Registry NCT 01082549 (Mar. 2010). "Trial of Gemcitabine/Carboplatin With or Without BSI-201 (a PARP1 Inhibitor) in Patients With Previously Untreated Advanced Squamous Cell Lung Cancer," located at http://clinicaltrials.gov/ct2/show/NCT01082549, last visited on Oct. 27, 2010, first received on Mar. 5, 2010, last updated on Aug. 30, 2010, 7 pages.
Clinical Trial Registry NCT 01130259 (May 2010). "An Open-Label, Expanded Access Protocol of Iniparib Breast Cancer," located at http://clinicaltrials.gov/ct2/show/NCT01130259, last visited on Oct. 27, 2010, first received on May 24, 2010, with no. changes posted, 3 pages.
Clinical Trial Registry NCT 01173497 (Jul. 2010). "A Study Evaluating Iniparib in Combination With Chemotherapy to Treat Triple Negative Breast Cancer Brain Metastasis," http://clinicaltrials.gov/ct2/show/NCT01173497, last visited on Oct. 27, 2010, first received on Jul. 28, 2010, last updated on Jul. 29, 2010; 5 pages.
Clinical Trial Registry NCT 01161836 (Aug. 2010). An Open-label Study Investigating the Disposition and QT/QTc Interval Effects of 400 mg [14C]-Iniparib(3.7 MBq, 100 µCi), located at http://clinicaltrials.gov/ct2/show/NCT01161836, last visited on Oct. 27, 2010, first received on Jul. 12, 2010, last updated on Aug. 20, 2010, 5 pages.
Clinical Trial Registry NCT 01086254 (Oct. 2010). "SAR240550 in Combination With Gemcitabine/Cisplatin in Non-small Cell Lung Cancer," located at http://clinicaltrials.gov/ct2/show/NCT01086254, last visited on Oct. 27, 2010, first received on Mar. 11, 2010, last updated on Aug. 17, 2010, 7 pages.
Cohen-Armon, M. (2007). "PARP-1 Activation in the ERK Signaling Pathway," *Trends Pharmacol. Sci.* 28(11):556-560.

Cory, S. et al. (2003). "The Bcl-2 Family: Roles in Cell Survival and Oncogenesis," *Oncogene* 22:8590-8607.

Cusack, J. C. et al. (May 1, 2001). "Enhanced Chemosensitivity to CPT-11 with Proteasome Inhibitor PS-341: Implications for Systemic Nuclear Factor-$_K$B Inhibition," *Cancer Res.* 61:3535-3540.

Dittmer, J. (Aug. 20, 2003). "The Biology of the Ets1 Proto-Oncogene," *Mol. Cancer,* available at http://www.molecular-cancer.com/content/2/1/29, 2(29):1-21.

Donawho, C. K. et al. (2008). "The PARP Inhibitor, ABT-888 Overcomes Resistance in Temozolomide-Refractory Prostate and Breast Xenograft Tumors Implanted in Metastatic Sites *In Vivo*," Meeting Poster No. 555 (one page), and Palma, J. et al. (Oct. 24, 2008). "The PARP Inhibitor, ABT-888 Overcomes Resistance in Temozolomide-Refractory Prostate and Breast Xenograft Tumors Implanted in Metastatic Sites In Vivo," 20$^{th}$ *EORTC-NCI-AACR, Symposium on Molecular Targets and Cancer Therapeutics, European Journal of Cancer* Supplements 6(12):175, poster No. 555.

Donleavy, J. J. et al. (Jul. 1, 1947). "Alkamine Esters and Amides of Some Amino-Alkylmercaptobenzoic Acids," *J. Amer. Chem. Soc.* 69(7):1781-1784.

Fischer, F. et al. (Dec. 2007). "5-Fluorouracil is Efficiently Removed from DNA by the Base Excision and Mismatch Repair Systems," *Gastroenterology* 133(6):1858-1868.

Gonzalez, R. J. et al. (2001). "Evaluation of Hepatic Subcellular Fractions for Alamar Blue and MTT Reductase Activity," *Toxicol. In Vitro* 15:257-259.

Gotlieb, W. H. et al. (2006). "Insulin-like Growth Factor Receptor I Targeting in Epithelial Ovarian Cancer," *Gynecol. Oncol.* 100:389-396.

Hagan, M. P. et al. (2007). "Radiation-Induced PARP Activation is Enhanced Through EGFR-ERK Signaling," *J. Cell Biochem.* 101:1384-1393.

Hatake, K. et al. (Apr. 2007). "Next Generation Molecular Targeted Agents for Breast Cancer: Focus on EGFR and VEGFR Pathways," *Breast Cancer* 14(2):132-149.

Hideshima, T. et al. (May 10, 2002). "NF-$_K$B as a Therapeutic Target in Multiple Myeloma," *J. Biol. Chem.,* available at http://www.jbc.org (last visited on Aug. 31, 2010), 277(19):16639-16647.

Hutcheson, I. R. et al. (2006). "Inductive Mechanisms Limiting Response to Anti-Epidermal Growth Factor Receptor Therapy," *Endocrine-Rel. Cancer* 13:S89-S97.

Jiang, Y. et al. (Sep. 7, 2001). "Invasiveness of Hepatocellular Carcinoma Cell Lines: Contribution of Hepatocyte Growth Factor, c-met, and Transcription Factor Ets-1," *Biochem. Biophys. Res. Commun.* 286(5):1123-1130.

Jones, H. E. et al. (2006). "Growth Factor Receptor Interplay and Resistance in Cancer," *Endocrine-Rel. Cancer* 13:S45-S51.

Karamouzis, M. V. et al. (Jul. 4, 2007). "Therapies Directed Against Epidermal Growth Factor Receptor in Aerodigestive Carcinomas," *JAMA* 298(1):70-82.

Kari, C. et al. (Jan. 1, 2003). "Targeting the Epidermal Growth Factor Receptor in Cancer: Apoptosis Takes Center Stage," *Cancer Res.* 63:1-5.

Kelly, E. A. B. et al. (2000). "Increased Matrix Metalloproteinase-9 in the Airway After Allergen Challenge," *Am. J. Resp. Crit. Care Med.* 162:1157-1161.

Khandwala, H. M. et al. (2000). "The Effects of Insulin-Like Growth Factors on Tumorigenesis and Neoplastic Growth," *Endo. Rev.* 21(3):215-244.

Kimura, M. et al. (May 23, 1997). "Cell Cycle-dependent Expression and Spindle Pole Localization of a Novel Human Protein Kinase, Aik, Related to Aurora of Drosophila and Yeast Ipl1," *J. Biol. Chem.,* available at http://www.jbc.org (last visited on Sep. 7, 2010), 272(21):13766-13771.

Kitange, G. et al. (Apr. 1999). "Ets-1 Transcription Factor-Mediated Urokinase-Type Plasminogen Activator Expression and Invasion in Glioma Cells Stimulated by Serum and Basic Fibroblast Growth Factors," *Lab. Invest.* 79(4):407-416.

Li, Z. et al. (Jan. 1, 2005). "BCL-6 Negatively Regulates Expression of the NF-$K$B1 p105/p50 Subunit," *J. Immunol.* 174:205-214.

Linardopoulos, S. (Sep. 2007). Aurora-A Kinase Regulates NF-$_K$B Activity: Lessons from Combination Studies, *J. Buon.* 12(Suppl. 1):567-570.

Mabuchi, S. et al. (May 28, 2004). "Inhibition of NF$_K$B Increases the Efficacy of Cisplatin in in Vitro and in Vivo Ovarian Cancer Models," *J. Biol. Chem.,* available at http://www.jbc.org (last visited on Sep. 1, 2010), 279(22):23477-23485.

Makarov, V. et al. (2006). "Synthesis and Antileprosy Activity of Some Dialkyldithiocarbamates," *J. Antimicrob. Chemotherapy* 57:1134-1138.

Mori, N. et al. (Apr. 1, 1999). "Constitutive Activation of NF-$_K$B in Primary Adult T-Cell Leukemia Cells," *Blood* 93(7):2360-2368.

Mori, N. et al. (Sep. 1, 2002). "Bay 11-7082 Inhibits Transcription Factor NF-$_K$B and Induces Apoptosis of HTLV-I-Infected T-cell Lines and Primary Adult T-cell Leukemia Cells," *Blood* 100(5):1828-1834.

Moschos, S. J. et al. (2002). "The Role of the IGF System in Cancer: From Basic to Clinical Studies and Clinical Applications," *Oncology* 63:317-332.

Mrózek, K. et al. (Mar. 1990). "Trisomy of Chromosome 12 in a Case of Thecoma of the Ovary," *Gynecol. Oncol.* 36(3):413-416.

Mugneret, F. et al. (Jun. 1988). "Chromosones in Ewing's Sarcoma. II. Nonrandom Additional Changes, Trisomy 8 and der(16)t(1;16)," *Cancer Genet. Cytogenet.* 32(2):239-245.

Naito, S. et al. (2000). "Overexpression of Ets-1 Transcription Factor in Angiosarcoma of the Skin," *Pathol. Res. Pract.* 196:103-109.

Nakada, M. et al. (Apr. 1999). "Ets-1 Positively Regulates Expression of Urokinase-type Plasminogen Activator (uPA) and Invasiveness of Astrocytic Tumors," *J. Neuropathol. Exp. Neurol.* 58(4):329-334.

O'Shaughnessy, J. et al. (Oct. 2010). Final Efficacy and Safety Results of a Randomized Phase II Study of the PARP Inhibitor Iniparib (BSI-201) in Combination With Gemcitabine/Carboplatin (G/C) in Metastatic Triple Negative Breast Cancer (TNBC), *Annals of Oncology, ESMO* 2010 *Late-Breaking Abstracts, Presidential Symposium,* 21(8): Abstract No. LAB11, p. viii5.

Oda, N. et al. (1999). "Ets-1 Converts Endothelial Cells to the Angiogenic Phenotype by Inducing the Expression of Matrix Metalloproteinases and Integrin $\beta_3$," *J. Cell. Physiol.* 178:121-132.

Oda, K. et al. (2005). "A Comprehensive Pathway Map of Epidermal Growth Factor Receptor Signaling," *Mol. Sys. Biol.* 2005.0010:1-17.

Parker, J. S. et al. (Mar. 10, 2009). "Supervised Risk Predictor of Breast Cancer Based on Intrinsic Subtypes," *J. Clin. Oncol.* 27(8):1160-1167.

Pollak, M. N. et al. (Jul. 2004). "Insulin-like Growth Factors and Neoplasia," *Nature Rev. Cancer* 4(7):505-518.

Prat, A. et al. (2010). "Deconstructing the Molecular Portraits of Breast Cancer," *Molecular Oncology* XXX:1-18 .

Riedemann, J. et al. (2006). "IGF1R Signalling and Its Inhibition," *Endocr. Relat. Cancer* 13:S33-S43.

Roberts, R. B. et al. (Feb. 5, 2002). "Importance of Epidermal Growth Factor Receptor Signaling in Establishment of Adenomas and Maintenance of Carcinomas During Intestinal Tumorigenesis," *PNAS* 99(3):1521-1526.

Rocha-Lima, C. M. et al. (Jul. 2007). "EGFR Targeting of Solid Tumors," *Cancer Control* 14(3):295-304.

Sano, K. et al. (Jan. 1, 2001). "Metabolism of Sulphobromophtalein I: Positional Isomers of Sulphobromophthalein Monoglutathione Conjugate," *J. Pharmacy & Pharmacology* 53:1015-1020.

Santomauro, A. T. M. G. et al. (Sep. 1999). "Overnight Lowering of Free Fatty Acids With Acipimox Improves Insulin Resistance and Glucose Tolerance in Obese Diabetic and Nondiabetic Subjects," *Diabetes* 48:1836-1841.

Sato, Y. et al. (2000). "Signal Transduction and Transcriptional Regulation of Angiogenesis," in *Angiogenesis From the Molecular to Integrative Pharmacology,* Maragoudakis, M.E. ed., Kluwer Academic/Plenum Publishers, New York, NY, 476:109-115.

Sementchenko, V. I. et al. (2000). "Ets Target Genes: Past, Present and Future," *Oncogene* 19:6533-6548.

Sequist, L. V. (2007). "Second-Generation Epidermal Growth Factor Receptor Tyrosine Kinase Inhibitors in Non-Small Cell Lunch Cancer," *Oncologist,* available at http://www.TheOncologist.com (last visited on Sep. 1, 2010), 12:325-330.

Shah, S. A. et al. (2001). "26S Proteasome Inhibition Induces Apoptosis and Limits Growth of Human Pancreatic Cancer," *J. Cell Biochem.* 82:110-122.

Sharrocks, A. D. et al. (1997). "The ETS-domain Transcription Factor Family," *Int. J. Biochem. Cell. Biol.* 29(12):1371-1387.

Sørlie, T. et al. (Sep. 11, 2001). "Gene Expression Patterns of Breast Carcinomas Distinguish Tumor Subclasses with Clinical Implications," *Proc. Natl. Acad. Sci. USA* 98(19):10869-10874.

St-Pierre, Y. et al. (2004). "Regulation of MMP-9 Gene Expression for the Development of Novel Molecular Targets Against Cancer and Inflammatory Diseases," *Expert Opin. Therp. Targets* 8(5):473-489.

Takanami, I. et al. (2001). "Expression of Ets-1 is Correlated with Urokinase-Type Plasminogen Activator and Poor Prognosis in Pulmonary Adenocarcinoma," *Tumor Biol.* 22:205-210.

Tong, Q. et al. (Mar. 2, 2006). "VEGF is Upregulated by Hypoxia-induced Mitogenic Factor via the PI-3K/Akt-NF-$_K$B Signaling Pathway," *Respir. Res.* 7(37):1-14.

Toshi, L. et al. (2007). "Understanding the New Genetics of Responsiveness to Epidermal Growth Factor Receptor Tyrosine Kinase Inhibitors," *Oncologist* 12:211-220.

Tummino, P. J. et al. (Feb. 1, 1997). "The Human Immunodeficiency Virus Type 1 (HIV-1) Nucleocapsid Protein Zinc Ejection Activity of Disulfide Benzamides and Benzisothiazolones: Correlation With Anti-HIV and Virucidal Activities," *Antimicrobial Agents and Chemotherapy* 41(2):394-400.

Wang, T-L. et al. (Mar. 2, 2004). "Digital Karyotyping Identifies Thymidylate Synthase Amplification as a Mechanism of Resistance to 5-Fluorouracil in Metastatic Colorectal Cancer Patients," *Proc. Natl. Acad. Sci. USA* 101(9):3089-3094.

Werner, H. et al. (2003). "The IGF1 Receptor Gene: A Molecular Target for Disrupted Transcription Factors," *Genes, Chromo. Cancer* 36:113-120.

Wikipedia (2011). "Fatty Acid Synthesis," located at http://en.wikipedia.org/wiki/Fatty_acid_synthesis, last visited on Jan. 18, 2011, this page was created on Feb. 18, 2007, and last modified on Jan. 7, 2011 at 02:23, 2 pages.

Xie, Z. et al. (Jun. 7, 2007). "A Multiplex RT-PCR for Simultaneous Differentiation of Three Viral Pathogens of Penaeid Shrimp," *Dis. Aquat. Organ.* 76:77-80.

Yang, J. et al. (Feb. 1, 2006). "BMS-345541 Targets Inhibitor of $_K$B Kinase and Induces Apoptosis in Melanoma: Involvement of Nuclear Factor $_K$B and Mitochondria Pathways," *Clin. Cancer Res.* 12(3):950-960.

Supplementary European Search Report mailed Dec. 13, 2010, for EP Patent Application No. 07814695.8, filed on Sep. 5, 2007, 8 pages.

European Search Opinion mailed Dec. 13, 2010, for EP Patent Application No. 07814695.8, filed on Sep. 5, 2007, 8 pages.

European Search Opinion mailed on Jul. 6, 2010, for EP Patent Application No. 07841902.5, filed on Sep. 5, 2007, 6 pags.

European Search Opinion mailed on Jul. 8, 2010, for EP Patent Application No. 07875034.6, filed on Jun. 12, 2007, 8 pages.

Carey, L. A. et al. (Jan. 5, 2011). "PARP and Cancer—If It's Broke, Don't Fix It," *New England J. Med.*located at http://www.nejm.org/doi/full/10.1056/NEJMe1012546, last visited on Jan. 6, 2011, 3 pages.

Clinical Trial Registry NCT 01204125, (Sep. 13, 2010). Two Regimens of SAR240550/Weekly Paclitaxel and Paclitaxel Alone as Neoadjuvant Therapy in Triple Negative Breast Cancer Patients (SOLTI NEOPARP), located at http://clinicaltrials.gov/ct2/show/NCT01204125, last visited on Jan. 26, 2011, first received on Sep. 13, 2010, last updated on Nov. 17, 2010, 13 pages.

Clinical Trial Registry Nct 01213381, (Sep. 30, 2010). "Safety and Pharmacokinetics of SAR240550 (BSI-201) Twice Weekly in Patients With Advanced Solid Tumors," located at http://clinicaltrials.gov/ct2/show/NCT01213381, last visited on Jan. 26, 2011, first received on Sep. 30, 2010, last updated on Oct. 1, 2010, 10 pages.

Dwyer, J. et al. (2007). "Transcriptional Regulation of Telomerase Activity: Roles of the the Ets Transcription Factor Family," *Ann. New York Acad. Sci.* 1114:36-47.

Geissler, T. et al. (2010). "PARP Inhibitors as Agrochemically Active Substances," *PARP* 2010, 18$^{th}$*International Conference on ADP-Ribose Metabolism*, Aug. 18-21, 2010, *University of Zurich-Irchel, Zurich, Switzerland, Poster Presentation*, Abstract No. P71, 3 pages.

Kopetz, S. et al. (May 20, 2008). "First Human Phase I Study of BSI-201, a Small Molecule Inhibitor of Poly ADP-Ribose Polymerase (PARP) in Subjects with Advanced Solid Tumors," *Poster Session presented for J. Clin. Oncol.* 26(Supplemental), Abstract No. 3577, 1 page (Poster).

Maegley, K. A. et al. (2010). "An in Vitro Mechanistic Comparison of Clinical PARP Inhibitors," *PARP* 2010, 18$^{th}$ *International Conference on ADP-Ribose Metabolism*, Aug. 18- 21, 2010, *University of Zurich-Irchel, Zurich, Switzerland, Poster Presentation*, Abstract No. P72, 3 pages.

Moulder, S. et al. (Dec. 12, 2010). "[P6-15-01] A Phase 1 b Study to Assess the Safety and Tolerability of the PARP Inhibitor Iniparib (BSI-201) in Combination With Irinotecan for the Treatment of Patients With Metastatic Breast Cancer (MBC)," *Abstract presented at the related to Poster Session No.* 6: *Treatment —Therapeutic Strategies: Novel Targets and Targeted Agents, presented at the 33$^{rd}$ Annual San Antonio Breast Cancer Symposium*, held on Dec. 8-12, 2010, San Antonio, Texas, abstract located at http://www.abstracts2view.com/sabcs10/view.php?nu=SABCS10L__1107 &terms=, last visited on Dec. 22, 2010,1 page (Abstract).

Moulder, S. et al. (Dec. 12, 2010). "[P6-15-01] A Phase 1 b Study to Assess the Safety and Tolerability of the PARP Inhibitor Iniparib (BSI-201) in Combination With Irinotecan for the Treatment of Patients With Metastatic Breast Cancer (MBC)," *Poster Session No.* 6: *Treatment —Therapeutic Strategies: Novel Targets and Targeted Agents, presented at the 33$^{rd}$ Annual San Antonio Breast Cancer Symposium*, held on Dec. 8-12, 2010, San Antonio, Texas, 1 page (Poster).

Neumeister, V. et al. (Dec. 12, 2010). "[P6-04-04] Hypoxia is Associated With Somatic Loss of BRCA1 Protein and Pathway Activity in Triple Negative Breast Cancer,"*Abstract related to Poster Session* 6: *Tumor Cell and Molecular Biology: Molecular Profiles, presented at the 33$^{rd}$ Annual San Antonio Breast Cancer Symposium*, held on Dec. 8-12, 2010, San Antonio, Texas, 1 page (Abstract).

O'Shaughnessy, J. et al. (Oct. 2010). "LAB11—Iniparib With Gem/Carbo, A PARP Inhibitor Strategy, in Metastatic Triple Negative Breast Cancer," & A. Awada et al. "Cationic Liposomal Paclitaxel, A Vascular Disruption Strategy in Advanced Triple Negative Breast Cancer," *Final Oral presentation presented by J. O'shaughnessy et aL, and A. Awada et al., at the EsmoSMO* 2010 *Congress, Milan* 2010, 17 pages total.

O'Shaughnessy, J. et al. (2011). "Iniparib Plus Chemotherapy in Metastatic Triple-NegativeBreast Cancer," *The New England Journal of Medicine*, 10.1056/NEJMoa1011418, and Supplementary Appendix, for a total of 14 pages.

Ossovskaya, V. et al. (2010). "Pathway Analysis of Primary Human Triple-Negative Breast Cancers," Poster Session No. 6: Tumor Cell and Molecular Biology: Molecular Profiles, presented at the 33$^{rd}$ Annual San Antonio Breast Cancer Symposium, San Antonio, Texas, USA, Dec. 8-12, 2010, one page (Poster).

Ossovskaya, V. et al. (2010). "[P06-04-12] Pathway Analysis of Primary Human Triple-Negative Breast Cancers,"Abstract presented at the 33$^{rd}$ Annual San Antonio Breast Cancer.Symposium, San Antonio, Texas, USA, Dec. 12, 2010, abstract located at http://www.abstracts2view.com/sabcs10/view.php?nu=SABCS10L__423 &terms=, last visited on Jan. 6, 2011, one page (Abstract).

Ossovskaya, V. et al. (2010). "Cell Cycle Effects of Iniparib, A PARP Inhibitor, in Combination With Gemcitabine and Carboplatin in the MDA-MBb-468(-) Triple-Negative Breast Cancer (TNBC) Cell Line," Oral Presentation No. P05-06-09, presented at the 33$^{rd}$ Annual San Antonio Breast Cancer Symposium, San Antonio, Texas, USA, Dec. 8-12, 2010, one page.

Pal, S. K. et al. (2010, e-published Dec. 15, 2010). "Triple Negative Breast Cancer: Unmet Medical Needs," *Breast Cancer Research and Treatment* 125(3):627-636.

Phend, C. (Jan. 5, 2011). "PARP Inhibitor Shines in Triple-Negative Breast Cancer," *News Release from Medpage Today*, article located at http://www.medpagetoday.com/HematologyOncology/BreastCancer/24195, last visited on Jan. 6, 2011, 4 pages.

\* cited by examiner

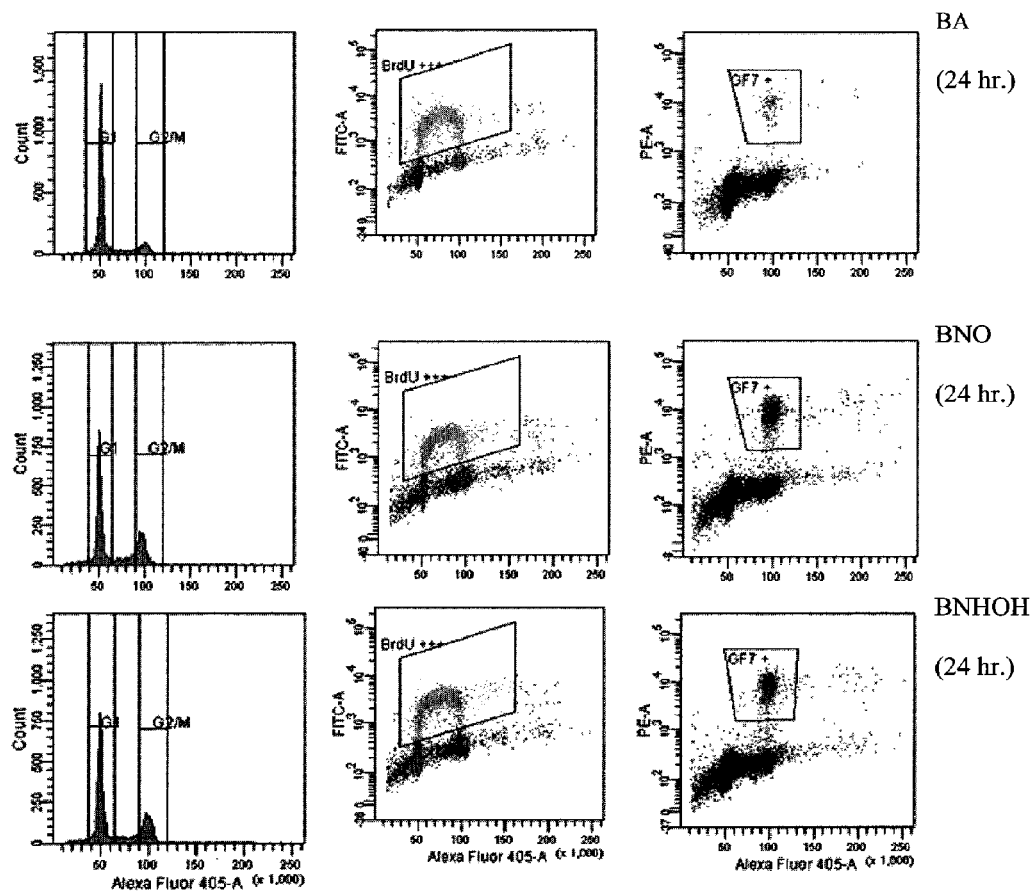
FIG. 2: Metabolites of BA induce G2/M cell cycle arrest at 24 hr in Hela cells

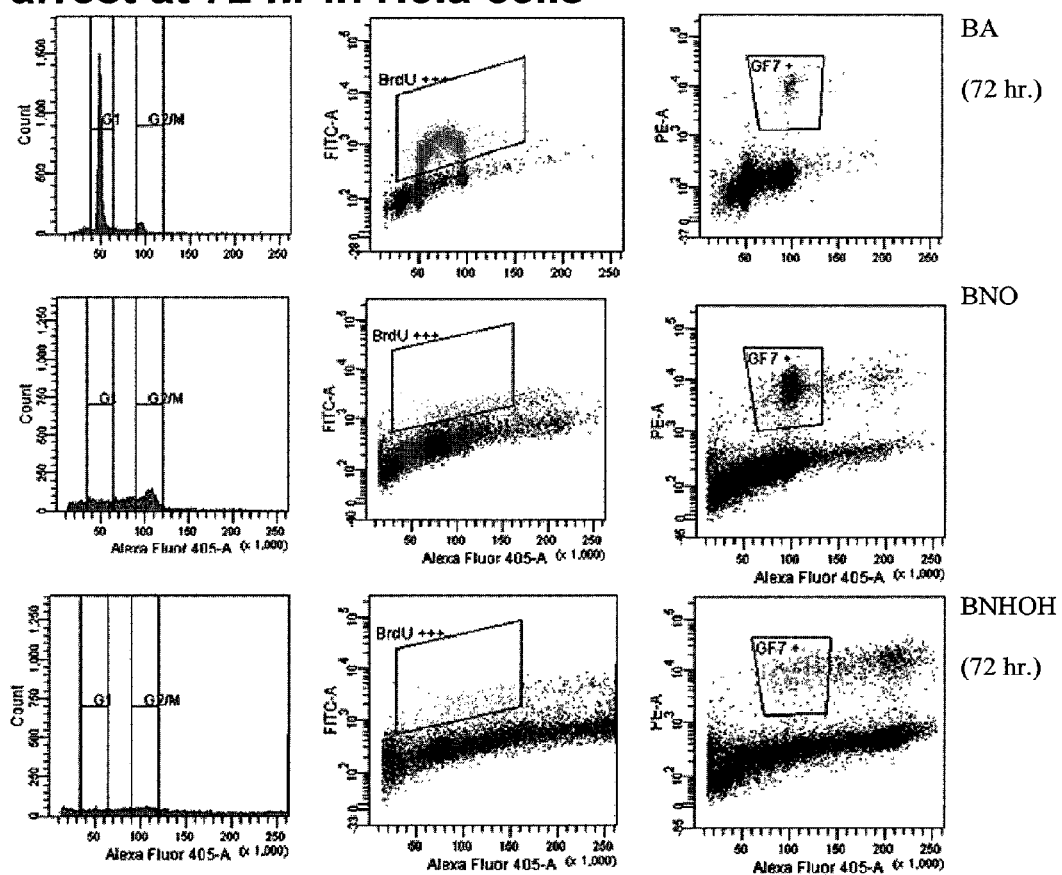
FIG. 3: Metabolites of BA induce G2/M cell cycle arrest at 72 hr in Hela cells

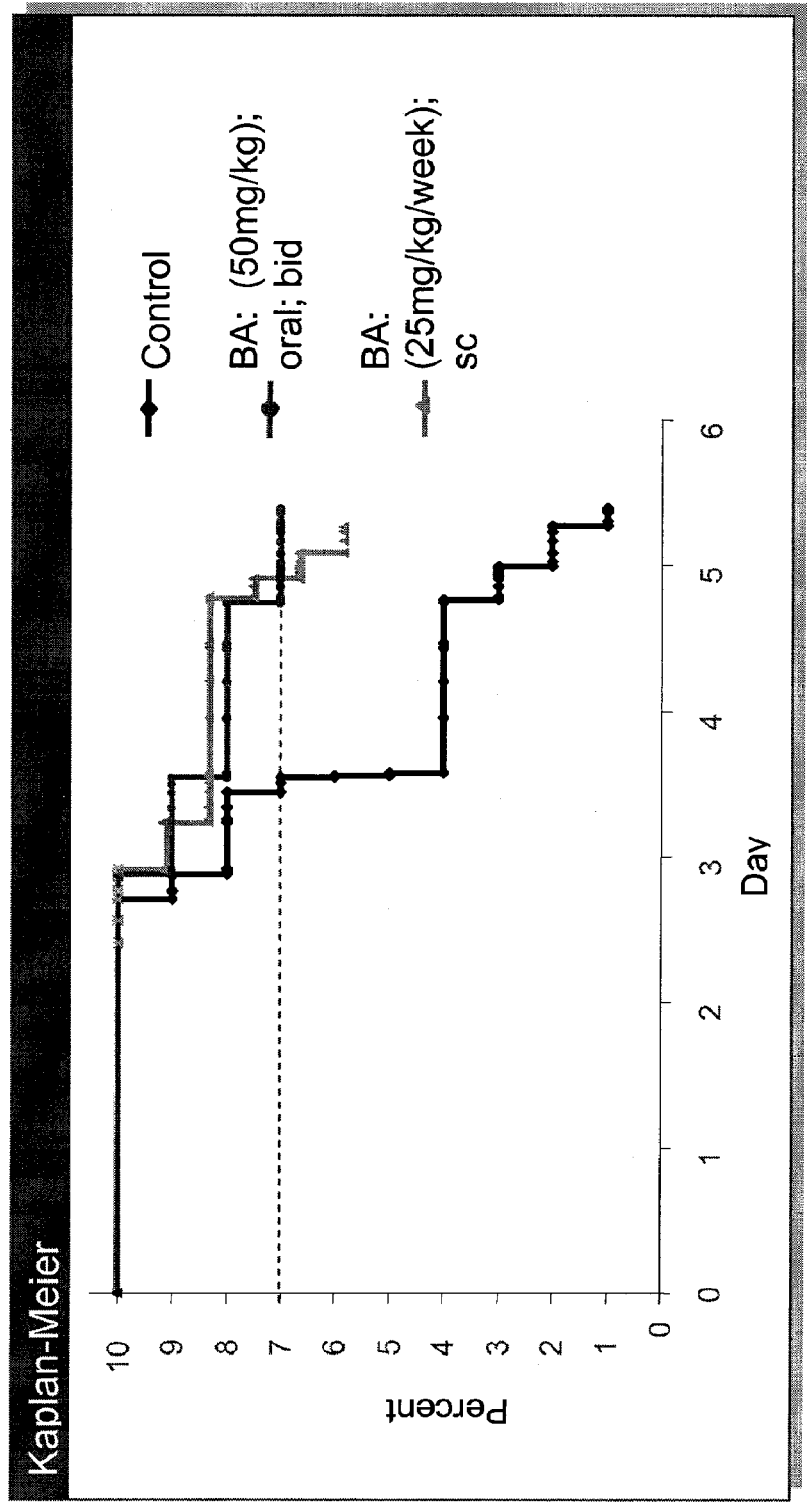
FIG. 4: BA activity in the human OVCAR-3 ovarian adenocarcinoma xenograft in female SCID mice
BA was dosed orally 50 mg/kg twice daily or dosed subcutaneously 25mg/kg/week (s.c.) via osmotic pumps

FIG. 5: 4-Iodo-3-Nitrobenzamide targets multi-drug resistant tumor cells with up-regulated MDR1
FIG. 5A: KB 3-1
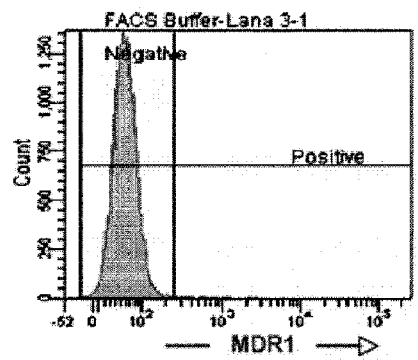
FIG. 5B: KB V-1
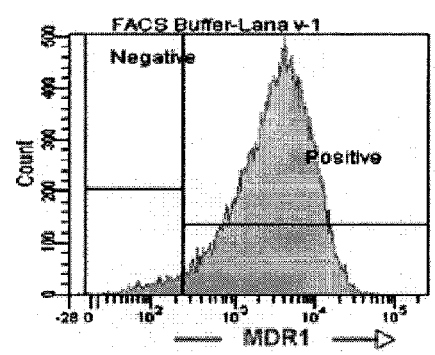
FIG. 5C:
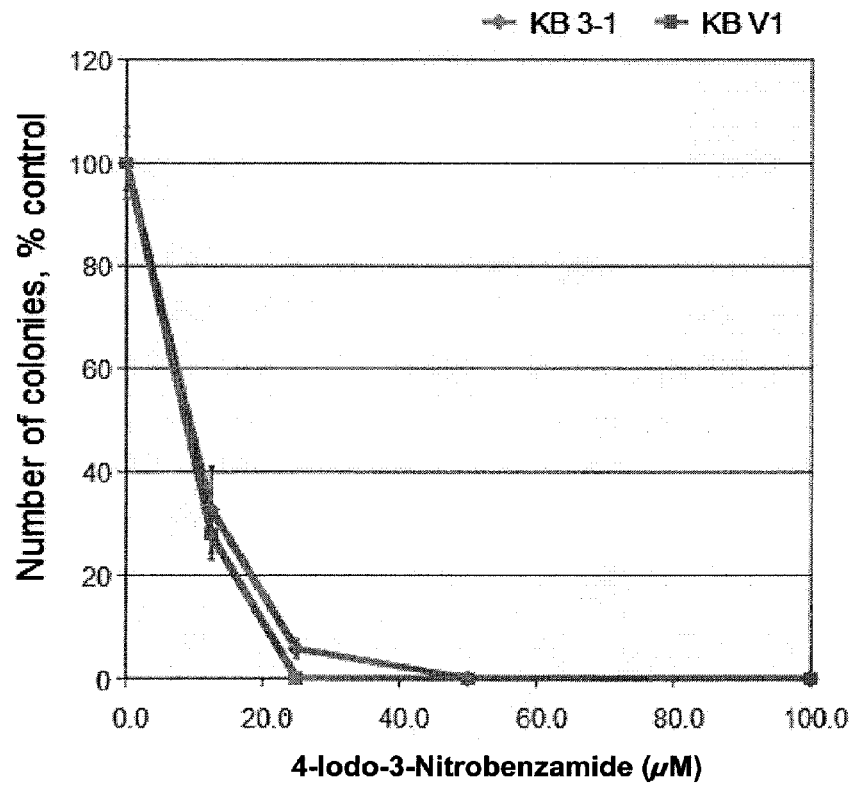

TREATMENT OF CANCER

CROSS-REFERENCE

This application claims the benefit of U.S. Provisional Application No. 60/842,474, filed Sep. 5, 2006, which is incorporated herein by reference in its entirety.

BACKGROUND OF THE INVENTION

Cancer is a serious threat to modern society. Malignant cancerous growths, due to their unique characteristics, pose significant challenges for modern medicine. Their characteristics include uncontrollable cell proliferation resulting in unregulated growth of malignant tissue, an ability to invade local and even remote tissues, lack of differentiation, lack of detectable symptoms and most significantly, the lack of effective therapy and prevention.

Cancer can develop in any tissue of any organ or tissue at any age. The etiology of cancer is not clearly defined but mechanisms such as genetic susceptibility, chromosome breakage disorders, viruses, environmental factors and immunologic disorders have all been linked to malignant cell growth and transformation. Cancer encompasses a large category of medical conditions, affecting millions of individuals worldwide. Cancer develops when cells in a part of the body begin to undifferentiate or grow out of control. All cancer types begin with the out-of-control growth of abnormal cells.

There are many types of cancer, including breast, lung, ovarian, bladder, prostate, pancreatic, cervical and leukemia. Currently, some of the main treatments available are surgery, radiation therapy, and chemotherapy. Surgery is often a drastic measure and can have serious consequences. For example, all treatments for ovarian cancer may result in infertility. Some treatments for cervical cancer and bladder cancer may cause infertility and/or sexual dysfunction. Surgical procedures to treat pancreatic cancer may result in partial or total removal of the pancreas and can carry significant risks to the patient. Breast cancer surgery invariably involves removal of part or the entire breast, and in severe cases, surrounding tissue. Some surgical procedures for prostate cancer carry the risk of urinary incontinence and impotence. Surgical procedures for lung cancer patients often give rise to significant post-operative pain, as the ribs must be cut through to access and remove the cancerous lung tissue. In addition, patients who have both lung cancer and another lung disease, such as emphysema or chronic bronchitis, typically experience an increase in their shortness of breath following the surgery.

Radiation therapy has the advantage of killing cancer cells but it also damages non-cancerous tissue at the same time. Chemotherapy involves the administration of various anti-cancer drugs to a patient but often is accompanied by adverse side effects.

Worldwide, more than 10 million people are diagnosed with cancer every year and it is estimated that this number will grow to 15 million new cases every year by 2020. Cancer causes six million deaths every year or 12% of the deaths worldwide. There remains a need for methods that can treat cancer. These methods can provide the basis for pharmaceutical compositions useful in the prevention and treatment of cancer in humans and other mammals.

A series of anti-tumor drugs have been identified. These drugs include nitro and nitroso compounds and their metabolites, which are the subject of U.S. Pat. No. 5,464,871 issued on Nov. 7, 1995 entitled "Aromatic Nitro and Nitroso Compounds and their Metabolites Useful as Anti-viral and Anti-tumor Agents," U.S. Pat. No. 5,670,518 issued on Sep. 23, 1997 entitled "Aromatic Nitro and Nitroso Compounds and their Metabolites Useful as Anti-viral and Anti-tumor Agents," U.S. Pat. No. 6,004,978 issued on Dec. 21, 1999 entitled "Methods of Treating Cancer with Aromatic Nitro and Nitroso Compounds and their Metabolites" the disclosures of which are incorporated herein by reference. The use of these compounds has been described in the art as useful in treating mammary gland adenocarcinomas, mammary gland duct carcinomas, lymphocytic leukemia, Kaposi's sarcoma in immunosuppressed patients with AIDS, and neoplastic growths such as non-Hodgkin's lymphoma, and primary lymphomas. However, there is a need to identify additional compounds with anti-tumor activity. Metabolites isolated from precursor compounds provide a source of anti-tumor agents that can be used individually or in combination with other compounds to target various cancerous cells. Metabolites isolated from benzamide precursor compounds provide one such source.

SUMMARY OF THE INVENTION

The present invention relates generally to methods of treatment of tumorigenic diseases using aromatic nitrobenzamide metabolite compounds. More specifically, it relates to the nitrobenzamide metabolite compounds derived from the nitro compound benzamide precursor molecules and the use of said metabolites or a salt, solvate, isomer, tautomer, metabolite, analog, or prodrug thereof, in suppressing and inhibiting tumor growth in a mammal.

In one aspect of the invention, a method for treatment of cancer and disorders associated with cancer is provided comprising the administration of pharmaceutical compositions comprising a compound of formula (Ia) with one or more additional pharmacologically active agents. In another aspect, a method for treatment of cancer and disorders associated with cancer is provided comprising the administration of a combination of a metabolite compound derived from a compound of formula (Ia) and buthionine sulfoximine (BSO). Said metabolite(s) can also be administered in combination with a benzopyrone compound of formula (II), with or without BSO.

Embodiments of these aspects include methods of treating various cancers, including leukemia, breast cancer, ovarian cancer, lung cancer, bladder cancer, prostate cancer, pancreatic cancer, and cervical cancer, as well as other cancer types described herein.

This invention relates to compositions of matter and pharmaceutical compositions, and to methods for their use in the treatment of cancer. For example, a composition of the invention can be a combination of two or more compounds described herein and/or a combination of two or more forms of a compound described herein. A pharmaceutical composition of the invention may be a composition suitable for administration to a subject.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 (FACS dot plots and histograms) illustrates cell-cycle analysis of Hela cells treated with PARP-1 inhibitors BA, 4-iodo-3-nitrosobenzamide (BNO) and 4-iodo-3-hydroxyaminobenzamide (BNHOH) for 24 hours. BrdU staining label cells in S-phase of cell cycle. GF7 staining label cells in mitosis.

FIG. 3 (FACS dot plots and histograms) illustrates cell-cycle analysis of Hela cells treated with PARP-1 inhibitors BA, 4-iodo-3-nitrosobenzamide (BNO) and 4-iodo-3-hydroxyaminobenzamide (BNHOH) for 72 hours. BrdU staining label cells in S-phase of cell cycle. GF7 staining label cells in mitosis.

FIG. 4 shows BA activity in the human OVCAR-3 ovarian adenoma xenograft in female SCID mice. BA was dosed orally b.i.d. at 50 mg/kg/dose or s.c. via osmotic pumps at a dose of 25 mg/kg/week.

FIG. 5 shows that BA targets multi-drug resistant cells that up-regulate MDR1 as well as MDR1-negative cells.

FIG. 5A shows the level of MDR1 expression in KB 3-1 cells. FIG. 5B shows the level of MDR1 expression in KB V-1 cells. FACS histogram illustrates overexpression of MDR1 in KB V-1 cells. As overexpression of MDR1 is associated with multidrug resistance, it is notable that, as shown in FIG. 5C, BA results in dose-dependent cell death in both KB 3-1 and KB V-1 cells.

DETAILED DESCRIPTION OF THE INVENTION

Definitions

Figure 1:
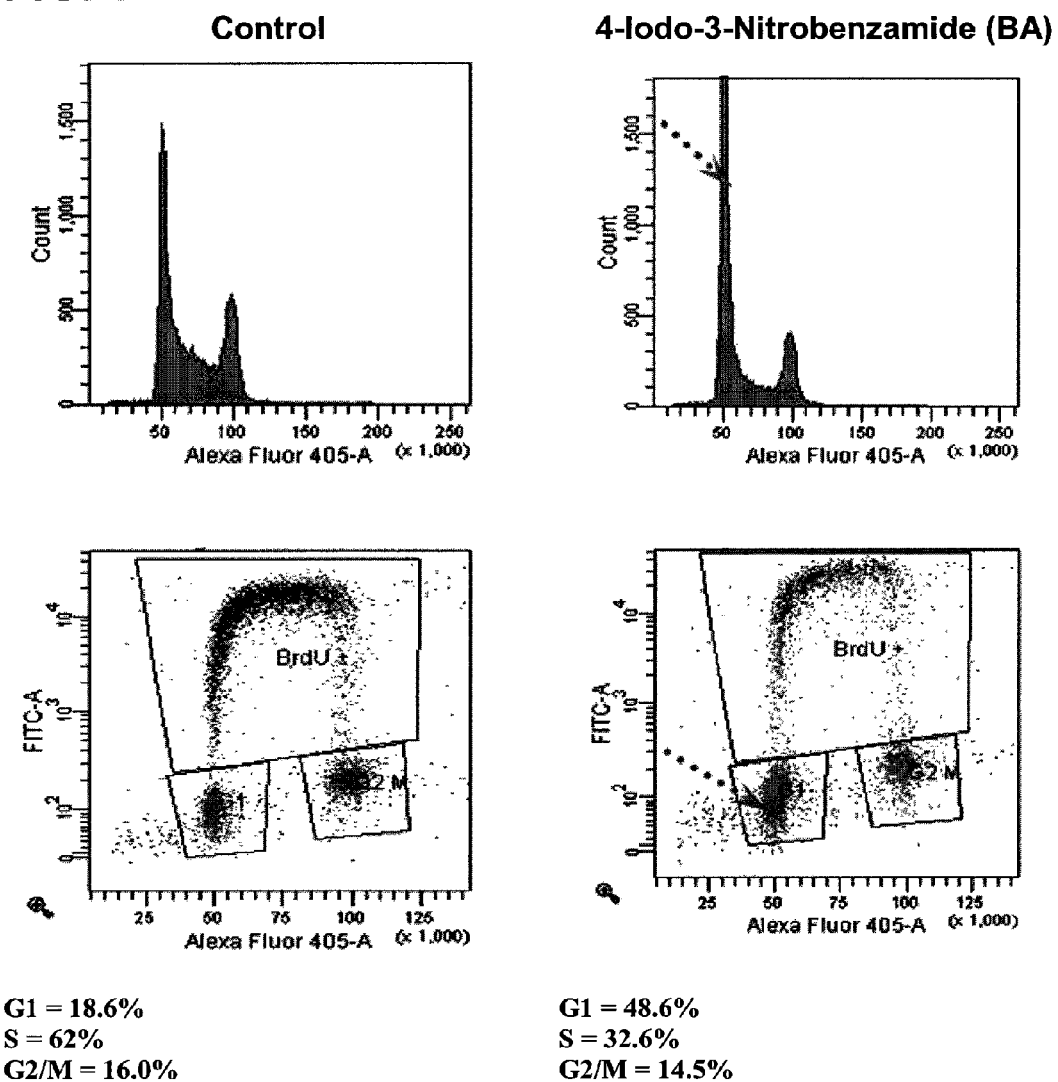
FIG. 1 illustrates (FACS dot plots and histograms) cell-cycle analysis in HTC116 cells treated with PARP-1 inhibitor (4-iodo-3-nitrobenzamide or "BA") for 19 hours. BA treatment caused an increase in the number of cells in the G1 phase (48.6%) as compared to control (18.6%) with a concomitant decrease of S phase cell cycle.

"Nitrobenzamide precursor compound(s)" means a compound of the formula (Ia)

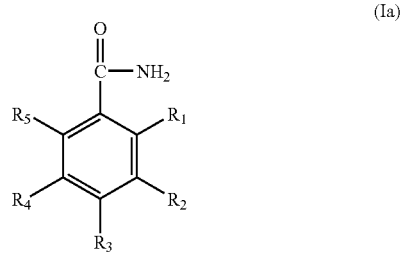

(Ia)

wherein $R_1$, $R_2$, $R_3$, $R_4$, and $R_5$ are, independently selected from the group consisting of hydrogen, hydroxy, amino, nitro, iodo, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, at least one of the five substituents are always nitro, and at least one substituent positioned adjacent to a nitro is always iodo, and pharmaceutically acceptable salts, solvates, isomers, tautomers, metabolites, analogs, or prodrugs thereof. $R_1$, $R_2$, $R_3$, $R_4$, and $R_5$ can also be a halide such as chloro, fluoro, or bromo. "Precursor compound" is a compound that undergoes one or more chemical or biochemical processes (e.g., in a cell or in an organism) that result in a metabolite compound. The terms "precursor", "precursor compound", "benzamide precursor" or "nitrobenzamide precursor" are used interchangeably herein.

"Metabolite" means a compound produced through any in vitro or in vivo metabolic process which results in a product that is different in structure than that of the starting compound. The term "metabolite" includes nitrobenzamide metabolite compounds. A metabolite can include a varying number or types of substituents that are present at any position relative to a precursor compound, such as the precursor compound depicted in the formula (Ia). In addition, a metabolite can vary in the number of types of substituents that are present at any position relative to the compounds depicted in herein. In addition, the terms "metabolite", "metabolite compound", "benzamide metabolite compound" or "nitrobenzamide metabolite compound" are used interchangeably herein.

"Surgery" means any therapeutic or diagnostic procedure that involves methodical action of the hand or of the hand with an instrument, on the body of a human or other mammal, to produce a curative, remedial, or diagnostic effect.

"Radiation therapy" means exposing a patient to high-energy radiation, including without limitation x-rays, gamma rays, and neutrons. This type of therapy includes without limitation external-beam therapy, internal radiation therapy, implant radiation, brachytherapy, systemic radiation therapy, and radiotherapy.

"Chemotherapy" means the administration of one or more anti-cancer drugs and/or other agents to a cancer patient by various methods, including intravenous, oral, intramuscular, intraperitoneal, intravesical, subcutaneous, transdermal, buccal, or inhalation or in the form of a suppository. Chemotherapy may be given prior to surgery to shrink a large tumor prior to a surgical procedure to remove it, after surgery or radiation therapy to prevent the growth of any remaining cancer cells in the body.

The terms "effective amount" or "pharmaceutically effective amount" refer to a non-toxic but sufficient amount of the agent to provide the desired biological, therapeutic, and/or prophylactic result. That result can be reduction and/or alleviation of the signs, symptoms, or causes of a disease, or any other desired alteration of a biological system. For example, an "effective amount" for therapeutic uses is the amount of a nitrobenzamide metabolite compound as disclosed herein per se or a composition comprising the nitrobenzamide metabolite compound herein required to result in a clinically significant decrease in a disease. An appropriate effective amount in any individual case may be determined by one of ordinary skill in the art using routine experimentation.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

The term "treating" and its grammatical equivalents as used herein include achieving a therapeutic benefit and/or a prophylactic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder. For prophylactic benefit, a method of the invention may be performed on, or a composition of the invention administered to a patient at risk of developing cancer, or to a patient reporting one or more of the physiological symptoms of such conditions, even though a diagnosis of the condition may not have been made.

As used herein "BA" means 4-iodo-3-nitrobenzamide; "BNO" means 4-iodo-3-nitrosobenzamide; "BNHOH" means 4-iodo-3-hydroxyaminobenzamide.

(i) Nitrobenzamide Metabolite Compounds

Precursor compounds useful in the present invention are of Formula (Ia)

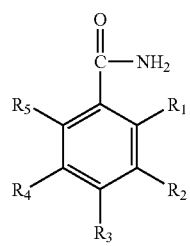

(Ia)

wherein $R_1$, $R_2$, $R_3$, $R_4$, and $R_5$ are, independently selected from the group consisting of hydrogen, hydroxy, amino, nitro, iodo, $(C_1$-$C_6)$ alkyl, $(C_1$-$C_6)$ alkoxy, $(C_3$-$C_7)$ cycloalkyl, and phenyl, wherein at least two of the five $R_1$, $R_2$, $R_3$, $R_4$, and $R_5$ substituents are always hydrogen, at least one of the five substituents are always nitro, and at least one substituent positioned adjacent to a nitro is always iodo, and pharmaceutically acceptable salts, solvates, isomers, tautomers, metabolites, analogs, or pro-drugs thereof. $R_1$, $R_2$, $R_3$, $R_4$, and $R_5$ can also be a halide such as chloro, fluoro, or bromo substituents.

A preferred precursor compound of formula Ia is:

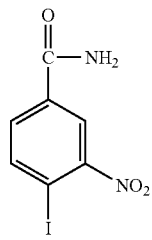

4-iodo-3-nitrobenzamide
(BA)

Metabolites useful in the present invention are of the Formula (Ia):

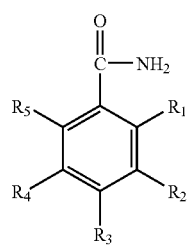

(IIa)

wherein either: (1) at least one of $R_1$, $R_2$, $R_3$, $R_4$, and $R_5$ substituent is always a sulfur-containing substituent, and the remaining substituents $R_1$, $R_2$, $R_3$, $R_4$, and $R_5$ are independently selected from the group consisting of hydrogen, hydroxy, amino, nitro, iodo, bromo, fluoro, chloro, $(C_1$-$C_6)$ alkyl, $(C_1$-$C_6)$ alkoxy, $(C_3$-$C_7)$ cycloalkyl, and phenyl, wherein at least two of the five $R_1$, $R_2$, $R_3$, $R_4$, and $R_5$ substituents are always hydrogen; or (2) at least one of $R_1$, $R_2$, $R_3$, $R_4$, and $R_5$ substituents is not a sulfur-containing substituent and at least one of the five substituents $R_1$, $R_2$, $R_3$, $R_4$, and $R_5$ is always iodo, and wherein said iodo is always adjacent to a $R_1$, $R_2$, $R_3$, $R_4$, or $R_5$ group that is either a nitro, a nitroso, a hydroxyamino, hydroxy or an amino group; and pharmaceutically acceptable salts, solvates, isomers, tautomers, metabolites, analogs, or pro-drugs thereof. In some embodiments, the compounds of (2) are such that the iodo group is always adjacent a $R_1$, $R_2$, $R_3$, $R_4$ or $R_5$ group that is a nitroso, hydroxyamino, hydroxy or amino group. In some embodiments, the compounds of (2) are such that the iodo group is always adjacent a $R_1$, $R_2$, $R_3$, $R_4$ or $R_5$ group that is a nitroso, hydroxyamino, or amino group.

The following compositions are preferred metabolite compounds, each represented by a chemical formula:

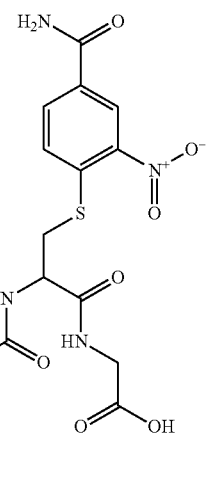

MS472

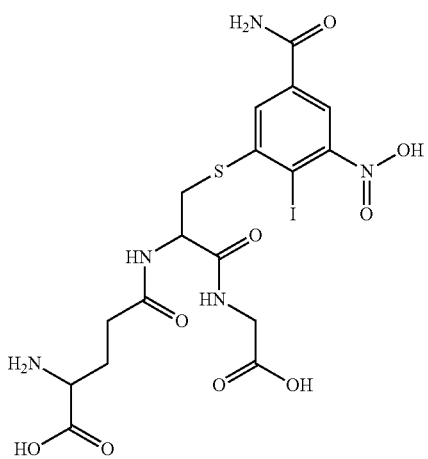

MS601

R$_6$ is selected from a group consisting of hydrogen, alkyl(C$_1$-C$_8$), alkoxy (C$_1$-C$_8$), iso-quinolinones, indoles, thiazole, oxazole, oxadiazole, thiophene, or phenyl.

MS635b
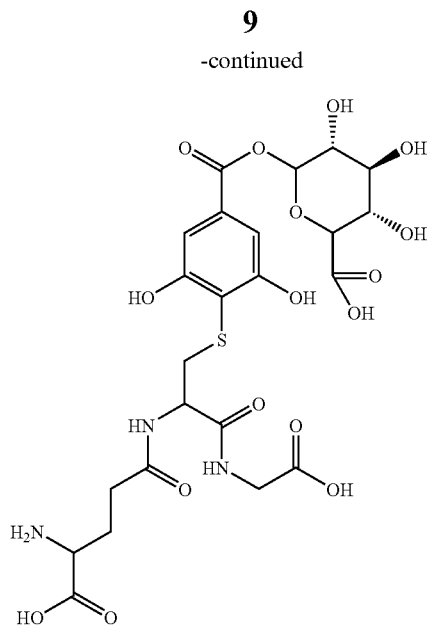
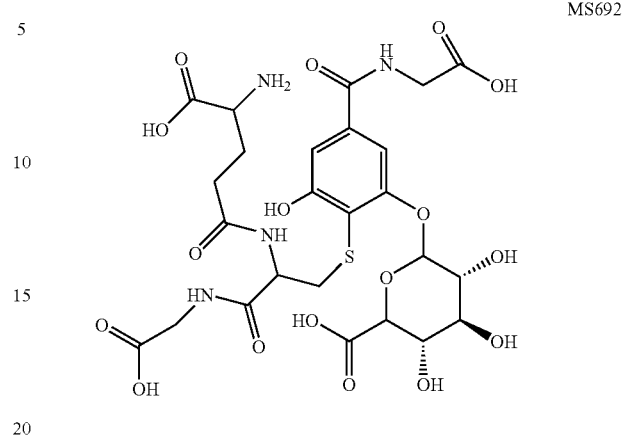
MS692
While not being limited to any one particular mechanism, the following provides an example for MS292 metabolism via a nitroreductase or glutathione conjugation mechanism:
Nitroreductase Mechanism
MS471
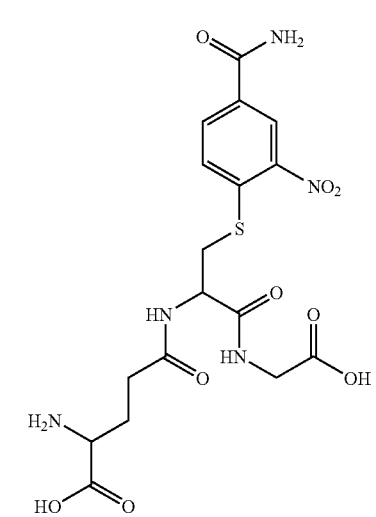
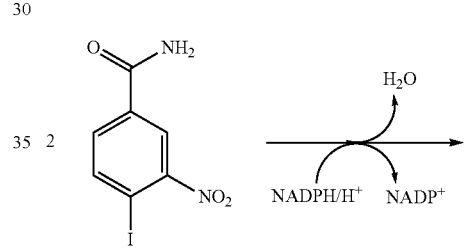
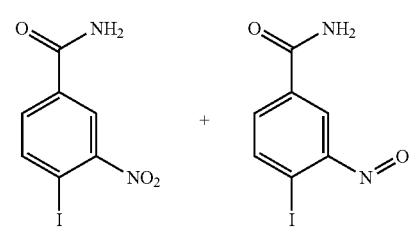
MS414
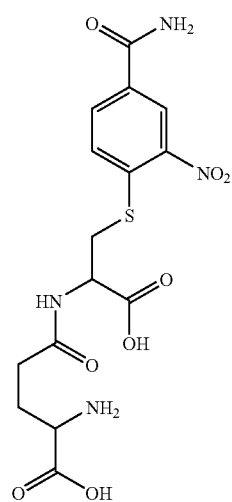
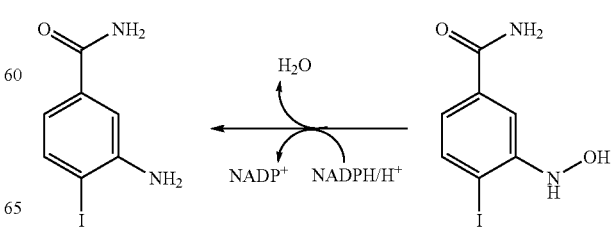

BA glutathione conjugation and metabolism:

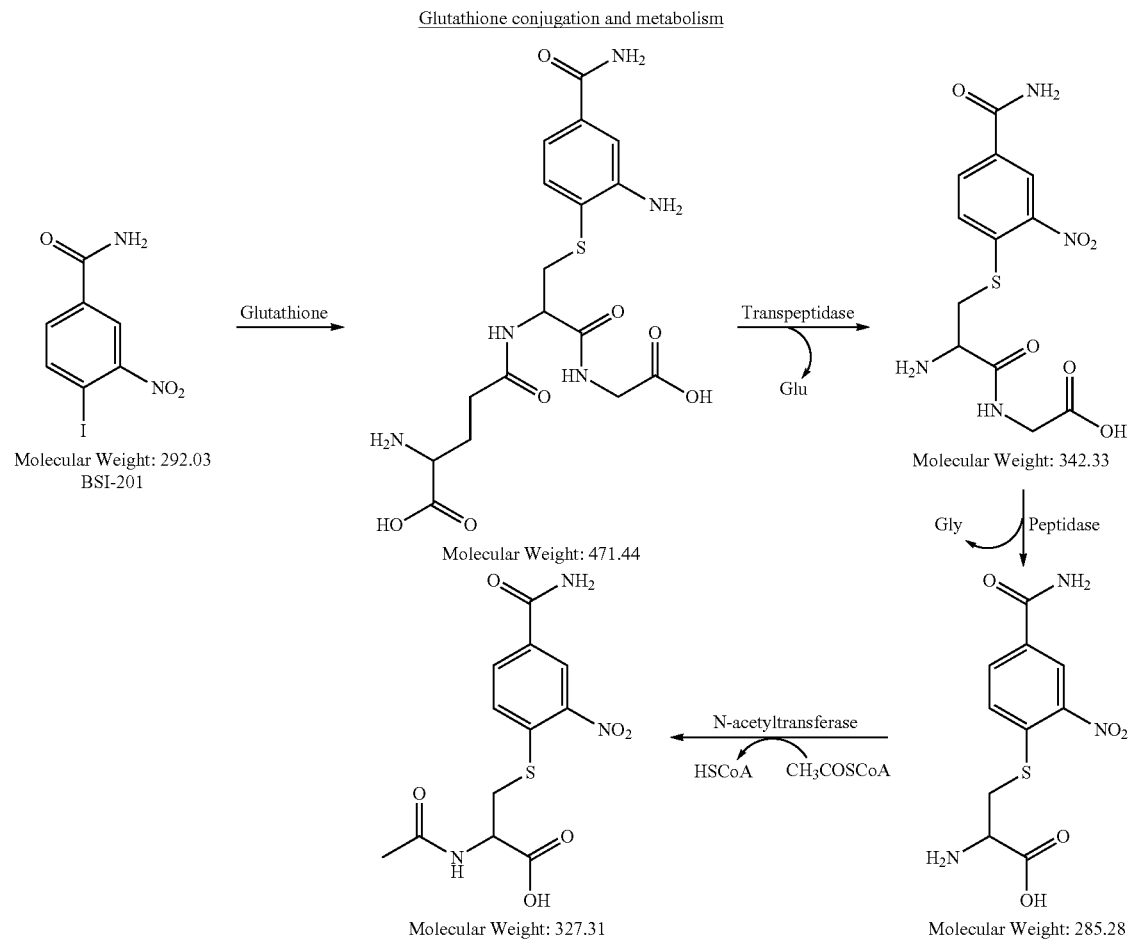

The present invention provides for the use of the aforesaid nitrobenzamide metabolite compounds for the treatment of other breast cancers including a ductal carcinoma in a mammary gland, other forms of leukemia including acute promyelocytic leukemia in peripheral blood, ovarian cancer, lung cancer, bladder cancer, prostate cancer, pancreatic cancer, and cervical cancer, as well as other cancer types described herein.

It has been reported that nitrobenzamide metabolite compounds have selective cytotoxicity upon malignant cancer cells but not upon non-malignant cancer cells. See Rice et at., Proc. Natl. Acad. Sci. USA 89:7703-7707 (1992). In one embodiment, the nitrobenzamide metabolite compounds utilized in the methods of the present invention may exhibit more selective toxicity towards tumor cells than non-tumor cells.

It has been reported that the tumorigenicity of nitrobenzamide and nitrososbenzamide compounds is enhanced when BSO is co-administered to cancer cells. See Mendeleyev et al., Biochemical Pharmacol. 50(5):705-714 (1995). Buthionine sulfoximine (BSO) inhibits gamma-glutamylcysteine synthetase, a key enzyme in the biosynthesis of glutathione, which is responsible in part for cellular resistance to chemotherapy. See Chen et al., Chem. Biol. Interact. April 24; 111-112:263-75 (1998). The invention also provides a method for treating cancer comprising the administration of a nitrobenzamide metabolite compound and/or benzopyrone compound in combination with BSO. Alternatively, metabolite compounds can be administered with precursor compounds and/or benzopyrone.

In addition to BSO, other inhibitors of gamma-glutamylcysteine synthetase can be used in combination with nitrobenzamide and/or benzopyrone compounds. Other suitable analogs of BSO include, but are not limited to, proprothionine sulfoximine, methionine sulfoximine, ethionine sulfoximine, methyl buthionine sulfoximine, γ-glutamyl-α-aminobutyrate and γ-glutamylcysteine.

Benzopyrone Compounds

In some embodiments, the metabolite(s) compounds are administered in combination with benzamide compounds and/or benzopyrone compounds of formula II. The benzopyrone compounds of formula II are,

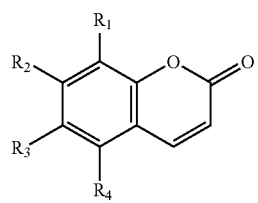

Formula II wherein $R_1$, $R_2$, $R_3$ and $R_4$ are independently selected from the group consisting of H, halogen, optionally substituted hydroxy, optionally substituted amine, optionally substituted lower alkyl, optionally substituted phenyl, optionally substituted $C_4$-$C_{10}$ heteroaryl and optionally substituted $C_3$-$C_8$ cycloalkyl or a salt, solvate, isomer, tautomers, metabolite, or pro-drug thereof.

In a preferred embodiment, the invention relates to the following benzopyrone compound of formula II

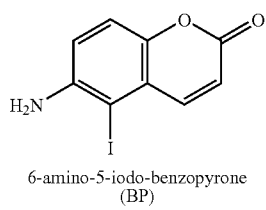

6-amino-5-iodo-benzopyrone
(BP)

(ii) Mechanism of Nitrobenzamide Metabolite Compounds

Not intending to be limited by one mechanism of action, the compounds described herein are believed to have anti-cancer properties via the modulation of a poly (ADP-ribose) polymerase enzyme. The drugs' mechanism of action is related to their ability to act as a ligand for the nuclear enzyme poly (ADP-ribose) polymerase (PARP-1). See Mendeleyev et al., supra, (1995). PARP-1 is expressed in the nucleus and catalyzes the conversion of β-nicotinamide adenine dinucleotide ($NAD^+$) into nicotinamide and poly-ADP-ribose (PAR). The role of PARP-1 in homeostatic conditions seems to be limited to DNA transcription and repair. However, when cellular stress causes DNA damage, PARP-1 activity increases dramatically, which appears to be necessary for genomic integrity. Shall et at., Mutat Res. Jun. 30; 460(1): 1-15 (2000). In addition, while PARP-1 is the best known member of the PARP family of enzymes, the mechanism of action is equally applicable to any member of the PARP family (e.g., PARP-2 through PARP-18, or additional members discovered to operate by similar mechanisms of action, or sharing similar structures to PARP-1).

One function of PARP-1 is the synthesis of the biopolymer, poly (ADP-ribose). Both poly (ADP-ribose) and PARP-1 have been linked to the repair of DNA repair, apoptosis, the maintenance of genomic stability, and carcinogenesis. See Masutani et al., Genes, Chromosomes, and Cancer 38:339-348 (2003). PARP-1 plays a role in DNA repair, specifically base excision repair (BER). BER is a protection mechanism in mammalian cells for single-base DNA breakage. PARP-1 binds to the ends of DNA fragments through its zinc finger domains with great affinity and thereby acts as a DNA damage sensor. Gradwohl et al., Proc. Natl. Acad. Sci. USA 87:2990-2994 (1990); Murcia et al., Trends Biochem. Sci 19: 172-176 (1994). A breakage in the DNA triggers a binding response by PARP-1 to the site of the break. PARP-1 then increases its catalytic activity several hundred fold (See Simonin et al., J Biol. Chem. 278: 13454-13461 (1993)) and begins to convert poly ADP-ribosylation of itself (Desmarais et al., Biochim. Biophys. Acta 1078: 179-186 (1991)) and BER proteins, such as DNA-dependent protein kinase (DNA-PKcs) and the molecular scaffold protein XRCC-1. See Ruscetti et al., J. Biol. Chem. Jun. 5; 273(23):14461-14467 (1998) and Masson et al., Mol Cell Biol. Jun., 18(6):3563-71 (1998). BER proteins are rapidly recruited to the site of DNA damage. El-Kaminsy et al., Nucleic Acid Res. 31(19):5526-5533 (2003); Okano et al., Mol Cell Biol. 23(11):3974-3981 (2003). PARP-1 dissociates from the DNA breakage site but remains in the vicinity of the DNA repair event.

Inhibiting the activity of a PARP molecule includes reducing the activity of these molecules. The term "inhibits" and its' grammatical conjugations, such as "inhibitory," is not intended to require complete reduction in PARP activity. Such reduction is preferably by at least about 50%, at least about 75%, at least about 90%, and more preferably by at least about 95% of the activity of the molecule in the absence of the inhibitory effect, e.g., in the absence of an inhibitor, such as a nitrobenzamide metabolite compound of the invention. Most preferably, the term refers to an observable or measurable reduction in activity. In treatment scenarios, preferably the inhibition is sufficient to produce a therapeutic and/or prophylactic benefit in the condition being treated. The phrase "does not inhibit" and its' grammatical conjugations does not require a complete lack of effect on the activity. For example, it refers to situations where there is less than about 20%, less than about 10%, and preferably less than about 5% of reduction in PARP activity in the presence of an inhibitor such as a nitrobenzamide metabolite compound of the invention.

Another mechanism of action can include inhibition of inosine monophosphate dehydrogenase (IMPDH). IMPDH is the rate-limiting enzyme of the branched purine nucleotide synthetic pathway that provides guanylates including GTP and dGTP. There are two isoforms of IMPDH, type I that is constitutively present in all cells, and type II that is inducible and is present in highly proliferating cells such as cancer. Inhibition of the latter enzyme brings about a profound depletion of intracellular guanosine nucleotides essential for tumor cell growth and replication. One or more metabolite compounds of the present invention or can target IMPDH thus inhibiting tumor cell growth.

Yet another mechanism of action can include inhibition of histone deacytelase (HDAC). Tumor-associated alterations in transcription factor pools may lead to misregulation of genes important in normal growth and development. Chimeric transcription factors cause transcriptional repression of growth regulatory target genes by the aberrant recruitment of transcriptional corepressors and their associated HDAC activity. In human acute promyelocytic leukemia, chimeric transcription factors involving retinoic acid receptor (PML-RARα and PLZF-RARα) have been found to repress transcription of target genes such as the RARβ gene. Transcriptional corepressor complexes contain HDAC activity and transcriptional coactivator complexes contain histone acetyltransferase activity. HDAC inhibitors such as trichostatinA or NaBu are able to relieve the transcriptional repression caused by the chimeric transcription factors PML-RARα and PLZFRARα HDAC inhibitors alone or in combination with retinoids have been shown to induce leukemia remission and prolonged survival in an animal model of acute promyelocytic leukemia without apparent side effects.

Acetylation and deacetylation of histones alter higher order chromatin structure by influencing histone interaction with DNA. Transcription factors may also be acetylated, and the acetylated status of these proteins may influence their interaction with DNA, as well as their ability to interact with other transcriptional coregulatory proteins. For example, acetylation of p53 enhances its sequence specific DNA binding activity. Deacetylated histones are associated with cell growth, whereas hyperacetylated histones are associated with cell growth arrest, differentiation, and/or apoptosis.

For example, Saito et al. evaluated the efficacy of MS-27-275, a synthetic benzene derivative that inhibits HDAC. Saito et al. Proc. Natl. Acad. Sci., 1999; 96: 4592-4597. In a number of adult tumor cell lines, MS-27-275 inhibited tumor cell growth with an IC50 in the submicromolar range. The inhibition of cell growth was accompanied by a cell cycle arrest and an induction of the cell cycle inhibitor p21. MS-27-275 administered p.o. inhibited the growth of established adult tumor lines s.c. implanted in nude mice with minimal toxicities. See also, Jaboin et al. Cancer Research, 2002; 62:6108-6115.

As such the compounds of the present invention, as HDAC inhibitors, can modulate transcriptional activity. Therefore, the compounds of the present invention, can also act to block angiogenesis and cell cycling, and promote apoptosis and differentiation. By targeting these key components of tumor proliferation, HDAC inhibitors have the potential to occupy an indomitable position in the fast-moving cytostatic market. Two major reasons why HDAC inhibitors could play such a key role because they can be used concurrent to other treatment regimes, such as to improve the efficacy of existing cytostatics (such as the retinoids) and moreover, they are able to target the transcription of specific disease-causing genes, conferring unprecedented therapeutic windows to cancer therapy.

Uses of the Benzamide Metabolite Compounds

Cancer Types

The invention provides methods to treat several specific cancers or tumors. For example, cancer types include adrenal cortical cancer, anal cancer, aplastic anemia, bile duct cancer, bladder cancer, bone cancer, bone metastasis, Adult CNS brain tumors, Children CNS brain tumors, breast cancer, Castleman's Disease, cervical cancer, childhood Non-Hodgkin's lymphoma, colon and rectum cancer, endometrial cancer, esophagus cancer, Ewing's family of tumors, eye cancer, gallbladder cancer, gastrointestinal carcinoid tumors, gastrointestinal stromal tumors, gestational trophoblastic disease, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, thyroid cancer, uterine sarcoma, vaginal cancer, vulvar cancer, and Waldenstrom's macroglobulinemia.

Carcinoma of the thyroid gland is the most common malignancy of the endocrine system. Carcinoma of the thyroid gland includes differentiated tumors (papillary or follicular) and poorly differentiated tumors (medullary or anaplastic). Carcinomas of the vagina include squamous cell carcinoma, adenocarcinoma, melanoma and sarcoma. Testicular cancer is broadly divided into seminoma and non-seminoma types.

Thymomas are epithelial tumors of the thymus, which may or may not be extensively infiltrated by non-neoplastic lymphocytes. The term thymoma is customarily used to describe neoplasms that show no overt atypia of the epithelial component. A thymic epithelial tumor that exhibits clear-cut cytologic atypia and histologic features no longer specific to the thymus is known as a thymic carcinoma (also known as type C thymoma).

The methods provided by the invention may comprise the administration of the benzamide metabolite compounds in combination with other therapies. The choice of therapy that can be co-administered with the compositions of the invention will depend, in part, on the condition being treated. For example, for treating acute myeloid leukemia, a benzamide compound of some embodiments of the invention can be used in combination with radiation therapy, monoclonal antibody therapy, chemotherapy, bone marrow transplantation, gene therapy, immunotherapy, or a combination thereof.

Breast Cancer

In one aspect, the invention provides a method of treating breast cancer, preferably a ductal carcinoma in duct tissue in a mammary gland.

Several types of breast cancer exist that may be treated by the methods provided by the invention. A lobular carcinoma in situ and a ductal carcinoma in situ are breast cancers that have developed in the lobules and ducts, respectively, but have not spread to the fatty tissue surrounding the breast or to other areas of the body. An infiltrating (or invasive) lobular and a ductal carcinoma are cancers that have developed in the lobules and ducts, respectively, and have spread to either the breast's fatty tissue and/or other parts of the body. Other cancers of the breast that would benefit from treatment by the methods provided by the invention are medullary carcinomas, colloid carcinomas, tubular carcinomas, and inflammatory breast cancer.

Treatments available for breast cancer patients are surgery, immunotherapy, radiation therapy, chemotherapy, endocrine therapy, or a combination thereof. A lumpectomy and a mastectomy are two possible surgical procedures available for breast cancer patients.

Chemotherapy utilizes anti-tumor agents to prevent cancer cells from multiplying, invading, metastasizing and killing a patient. Several drugs are available to treat breast cancer, including cytotoxic drugs such as doxorubicin, cyclophosphamide, methotrexate, paclitaxel, thiotepa, mitoxantrone, vincristine, or combinations thereof. Endocrine therapy may be an effective treatment where the remaining breast tissue retains endocrine sensitivity. Agents administered for this therapy include tamoxifen, megestrol acetate, aminoglutethimide, fluoxymesterone, leuprolide, gosserelin, and prednisone.

The methods provided by the invention can provide a beneficial effect for breast cancer patients, by administration of a nitrobenzamide metabolite compound or a combination of administration of a nitrobenzamide metabolite compound and surgery, radiation therapy, chemotherapy, or endocrine therapy.

In some embodiments, the invention provides for treatment of so-called "triple negative" breast cancer. There are several subclasses of breast cancer identified by classic biomarkers such as estrogen receptor (ER) and/or progesterone receptor (PR) positive tumors, HER2-amplified tumors, and ER/PR/HER2-negative tumors. These three subtypes have been reproducibly identified by gene expression profiling in multiple breast cancer and exhibit basal-like subtype expression profiles and poor prognosis. Triple negative breast cancer is characterized by ER/PR/HER2-negative tumors.

Ovarian Cancer

In another aspect, the invention provides a method of treating ovarian cancer, including epithelial ovarian tumors. Preferably, the invention provides a method of treating an ovarian cancer selected from the following: an adenocarcinoma in the ovary and an adenocarcinoma that has migrated from the ovary into the abdominal cavity. Surgery, immunotherapy, chemotherapy, hormone therapy, radiation therapy, or a combination thereof, are some possible treatments available for ovarian cancer. Some possible surgical procedures include debulking, and a unilateral or bilateral oophorectomy and/or a unilateral or bilateral salpigectomy.

Anti-cancer drugs that may be used include cyclophosphamide, etoposide, altretamine, and ifosfamide. Hormone therapy with the drug tamoxifen may be used to shrink ovarian tumors. Radiation therapy may be external beam radiation therapy and/or brachytherapy.

The methods provided by the invention can provide a beneficial effect for ovarian cancer patients, by administration of a nitrobenzamide metabolite compound or a combination of administration of a nitrobenzamide metabolite compound and surgery, radiation therapy, chemotherapy endocrine therapy, or a combination thereof.

Cervical Cancer

In another aspect, the invention provides a method of treating cervical cancer, preferably an adenocarcinoma in the cervical epithelium. Two main types of this cancer exist: squamous cell carcinoma and adenocarcinomas. The former constitutes about 80-90% of all cervical cancers and develops where the ectocervix (portion closest to the vagina) and the endocervix (portion closest to the uterus) join. The latter develop in the mucous-producing gland cells of the endocervix. Some cervical cancers have characteristics of both of these and are called adenosquamous carcinomas or mixed carcinomas.

The chief treatments available for cervical cancer are surgery, immunotherapy, radiation therapy and chemotherapy. Some possible surgical options are cryosurgery, a hysterectomy, and a radical hysterectomy. Radiation therapy for cervical cancer patients includes external beam radiation therapy or brachytherapy. Anti-cancer drugs that may be administered as part of chemotherapy to treat cervical cancer include cisplatin, carboplatin, hydroxyurea, irinotecan, bleomycin, vincrinstine, mitomycin, ifosfamide, fluorouracil, etoposide, methotrexate, and combinations thereof.

The methods provided by the invention can provide a beneficial effect for cervical cancer patients, by administration of a nitrobenzamide metabolite compound or a combination of administration of a nitrobenzamide metabolite compound and surgery, radiation therapy, chemotherapy, or a combination thereof.

Prostate Cancer

In one other aspect, the invention provides methods to treat prostate cancer, preferably a prostate cancer selected from the following: an adenocarcinoma or an adenocarcinoma that has migrated to the bone. Prostate cancer develops in the prostate organ in men, which surrounds the first part of the urethra. The prostate has several cell types but 99% of tumors are adenocarcinomas that develop in the glandular cells responsible for generating seminal fluid.

Surgery, immunotherapy, radiation therapy, cryosurgery, hormone therapy, and chemotherapy are some treatments available for prostate cancer patients. Possible surgical procedures to treat prostate cancer include radical retro-pubic prostatectomy, a radical perineal prostatectomy, and a laparoscopic radical prostatectomy. Some radiation therapy options are external beam radiation, including three dimensional conformal radiation therapy, intensity modulated radiation therapy, and conformal proton beam radiation therapy. Brachytherapy (seed implantation or interstitial radiation therapy) is also an available method of treatment for prostate cancer. Cryosurgery is another possible method used to treat localized prostate cancer cells.

Hormone therapy, also called androgen deprivation therapy or androgen suppression therapy, may be used to treat prostate cancer. Several methods of this therapy are available including an orchiectomy in which the testicles, where 90% of androgens are produced, are removed. Another method is the administration of luteinizing hormone-releasing hormone (LHRH) analogs to lower androgen levels. The LHRH analogs available include leuprolide, goserelin, triptorelin, and histrelin. An LHRH antagonist may also be administered, such as abarelix.

Treatment with an anti-androgen agent, which blocks androgen activity in the body, is another available therapy. Such agents include flutamide, bicalutamide, and nilutamide. This therapy is typically combined with LHRH analog administration or an orchiectomy, which is termed a combined androgen blockade (CAB).

Chemotherapy may be appropriate where a prostate tumor has spread outside the prostate gland and hormone treatment is not effective. Anti-cancer drugs such as doxorubicin, estramustine, etoposide, mitoxantrone, vinblastine, paclitaxel, docetaxel, carboplatin, and prednisone may be administered to slow the growth of prostate cancer, reduce symptoms and improve the quality of life.

The methods provided by the invention can provide a beneficial effect for prostate cancer patients, by administration of a nitrobenzamide metabolite compound or a combination administration of a nitrobenzamide metabolite compound and surgery, radiation therapy, chemotherapy, hormone therapy, or a combination thereof.

Pancreatic Cancer

In another aspect, the invention provides methods of treating pancreatic cancer, preferably a pancreatic cancer selected from the following: an epitheloid carcinoma in the pancreatic duct tissue and an adenocarcinoma in a pancreatic duct.

The most common type of pancreatic cancer is an adenocarcinoma, which occurs in the lining of the pancreatic duct. The possible treatments available for pancreatic cancer are surgery, immunotherapy, radiation therapy, and chemotherapy. Possible surgical treatment options include a distal or total pancreatectomy and a pancreaticoduodenectomy (Whipple procedure).

Radiation therapy may be an option for pancreatic cancer patients, specifically external beam radiation where radiation is focused on the tumor by a machine outside the body. Another option is intra-operative electron beam radiation administered during an operation.

Chemotherapy may be used to treat pancreatic cancer patients. Appropriate anti-cancer drugs include 5-fluorouracil (5-FU), mitomycin, ifosfamide, doxorubicin, streptozocin, chlorozotocin, and combinations thereof.

The methods provided by the invention can provide a beneficial effect for pancreatic cancer patients, by administration of a nitrobenzamide metabolite compound or a combination of administration of a nitrobenzamide metabolite compound and surgery, radiation therapy, or chemotherapy.

Bladder Cancer

In another aspect, the invention provides methods of treating bladder cancer, preferably a transitional cell carcinoma in urinary bladder. Bladder cancers are urothelial carcinomas (transitional cell carcinomas) or tumors in the urothelial cells that line the bladder. The remaining cases of bladder cancer are squamous cell carcinomas, adenocarcinomas, and small cell cancers. Several subtypes of urothelial carcinomas exist depending on whether they are non-invasive or invasive and whether they are papillary, or flat. Non-invasive tumors are in the urothelium, the innermost layer of the bladder, while invasive tumors have spread from the urothelium to deeper layers of the bladder's main muscle wall. Invasive papillary urothelial carcinomas are slender finger-like projections that branch into the hollow center of the bladder and also grow outward into the bladder wall. Non-invasive papillary urothelial tumors grow towards the center of the bladder. While a non-invasive, flat urothelial tumor (also called a flat carcinoma in situ) is confined to the layer of cells closest to the inside hollow part of the bladder, an invasive flat urothelial carcinoma invades the deeper layer of the bladder, particularly the muscle layer.

To treat bladder cancer, surgery, radiation therapy, immunotherapy, chemotherapy, or a combination thereof may be applied. Some possible surgical options are a transurethral resection, a cystectomy, or a radical cystectomy. Radiation therapy for bladder cancer may include external beam radiation and brachytherapy.

Immunotherapy is another method that may be used to treat a bladder cancer patient. Typically this is accomplished intravesically, which is the administration of a treatment agent directly into the bladder by way of a catheter. One method is Bacillus Calmete-Guerin (BCG) where a bacterium sometimes used in tuberculosis vaccination is given directly to the bladder through a catheter. The body mounts an immune response to the bacterium, thereby attacking and killing the cancer cells.

Another method of immunotherapy is the administration of interferons, glycoproteins that modulate the immune response. Interferon alpha is often used to treat bladder cancer.

Anti-cancer drugs that may be used in chemotherapy to treat bladder cancer include thitepa, methotrexate, vinblastine, doxorubicin, cyclophosphamide, paclitaxel, carboplatin, cisplatin, ifosfamide, gemcitabine, or combinations thereof.

The methods provided by the invention can provide a beneficial effect for bladder cancer patients, by administration of a nitrobenzamide metabolite compound or a combination of administration of a nitrobenzamide metabolite compound and surgery, radiation therapy, immunotherapy, chemotherapy, or a combination thereof.

Blood Cancer
  Lymphoma
  B-Cell Lymphomas

Non-Hodgkin's Lymphomas caused by malignant (cancerous) B-Cell lymphocytes represent a large subset (about 85% in the US) of the known types of lymphoma (the other 2 subsets being T-Cell lymphomas and lymphomas where the cell type is the Natural Killer Cell or unknown). Cells undergo many changes in their life cycle dependent on complex signaling processes between cells and interaction with foreign substances in the body. Various types of lymphoma or leukemia can occur in the B-Cell life cycle.

Acute Myeloid Leukemia

In another aspect, the invention provides methods of treating acute myeloid leukemia (AML), preferably acute promyelocytic leukemia in peripheral blood. AML begins in the bone marrow but can spread to other parts of the body including the lymph nodes, liver, spleen, central nervous system, and testes. It is acute, meaning it develops quickly and may be fatal if not treated within a few months. AML is characterized by immature bone marrow cells usually granulocytes or monocytes, which continue to reproduce and accumulate.

AML may be treated by immunotherapy, radiation therapy, chemotherapy, bone marrow or peripheral blood stem cell transplantation, or a combination thereof, Radiation therapy includes external beam radiation and may have side effects. Anti-cancer drugs that may be used in chemotherapy to treat AML include cytarabine, anthracycline, anthracenedione, idarubicin, daunorubicin, idarubicin, mitoxantrone, thioguanine, vincristine, prednisone, etoposide, or a combination thereof.

Monoclonal antibody therapy may be used to treat AML patients. Small molecules or radioactive chemicals may be attached to these antibodies before administration to a patient in order to provide a means of killing leukemia cells in the body. The monoclonal antibody, gemtuzumab ozogamicin, which binds CD33 on AML cells, may be used to treat AML patients unable to tolerate prior chemotherapy regimens.

Bone marrow or peripheral blood stem cell transplantation may be used to treat AML patients. Some possible transplantation procedures are an allogenic or an autologous transplant.

The methods provided by the invention can provide a beneficial effect for leukemia patients, by administration of a nitrobenzamide metabolite compound or a combination of administration of a nitrobenzamide metabolite compound and surgery, radiation therapy, chemotherapy, or transplantation therapy.

There are other types of leukemia's that can also be treated by the methods provided by the invention including but not limited to, Acute Lymphocytic Leukemia, Acute Myeloid Leukemia, Chronic Lymphocytic Leukemia, Chronic Myeloid Leukemia, Hairy Cell Leukemia, Myelodysplasia, and Myeloproliferative Disorders.

Lung Cancer

In another aspect, the invention provides methods to treat lung cancer. The most common type of lung cancer is non-small cell lung cancer (NSCLC), which accounts for approximately 80-85% of lung cancers and is divided into squamous cell carcinomas, adenocarcinomas, and large cell undifferentiated carcinomas. Small cell lung cancer accounts for 15-20% of lung cancers.

Treatment options for lung cancer include surgery, immunotherapy, radiation therapy, chemotherapy, photodynamic therapy, or a combination thereof. Some possible surgical options for treatment of lung cancer are a segmental or wedge resection, a lobectomy, or a pneumonectomy. Radiation therapy may be external beam radiation therapy or brachytherapy.

Some anti-cancer drugs that may be used in chemotherapy to treat lung cancer include cisplatin, carboplatin, paclitaxel, docetaxel, gemcitabine, vinorelbine, irinotecan, etoposde, vinblastine, gefitinib, ifosfamide, methotrexate, or a combination thereof. Photodynamic therapy (PDT) may be used to treat lung cancer patients.

The methods provided by the invention can provide a beneficial effect for lung cancer patients, by administration of a nitrobenzamide metabolite compound or a combination of administration of a nitrobenzamide metabolite compound and surgery, radiation therapy, chemotherapy, photodynamic therapy, or a combination thereof.

Skin Cancer

In another aspect, the invention provides methods to treat skin cancer. There are several types of cancer that start in the skin. The most common types are basal cell carcinoma and squamous cell carcinoma, which are non-melanoma skin cancers. Actinic keratosis is a skin condition that sometimes develops into squamous cell carcinoma. Non-melanoma skin cancers rarely spread to other parts of the body. Melanoma, the rarest form of skin cancer, is more likely to invade nearby tissues and spread to other parts of the body. Different types of treatment are available for patients with non-melanoma and melanoma skin cancer and actinic keratosis including surgery, radiation therapy, chemotherapy and photodynamic therapy. Some possible surgical options for treatment of skin cancer are Mohs micrographic surgery (MMS), simple excision, electrodesiccation and curettage, cryosurgery, laser surgery. Radiation therapy may be external beam radiation therapy or brachytherapy. Other types of treatments that are being tested in clinical trials are biologic therapy or immunotherapy, chemoimmunotherapy, topical chemotherapy with fluorouracil and photodynamic therapy.

The methods provided by the invention can provide a beneficial effect for skin cancer patients, by administration of a nitrobenzamide metabolite compound or a combination of administration of a nitrobenzamide metabolite compound and surgery, radiation therapy, chemotherapy, photodynamic therapy, or a combination thereof.

Eye Cancer, Retinoblastoma

In another aspect, the invention provides methods to treat eye retinoblastoma. Retinoblastoma is a malignant tumor of the retina. Although retinoblastoma may occur at any age, it most often occurs in younger children, usually before the age of 5 years. The tumor may be in one eye only or in both eyes. Retinoblastoma is usually confined to the eye and does not spread to nearby tissue or other parts of the body. Treatment options that attempt to cure the patient and preserve vision include enucleation (surgery to remove the eye), radiation therapy, cryotherapy, photocoagulation, immunotherapy, thermotherapy and chemotherapy. Radiation therapy may be external beam radiation therapy or brachytherapy.

The methods provided by the invention can provide a beneficial effect for eye retinoblastoma patients, by administration of a nitrobenzamide metabolite compound or a combination of administration of a nitrobenzamide metabolite compound and surgery, radiation therapy, cryotherapy, photocoagulation, thermotherapy and chemotherapy, or a combination thereof.

Eye Cancer, Intraocular Melanoma

In another aspect, the invention provides methods to treat intraocular (eye) melanoma. Intraocular melanoma, a rare cancer, is a disease in which cancer cells are found in the part of the eye called the uvea. The uvea includes the iris, the ciliary body, and the choroid. Intraocular melanoma occurs most often in people who are middle aged. Treatments for intraocular melanoma include surgery, immunotherapy, radiation therapy and laser therapy. Surgery is the most common treatment of intraocular melanoma. Some possible surgical options are iridectomy, iridotrabeculectomy, iridocyclectomy, choroidectomy, enucleation and orbital exenteration. Radiation therapy may be external beam radiation therapy or brachytherapy. Laser therapy may be an intensely powerful beam of light to destroy the tumor, thermotherapy or photocoagulation.

The methods provided by the invention can provide a beneficial effect for intraocular melanoma patients, by administration of a nitrobenzamide metabolite compound or a combination of administration of a nitrobenzamide metabolite compound and surgery, radiation therapy and laser therapy, or a combination thereof.

Endometrium Cancer

In another aspect, the invention provides methods to treat endometrium cancer. Endometrial cancer is a cancer that starts in the endometrium, the inner lining of the uterus. Some of the examples of the cancer of uterus and endometrium include, but are not limited to, adenocarcinomas, adenoacanthomas, adenosquamous carcinomas, papillary serous adenocarcinomas, clear cell adenocarcinomas, uterine sarcomas, stromal sarcomas, malignant mixed mesodermal tumors, and leiomyosarcomas.

The methods provided by the invention can provide a beneficial effect for endometrium cancer patients, by administration of a nitrobenzamide compound or a combination of administration of a nitrobenzamide compound and surgery, radiation therapy, chemotherapy, gene therapy, photodynamic therapy, antiangiogenesis therapy, and immunotherapy, or a combination thereof.

Liver Cancer

In another aspect, the invention provides methods to treat primary liver cancer (cancer that begins in the liver). Primary liver cancer can occur in both adults and children. Different types of treatments are available for patients with primary liver cancer. These include surgery, immunotherapy, radiation therapy, chemotherapy and percutaneous ethanol injection. The types of surgery that may be used are cryosurgery, partial hepatectomy, total hepatectomy and radiofrequency ablation. Radiation therapy may be external beam radiation therapy, brachytherapy, radiosensitizers or radiolabel antibodies. Other types of treatment include hyperthermia therapy and immunotherapy.

The methods provided by the invention can provide a beneficial effect for liver cancer patients, by administration of a nitrobenzamide metabolite compound or a combination of administration of a nitrobenzamide metabolite compound and surgery, radiation therapy, chemotherapy, percutaneous ethanol injection, hyperthemia therapy and immunotherapy, or a combination thereof.

Kidney Cancer

In another aspect, the invention provides methods to treat kidney cancer. Kidney cancer (also called renal cell cancer or renal adenocarcinoma) is a disease in which malignant cells are found in the lining of tubules in the kidney. Kidney cancer may be treated by surgery, radiation therapy, chemotherapy and immunotherapy. Some possible surgical options to treat kidney cancer are partial nephrectomy, simple nephrectomy and radical nephrectomy. Radiation therapy may be external beam radiation therapy or brachytherapy. Stem cell transplant may be used to treat kidney cancer.

The methods provided by the invention can provide a beneficial effect for kidney cancer patients, by administration of a nitrobenzamide metabolite compound or a combination of administration of a nitrobenzamide metabolite compound and surgery, radiation therapy, chemotherapy, immunotherapy and stem cell transplant, or a combination thereof.

Thyroid Cancer

In another aspect, the invention provides methods to treat thyroid cancer. Thyroid cancer is a disease in which cancer (malignant) cells are found in the tissues of the thyroid gland. The four main types of thyroid cancer are papillary, follicular, medullary and anaplastic. Thyroid cancer may be treated by surgery, immunotherapy, radiation therapy, hormone therapy and chemotherapy. Surgery is the most common treatment of thyroid cancer. Some possible surgical options for treatment of thyroid cancer are lobectomy, near-total thyroidectomy, total thyroidectomy and lymph node dissection. Radiation therapy may be external radiation therapy or may required intake of a liquid that contains radioactive iodine. Hormone therapy uses hormones to stop cancer cells from growing. In treating thyroid cancer, hormones can be used to stop the body from making other hormones that might make cancer cells grow.

The methods provided by the invention can provide a beneficial effect for thyroid cancer patients, by administration of a nitrobenzamide metabolite compound or a combination of administration of a nitrobenzamide metabolite compound and surgery, surgery, radiation therapy, hormone therapy and chemotherapy, or a combination thereof.

AIDS Related Cancers

AIDS-Related Lymphoma

In another aspect, the invention provides methods to treat AIDS-related lymphoma. AIDS-related lymphoma is a disease in which malignant cells form in the lymph system of patients who have acquired immunodeficiency syndrome (AIDS). AIDS is caused by the human immunodeficiency virus (HIV), which attacks and weakens the body's immune system. The immune system is then unable to fight infection and diseases that invade the body. People with HIV disease have an increased risk of developing infections, lymphoma, and other types of cancer. Lymphomas are cancers that affect the white blood cells of the lymph system. Lymphomas are divided into two general types: Hodgkin's lymphoma and non-Hodgkin's lymphoma. Both Hodgkin's lymphoma and non-Hodgkin's lymphoma may occur in AIDS patients, but non-Hodgkin's lymphoma is more common. When a person with AIDS has non-Hodgkin's lymphoma, it is called an AIDS-related lymphoma. Non-Hodgkin's lymphomas may be indolent (slow-growing) or aggressive (fast-growing). AIDS-related lymphoma is usually aggressive. The three main types of AIDS-related lymphoma are diffuse large B-cell lymphoma, B-cell immunoblastic lymphoma and small non-cleaved cell lymphoma.

Treatment of AIDS-related lymphoma combines treatment of the lymphoma with treatment for AIDS. Patients with AIDS have weakened immune systems and treatment can cause further damage. For this reason, patients who have AIDS-related lymphoma are usually treated with lower doses of drugs than lymphoma patients who do not have AIDS. Highly-active antiretroviral therapy (HAART) is used to slow progression of HIV. Medicine to prevent and treat infections, which can be serious, is also used. AIDS-related lymphomas may be treated by chemotherapy, immunotherapy, radiation therapy and high-dose chemotherapy with stem cell transplant. Radiation therapy may be external beam radiation therapy or brachytherapy. AIDS-related lymphomas can be treated by monoclonal antibody therapy.

The methods provided by the invention can provide a beneficial effect for AIDS-related lymphoma patients, by administration of a nitrobenzamide metabolite compound or a combination of administration of a nitrobenzamide metabolite compound and chemotherapy, radiation therapy and high-dose chemotherapy, or a combination thereof.

Kaposi's Sarcoma

In another aspect, the invention provides methods to treat Kaposi's sarcoma. Kaposi's sarcoma is a disease in which cancer cells are found in the tissues under the skin or mucous membranes that line the mouth, nose, and anus. Classic Kaposi's sarcoma usually occurs in older men of Jewish, Italian, or Mediterranean heritage. This type of Kaposi's sarcoma progresses slowly, sometimes over 10 to 15 years. Kaposi's sarcoma may occur in people who are taking immunosuppressants. Kaposi's sarcoma in patients who have Acquired Immunodeficiency Syndrome (AIDS) is called epidemic Kaposi's sarcoma. Kaposi's sarcoma in people with AIDS usually spreads more quickly than other kinds of Kaposi's sarcoma and often is found in many parts of the body. Kaposi's sarcoma may be treated with surgery, chemotherapy, radiation therapy and immunotherapy. External radiation therapy is a common treatment of Kaposi's sarcoma. Some possible surgical options to treat Kaposi's Sarcoma are local excision, electrodessiccation and curettage, and cryotherapy.

The methods provided by the invention can provide a beneficial effect for Kaposi's sarcoma, by administration of a nitrobenzamide metabolite compound or a combination of administration of a nitrobenzamide metabolite compound and surgery, chemotherapy, radiation therapy and immunotherapy, or a combination thereof.

Viral-Induced Cancers

In another aspect, the invention provides methods to treat viral-induced cancers. Several common viruses are clearly or probable causal factors in the etiology of specific malignancies. These viruses either normally establish latency or few can become persistent infections. Oncogenesis is probably linked to an enhanced level of viral activation in the infected host, reflecting heavy viral dose or compromised immune control. The major virus-malignancy systems include hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer. In general, these malignancies occur relatively early in life, typically peaking in middle-age or earlier.

Virus-Induced Hepatocellular Carcinoma

The causal relationship between both HBV and HCV and hepatocellular carcinoma or liver cancer is established through substantial epidemiologic evidence. Both appear to act via chronic replication in the liver by causing cell death and subsequent regeneration. Different types of treatments are available for patients with liver cancer. These include surgery, immunotherapy, radiation therapy, chemotherapy and percutaneous ethanol injection. The types of surgery that may be used are cryosurgery, partial hepatectomy, total hepatectomy and radiofrequency ablation. Radiation therapy may be external beam radiation therapy, brachytherapy, radiosensitizers or radiolabel antibodies. Other types of treatment include hyperthermia therapy and immunotherapy.

The methods provided by the invention can provide a beneficial effect for virus induce hepatocellular carcinoma patients, by administration of a nitrobenzamide metabolite compound or a combination of administration of a nitrobenzamide metabolite compound and surgery, radiation therapy, chemotherapy, percutaneous ethanol injection, hyperthemia therapy and immunotherapy, or a combination thereof.

Viral-Induced Adult T Cell Leukemia/Lymphoma

The association between lentiviruses (for example HTLV-1) and Adult T cell leukemia (ATL) is established. Unlike the other oncogenic viruses found throughout the world, HTLV-1 is highly geographically restricted, being found primarily in southern Japan, the Caribbean, west and central Africa, and the South Pacific islands. Evidence for causality includes the monoclonal integration of viral genome in almost all cases of ATL in carriers. The risk factors for HTLV-1-associated malignancy appear to be perinatal infection, high viral load, and being male sex.

Adult T cell leukemia is a cancer of the blood and bone marrow. The standard treatments for adult T cell leukemia/lymphoma are radiation therapy, immunotherapy, and chemotherapy. Radiation therapy may be external beam radiation therapy or brachytherapy. Other methods of treating adult T cell leukemia/lymphoma include immunotherapy and high-dose chemotherapy with stem cell transplantation.

The methods provided by the invention can provide a beneficial effect for Adult T cell leukemia patients, by administration of a nitrobenzamide metabolite compound or a combination of administration of a nitrobenzamide metabolite compound and radiation therapy, chemotherapy, immunotherapy and high-dose chemotherapy with stem cell transplantation, or a combination thereof.

Viral-Induced Cervical Cancer

Infection of the cervix with human papilloma virus (HPV) is the most common cause of cervical cancer. Not all women with HPV infection, however, will develop cervical cancer.

Cervical cancer usually develops slowly over time. Before cancer appears in the cervix, the cells of the cervix go through changes known as dysplasia, in which cells that are not normal begin to appear in the cervical tissue. Later, cancer cells start to grow and spread more deeply into the cervix and to surrounding areas. The standard treatments for cervical cancers are surgery, immunotherapy, radiation therapy and chemotherapy. The types of surgery that may be used are conization, total hysterectomy, bilateral salpingo-oophorectomy, radical hysterectomy, pelvic exenteration, cryosurgery, laser surgery and loop electrosurgical excision procedure. Radiation therapy may be external beam radiation therapy or brachytherapy.

The methods provided by the invention can provide a beneficial effect for adult cervical cancer, by administration of a nitrobenzamide metabolite compound or a combination of administration of a nitrobenzamide metabolite compound and radiation therapy, chemotherapy, or a combination thereof.

CNS Cancers

Brain and spinal cord tumors are abnormal growths of tissue found inside the skull or the bony spinal column, which are the primary components of the central nervous system (CNS). Benign tumors are non-cancerous, and malignant tumors are cancerous. The CNS is housed within rigid, bony quarters (i.e., the skull and spinal column), so any abnormal growth, whether benign or malignant, can place pressure on sensitive tissues and impair function. Tumors that originate in the brain or spinal cord are called primary tumors. Most primary tumors are caused by out-of-control growth among cells that surround and support neurons. In a small number of individuals, primary tumors may result from specific genetic disease (e.g., neurofibromatosis, tuberous sclerosis) or from exposure to radiation or cancer-causing chemicals. The cause of most primary tumors remains a mystery.

The first test to diagnose brain and spinal column tumors is a neurological examination. Special imaging techniques (computed tomography, and magnetic resonance imaging, positron emission tomography) are also employed. Laboratory tests include the EEG and the spinal tap. A biopsy, a surgical procedure in which a sample of tissue is taken from a suspected tumor, helps doctors diagnose the type of tumor.

Tumors are classified according to the kind of cell from which the tumor seems to originate. The most common brain tumor in adults comes from cells in the brain called astrocytes that make up the blood-brain barrier and contribute to the nutrition of the central nervous system. These tumors are called gliomas (astrocytoma, anaplastic astrocytoma, or glioblastoma multiforme) and account for 65% of all primary central nervous system tumors. Some of the tumors are, but not limited to, Oligodendroglioma, Ependymoma, Meningioma, Lymphoma, Schwannoma, and Medulloblastoma.

Neuroepithelial Tumors of the CNS

Astrocytic tumors, such as astrocytoma; anaplastic (malignant) astrocytoma, such as hemispheric, diencephalic, optic, brain stem, cerebellar; glioblastoma multiforme; pilocytic astrocytoma, such as hemispheric, diencephalic, optic, brain stem, cerebellar; subependymal giant cell astrocytoma; and pleomorphic xanthoastrocytoma. Oligodendroglial tumors, such as oligodendroglioma; and anaplastic (malignant) oligodendroglioma. Ependymal cell tumors, such as ependymoma; anaplastic ependymoma; myxopapillary ependymoma; and subependymoma. Mixed gliomas, such as mixed oligoastrocytoma; anaplastic (malignant) oligoastrocytoma; and others (e.g. ependymo-astrocytomas). Neuroepithelial tumors of uncertain origin, such as polar spongioblastoma; astroblastoma; and gliomatosis cerebri. Tumors of the choroid plexus, such as choroid plexus papilloma; and choroid plexus carcinoma (anaplastic choroid plexus papilloma). Neuronal and mixed neuronal-glial tumors, such as gangliocytoma; dysplastic gangliocytoma of cerebellum (Lhermitte-Duclos); ganglioglioma; anaplastic (malignant) ganglioglioma; desmoplastic infantile ganglioglioma, such as desmoplastic infantile astrocytoma; central neurocytoma; dysembryoplastic neuroepithelial tumor; olfactory neuroblastoma (esthesioneuroblastoma. Pineal Parenchyma Tumors, such as pineocytoma; pineoblastoma; and mixed pineocytoma/pineoblastoma. Tumors with neuroblastic or glioblastic elements (embryonal tumors), such as medulloepithelioma; primitive neuroectodermal tumors with multipotent differentiation, such as medulloblastoma; cerebral primitive neuroectodermal tumor; neuroblastoma; retinoblastoma; and ependymoblastoma.

Other CNS Neoplasms

Tumors of the Sellar Region, such as pituitary adenoma; pituitary carcinoma; and craniopharyngioma. Hematopoietic tumors, such as primary malignant lymphomas; plasmacytoma; and granulocytic sarcoma. Germ Cell Tumors, such as germinoma; embryonal carcinoma; yolk sac tumor (endodermal sinus tumor); choriocarcinoma; teratoma; and mixed germ cell tumors. Tumors of the Meninges, such as meningioma; atypical meningioma; and anaplastic (malignant) meningioma. Non-menigothelial tumors of the meninges, such as Benign Mesenchymal; Malignant Mesenchymal; Primary Melanocytic Lesions; Hemopoietic Neoplasms; and Tumors of Uncertain Histogenesis, such as hemangioblastoma (capillary hemangioblastoma). Tumors of Cranial and Spinal Nerves, such as schwannoma (neurinoma, neurilemoma); neurofibroma; malignant peripheral nerve sheath tumor (malignant schwannoma), such as epithelioid, divergent mesenchymal or epithelial differentiation, and melanotic. Local Extensions from Regional Tumors; such as paraganglioma (chemodectoma); chordoma; chodroma; chondrosarcoma; and carcinoma. Metastatic tumours, Unclassified Tumors and Cysts and Tumor-like Lesions, such as Rathke cleft cyst; Epidermoid; dermoid; colloid cyst of the third ventricle; enterogenous cyst; neuroglial cyst; granular cell tumor (choristoma, pituicytoma); hypothalamic neuronal hamartoma; nasal glial herterotopia; and plasma cell granuloma.

Chemotherapeutics available are, but not limited to, alkylating agents such as, Cyclophosphamide, Ifosphamide, Melphalan, Chlorambucil, BCNU, CCNU, Decarbazine, Procarbazine, Busulfan, and Thiotepa; antimetabolites such as, Methotraxate, 5-Fluorouracil, Cytarabine, Gemcitabine (Gemzar®), 6-mercaptopurine, 6-thioguanine, Fludarabine, and Cladribine; anthracyclins such as, daunorubicin. Doxorubicin, Idarubicin, Epirubicin and Mitoxantrone; antibiotics such as, Bleomycin; camptothecins such as, irinotecan and topotecan; taxanes such as, paclitaxel and docetaxel; and platinums such as, Cisplatin, carboplatin, and Oxaliplatin.

The treatments are surgery, radiation therapy, immunotherapy, hyperthermia, gene therapy, chemotherapy, and combination of radiation and chemotherapy. Doctors also may prescribe steroids to reduce the swelling inside the CNS.

The methods provided by the invention can provide a beneficial effect for adult cervical cancer, by administration of a nitrobenzamide metabolite compound or a combination of administration of a nitrobenzamide metabolite compound and radiation therapy, chemotherapy, or a combination thereof.

PNS Cancers

The peripheral nervous system consists of the nerves that branch out from the brain and spinal cord. These nerves form the communication network between the CNS and the body parts. The peripheral nervous system is further subdivided into the somatic nervous system and the autonomic nervous system. The somatic nervous system consists of nerves that go to the skin and muscles and is involved in conscious activities. The autonomic nervous system consists of nerves that connect the CNS to the visceral organs such as the heart, stomach, and intestines. It mediates unconscious activities.

Acoustic neuromas are benign fibrous growths that arise from the balance nerve, also called the eighth cranial nerve or vestibulocochlear nerve. These tumors are non-malignant, meaning that they do not spread or metastasize to other parts of the body. The location of these tumors is deep inside the skull, adjacent to vital brain centers in the brain stem. As the tumors enlarge, they involve surrounding structures which have to do with vital functions. In the majority of cases, these tumors grow slowly over a period of years.

The malignant peripheral nerve sheath tumor (MPNST) is the malignant counterpart to benign soft tissue tumors such as neurofibromas and schwannomas. It is most common in the deep soft tissue, usually in close proximity of a nerve trunk. The most common sites include the sciatic nerve, brachial plexus, and sarcal plexus. The most common symptom is pain which usually prompts a biopsy. It is a rare, aggressive, and lethal orbital neoplasm that usually arises from sensory branches of the trigeminal nerve in adults. Malignant PNS tumor spreads along nerves to involve the brain, and most patients die within 5 years of clinical diagnosis. The MPNST may be classified into three major categories with epithelioid, mesenchymal or glandular characteristics. Some of the MPNST include but not limited to, Subcutaneous malignant epithelioid schwannoma with cartilaginous differentiation, Glandular malignant schwannoma, Malignant peripheral nerve sheath tumor with perineurial differentiation, Cutaneous epithelioid malignant nerve sheath tumor with rhabdoid features, Superficial epithelioid MPNST, Triton Tumor (MPNST with rhabdomyoblastic differentiation), Schwannoma with rhabdomyoblastic differentiation. Rare MPNST cases contain multiple sarcomatous tissue types, especially osteosarcoma, chondrosarcoma and angiosarcoma. These have sometimes been indistinguishable from the malignant mesenchymoma of soft tissue.

Other types of PNS cancers include but not limited to, malignant fibrous cytoma, malignant fibrous histiocytoma, malignant meningioma, malignant mesothelioma, and malignant mixed Müllerian tumor.

The treatments are surgery, radiation therapy, immunotherapy, chemotherapy, and combination of radiation and chemotherapy.

The methods provided by the invention can provide a beneficial effect for PNS cancers, by administration of a nitrobenzamide metabolite compound or a combination of administration of a nitrobenzamide metabolite compound and radiation therapy, chemotherapy, or a combination thereof.

Oral Cavity and Oropharyngeal Cancer

Management of patients with central nervous system (CNS) cancers remains a formidable task. Cancers such as, hypopharyngeal cancer, laryngeal cancer, nasopharyngeal cancer, oropharyngeal cancer, and the like, have been treated with surgery, immunotherapy, chemotherapy, combination of chemotherapy and radiation therapy. Etoposide and actinomycin D, two commonly used oncology agents that inhibit topoisomerase II, fail to cross the blood-brain barrier in useful amounts.

The methods provided by the invention can provide a beneficial effect for Oral Cavity and Oropharyngeal cancer, by administration of a nitrobenzamide metabolite compound or a combination of administration of a nitrobenzamide metabolite compound and radiation therapy, chemotherapy, or a combination thereof.

Stomach Cancer

Stomach cancer is the result of cell changes in the lining of the stomach. There are three main types of stomach cancers: lymphomas, gastric stromal tumors, and carcinoid tumors. Lymphomas are cancers of the immune system tissue that are sometimes found in the wall of the stomach. Gastric stromal tumors develop from the tissue of the stomach wall. Carcinoid tumors are tumors of hormone-producing cells of the stomach.

The causes of stomach cancer continue to be debated. A combination of heredity and environment (diet, smoking, etc) are all thought to play a part. Common approaches to the treatment include surgery, immunotherapy, chemotherapy, radiation therapy, combination of chemotherapy and radiation therapy or biological therapy.

The methods provided by the invention can provide a beneficial effect for stomach cancer, by administration of a nitrobenzamide metabolite compound or a combination of administration of a nitrobenzamide metabolite compound and radiation therapy, chemotherapy, or a combination thereof.

Testicular Cancer

Testicular cancer is cancer that typically develops in one or both testicles in young men. Cancers of the testicle develop in certain cells known as germ cells. The 2 main types of germ cell tumors (GCTs) that occur in men are seminomas (60%) and nonseminomas (40%). Tumors can also arise in the supportive and hormone-producing tissues, or stroma, of the testicles. Such tumors are known as gonadal stromal tumors. The 2 main types are Leydig cell tumors and Sertoli cell tumors. Secondary testicular tumors are those that start in another organ and then spread to the testicle. Lymphoma is the most common secondary testicular cancer.

Common approaches to the treatment include surgery, immunotherapy, chemotherapy, radiation therapy, combination of chemotherapy and radiation therapy or biological therapy. Several drugs are typically used to treat testicular cancer: Platinol (cisplatin), Vepesid or VP-16 (etoposide) and Blenoxane (bleomycin sulfate). Additionally, Ifex (ifosamide), Velban (vinblastine sulfate) and others may be used.

The methods provided by the invention can provide a beneficial effect for stomach cancer, by administration of a nitrobenzamide metabolite compound or a combination of administration of a nitrobenzamide metabolite compound and radiation therapy, chemotherapy, or a combination thereof.

Thymus Cancer

The thymus is a small organ located in the upper/front portion of your chest, extending from the base of the throat to the front of the heart. The thymus contains 2 main types of cells, thymic epithelial cells and lymphocytes. Thymic epithelial cells can give origin to thymomas and thymic carcinomas. Lymphocytes, whether in the thymus or in the lymph nodes, can become malignant and develop into cancers called Hodgkin's disease and non-Hodgkin's lymphomas. The thymus also contains another much less common type of cells called Kulchitsky cells, or neuroendocrine cells, which normally release certain hormones. These cells can give rise to cancers, called carcinoids or carcinoid tumors that often release the same type of hormones, and are similar to other tumors arising from neuroendocrine cells elsewhere in the body.

Common approaches to the treatment include surgery, immunotherapy, chemotherapy, radiation therapy, combination of chemotherapy and radiation therapy or biological therapy. Anticancer drugs that have been used in the treatment of thymomas and thymic carcinomas are doxorubicin (Adriamycin), cisplatin, ifosfamide, and corticosteroids (prednisone). Often, these drugs are given in combination to increase their effectiveness. Combinations used to treat thymic cancer include cisplatin, doxorubicin, etoposide and cyclophosphamide, and the combination of cisplatin, doxorubicin, cyclophosphamide, and vincristine.

The methods provided by the invention can provide a beneficial effect for stomach cancer, by administration of a nitrobenzamide metabolite compound or a combination of administration of a nitrobenzamide metabolite compound and radiation therapy, chemotherapy, or a combination thereof.

Combination Therapy

One aspect of the invention provides methods for treating cancer using different combinations of treatment regimens. For example, such combinations may include, but are not limited to, the use of one or more of the nitrobenzamide compounds in conjunction with one or more various antineoplastic chemotherapeutic agents, chemopreventative agents, and/or side-effect limiting agents.

Antineoplastic Chemotherapeutic Agents

Suitable antineoplastic chemotherapeutic agents to be used in the present invention include, but are not limited to, alkylating agents, antimetabolites, natural antineoplastic agents, hormonal antineoplastic agents, angiogenesis inhibitors, differentiating reagents, RNA inhibitors, DNA inhibitors, inhibitors of viral replication, antibodies or immunotherapeutic agents, peptide agents, gene therapy agents, small molecule enzymatic inhibitors, biological response modifiers, and anti-metastatic agents.

Alkylating Agents

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g. busulfan), nitrosoureas (e.g. carmustine, lomustine, and streptozocin), triazenes (e.g. dacarbazine and temozolomide), ethylenimines/methylmelamines (e.g. altretamine and thiotepa), and methylhydrazine derivatives (e.g. procarbazine). Included in the alkylating agent group are the alkylating-like platinum-containing drugs comprising carboplatin, cisplatin, and oxaliplatin.

Antimetabolites

Antimetabolic antineoplastic agents structurally resemble natural metabolites, and are involved in normal metabolic processes of cancer cells such as the synthesis of nucleic acids and proteins. They differ enough from the natural metabolites so that they interfere with the metabolic processes of cancer cells. Suitable antimetabolic antineoplastic agents to be used in the present invention can be classified according to the metabolic process they affect, and can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemcitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

Natural Antineoplastic Agents

Natural antineoplastic agents comprise antimitotic agents, antibiotic antineoplastic agents, camptothecin analogues, and enzymes. Antimitotic agents suitable for use herein include, but are not limited to, vinca alkaloids like vinblastine, vincristine, vindesine, vinorelbine, and their analogues and derivatives. They are derived from the Madagascar periwinkle plant and are usually cell cycle-specific for the M phase, binding to tubulin in the microtubules of cancer cells. Other antimitotic agents suitable for use herein are the podophyllotoxins, which include, but are not limited to etoposide, teniposide, and their analogues and derivatives. These reagents predominantly target the G2 and late S phase of the cell cycle.

Also included among the natural antineoplastic agents are the antibiotic antineoplastic agents. Antibiotic antineoplastic agents are antimicrobial drugs that have anti-tumor properties usually through interacting with cancer cell DNA. Antibiotic antineoplastic agents suitable for use herein include, but are not limited to, belomycin, dactinomycin, doxorubicin, idarubicin, epirubicin, mitomycin, mitoxantrone, pentostatin, plicamycin, and their analogues and derivatives.

The natural antineoplastic agent classification also includes camptothecin analogues and derivatives which are suitable for use herein and include camptothecin, topotecan, and irinotecan. These agents act primarily by targeting the nuclear enzyme topoisomerase I. Another subclass under the natural antineoplastic agents is the enzyme, L-asparaginase and its variants. L-asparaginase acts by depriving some cancer cells of L-asparagine by catalyzing the hydrolysis of circulating asparagine to aspartic acid and ammonia.

Hormonal Antineoplastic Agents

Hormonal antineoplastic agents act predominantly on hormone-dependent cancer cells associated with prostate tissue, breast tissue, endometrial tissue, ovarian tissue, lymphoma, and leukemia. Such tissues may be responsive to and dependent upon such classes of agents as glucocorticoids, progestins, estrogens, and androgens. Both analogues and derivatives that are agonists or antagonists are suitable for use in the present invention to treat tumors. Examples of glucocorticoid agonists/antagonists suitable for use herein are dexamethasone, cortisol, corticosterone, prednisone, mifepristone (RU486), their analogues and derivatives. The progestin agonist/antagonist subclass of agents suitable for use herein includes, but is not limited to, hydroxyprogesterone, medroxyprogesterone, megestrol acetate, mifepristone (RU486), ZK98299, their analogues and derivatives. Examples from the estrogen agonist/antagonist subclass of agents suitable for use herein include, but are not limited to, estrogen, tamoxifen, toremifene, RU58668, SR16234, ZD164384, ZK191703, fulvestrant, their analogues and derivatives. Examples of aromatase inhibitors suitable for use herein, which inhibit estrogen production, include, but are not limited to, androstenedione, formestane, exemestane, aminoglutethimide, anastrozole, letrozole, their analogues and derivatives. Examples from the androgen agonist/antagonist subclass of agents suitable for use herein include, but are not limited to, testosterone, dihydrotestosterone, fluoxymesterone, testolactone, testosterone enanthate, testosterone propionate, gonadotropin-releasing hormone agonists/antagonists (e.g. leuprolide, goserelin, triptorelin, buserelin), diethylstilbestrol, abarelix, cyproterone, flutamide, nilutamide, bicalutamide, their analogues and derivatives.

Angiogenesis Inhibitors

Angiogenesis inhibitors work by inhibiting the vascularization of tumors. Angiogenesis inhibitors encompass a wide variety of agents including small molecule agents, antibody agents, and agents that target RNA function. Examples of angiogenesis inhibitors suitable for use herein include, but are not limited to, ranibizumab, bevacizumab, SU11248, PTK787, ZK222584, CEP-7055, angiozyme, dalteparin, thalidomide, suramin, CC-5013, combretastatin A4 Phosphate, LY317615, soy isoflavones, AE-941, interferon alpha, PTK787/ZK 222584, ZD6474, EMD 121974, ZD6474, BAY 543-9006, celecoxib, halofuginone hydrobromide, bevacizumab, their analogues, variants, or derivatives.

Differentiating Reagents

Differentiating agents inhibit tumor growth through mechanisms that induce cancer cells to differentiate. One such subclass of these agents suitable for use herein includes, but is not limited to, vitamin A analogues or retinoids, and peroxisome proliferator-activated receptor agonists (PPARs). Retinoids suitable for use herein include, but are not limited to, vitamin A, vitamin A aldehyde (retinal), retinoic acid, fenretinide, 9-cis-retinoid acid, 13-cis-retinoid acid, all-trans-retinoic acid, isotretinoin, tretinoin, retinyl palmitate, their analogues and derivatives. Agonists of PPARs suitable for use herein include, but are not limited to, troglitazone, ciglitazone, tesaglitazar, their analogues and derivatives.

RNA Inhibitors

Certain RNA inhibiting agents may be utilized to inhibit the expression or translation of messenger RNA ("miRNA") that is associated with a cancer phenotype. Examples of such agents suitable for use herein include, but are not limited to, short interfering RNA ("siRNA"), micro RNA ("miRNA"), ribozymes, and antisense oligonucleotides. Specific examples of RNA inhibiting agents suitable for use herein include, but are not limited to, Cand5, Sirna-027, fomivirsen, and angiozyme.

Antibodies/Immunotherapeutic Agents

Antibody agents bind targets selectively expressed in cancer cells and can either utilize a conjugate to kill the cell associated with the target, or elicit the body's immune response to destroy the cancer cells. Immunotherapeutic agents can either be comprised of polyclonal or monoclonal antibodies. The antibodies may be comprised of non-human animal (e.g. mouse) and human components, or be comprised of entirely human components ("humanized antibodies"). Examples of monoclonal immunotherapeutic agents suitable for use herein include, but are not limited to, rituximab, tosibtumomab, ibritumomab which target the CD-20 protein. Other examples suitable for use herein include trastuzumab, edrecolomab, bevacizumab, cetuximab, carcinoembryonic antigen antibodies, gemtuzumab, alemtuzumab, mapatumumab, panitumumab, EMD 72000, TheraCIM hR3, 2C4, HGS-TR2J, and HGS-ETR2.

Gene Therapy Agents

Gene therapy agents insert copies of genes into a specific set of a patient's cells, and can target both cancer and non-cancer cells. The goal of gene therapy can be to replace altered genes with functional genes, to stimulate a patient's immune response to cancer, to make cancer cells more sensitive to chemotherapy, to place "suicide" genes into cancer cells, or to inhibit angiogenesis. Genes may be delivered to target cells using viruses, liposomes, or other carriers or vectors. This may be done by injecting the gene-carrier composition into the patient directly, or ex vivo, with infected cells being introduced back into a patient. Such compositions are suitable for use in the present invention.

Small Molecule Enzymatic Inhibitors

Certain small molecule therapeutic agents are able to target the tyrosine kinase enzymatic activity or downstream signal transduction signals of certain cell receptors such as epidermal growth factor receptor ("EGFR") or vascular endothelial growth factor receptor ("VEGFR"). Such targeting by small molecule therapeutics can result in anti-cancer effects. Examples of such agents suitable for use herein include, but are not limited to, imatinib, gefitinib, erlotinib, lapatinib, canertinib, ZD6474, sorafenib (BAY 43-9006), ERB-569, and their analogues and derivatives.

Biological Response Modifiers

Certain protein or small molecule agents can be used in anti-cancer therapy through either direct anti-tumor effects or through indirect effects. Examples of direct-acting agents suitable for use herein include, but are not limited to, differentiating reagents such as retinoids and retinoid derivatives. Indirect-acting agents suitable for use herein include, but are not limited to, agents that modify or enhance the immune or other systems such as interferons, interleukins, hematopoietic growth factors (e.g. erythropoietin), and antibodies (monoclonal and polyclonal).

Anti-Metastatic Agents

The process whereby cancer cells spread from the site of the original tumor to other locations around the body is termed cancer metastasis. Certain agents have anti-metastatic properties, designed to inhibit the spread of cancer cells. Examples of such agents suitable for use herein include, but are not limited to, marimastat, bevacizumab, trastuzumab, rituximab, erlotinib, MMI-166, GRN163L, hunter-killer peptides, tissue inhibitors of metalloproteinases (TIMPs), their analogues, derivatives and variants.

Chemopreventative Agents

Certain pharmaceutical agents can be used to prevent initial occurrences of cancer, or to prevent recurrence or metastasis. Administration with such chemopreventative agents in combination with one or more other anticancer agents including the nitrobenzamide compounds can act to both treat and prevent the recurrence of cancer. Examples of chemopreventative agents suitable for use herein include, but are not limited to, tamoxifen, raloxifene, tibolone, bisphosphonate, ibandronate, estrogen receptor modulators, aromatase inhibitors (letrozole, anastrozole), luteinizing hormone-releasing hormone agonists, goserelin, vitamin A, retinal, retinoic acid, fenretinide, 9-cis-retinoid acid, 13-cis-retinoid acid, all-trans-retinoic acid, isotretinoin, tretinoid, vitamin B6, vitamin B12, vitamin C, vitamin D, vitamin E, cyclooxygenase inhibitors, non-steroidal anti-inflammatory drugs (NSAIDs), aspirin, ibuprofen, celecoxib, polyphenols, polyphenol E, green tea extract, folic acid, glucaric acid, interferon-alpha, anethole dithiolethione, zinc, pyridoxine, finasteride, doxazosin, selenium, indole-3-carbinal, alpha-difluoromethylornithine, carotenoids, beta-carotene, lycopene, antioxidants, coenzyme Q10, flavonoids, quercetin, curcumin, catechins, epigallocatechin gallate, N-acetylcysteine, indole-3-carbinol, inositol hexaphosphate, isoflavones, glucanic acid, rosemary, soy, saw palmetto, and calcium. An additional example of chemopreventative agents suitable for use in the present invention is cancer vaccines. These can be created through immunizing a patient with all or part of a cancer cell type that is targeted by the vaccination process.

Side-Effect Limiting Agents

Treatment of cancer with nitrobenzamide compounds alone or in combination with other antineoplastic compounds may be accompanied by administration of pharmaceutical agents that can alleviate the side effects produced by the antineoplastic agents. Such agents suitable for use herein include, but are not limited to, anti-emetics, anti-mucositis agents, pain management agents, infection control agents, and anti-anemia/anti-thrombocytopenia agents. Examples of anti-emetics suitable for use herein include, but are not limited to, 5-hydroxytryptamine 3 receptor antagonists, metoclopramide, steroids, lorazepam, ondansetron, cannabinoids, their analogues and derivatives. Examples of anti-mucositis agents suitable for use herein include, but are not limited to, palifermin (keratinocyte growth factor), glucagon-like peptide-2, teduglutide, L-glutamine, amifostin, and fibroblast growth factor 20. Examples of pain management agents suitable for use herein include, but are not limited to, opioids, opiates, and non-steroidal anti-inflammatory compounds. Examples of agents used for control of infection suitable for use herein include, but are not limited to, antibacterials such as aminoglycosides, penicillins, cephalosporins, tetracyclines, clindamycin, lincomycin, macrolides, vancomycin, carbapenems, monobactams, fluoroquinolones, sulfonamides, nitrofurantoins, their analogues and derivatives. Examples of agents that can treat anemia or thrombocytopenia associated with chemotherapy suitable for use herein include, but are not limited to, erythropoietin, and thrombopoietin.

Several other suitable therapies for use in combination with the nitrobenzamide compounds and other compounds described herein are also available. For example, see Goodman & Gilman's The Pharmacological Basis of Therapeutics 11th ed. Brunton L L, Lazo J S, and Parker K L, ed. McGraw-Hill, New York, 2006.

Formulations, Routes of Administration, and Effective Doses

Another aspect of the present invention relates to formulations and routes of administration for pharmaceutical compositions comprising a nitrobenzamide metabolite compound. Such pharmaceutical compositions can be used to treat cancer in the methods described in detail above.

In some embodiments, the metabolite compounds depicted herein above may be provided individually or in combination as a prodrug and/or may be allowed to interconvert to a nitrosobenzamide form in vivo after administration. Furthermore, said metabolite compounds may be administered with the nitrobenzamide of formula Ia which may be provided as a prodrug and/or may be allowed to interconvert to a nitrosobenzamide form in vivo after administration. That is, either the nitrobenzamide form and/or the nitrosobenzamide form, or pharmaceutically acceptable salts may be used in developing a formulation for use in the present invention. Further, in some embodiments, the metabolite compound may be used in combination with one or more other compounds or in one or more other forms. For example a formulation may comprise both the nitrobenzamide metabolite compound and acid forms in particular proportions, depending on the relative potencies of each and the intended indication. The two forms may be formulated together, in the same dosage unit e.g. in one cream, suppository, tablet, capsule, or packet of powder to be dissolved in a beverage; or each form may be formulated in a separate unit, e.g., two creams, two suppositories, two tablets, two capsules, a tablet and a liquid for dissolving the tablet, a packet of powder and a liquid for dissolving the powder, etc.

In compositions comprising combinations of a nitrobenzamide metabolite compound and another active agent can be effective. The two compounds and/or forms of a compound may be formulated together, in the same dosage unit e.g. in one cream, suppository, tablet, capsule, or packet of powder to be dissolved in a beverage; or each form may be formulated in separate units, e.g., two creams, suppositories, tablets, two capsules, a tablet and a liquid for dissolving the tablet, a packet of powder and a liquid for dissolving the powder, etc.

The term "pharmaceutically acceptable salt" means those salts which retain the biological effectiveness and properties of the compounds used in the present invention, and which are not biologically or otherwise undesirable. For example, a pharmaceutically acceptable salt does not interfere with the beneficial effect of the compound of the invention in treating a cancer.

Typical salts are those of the inorganic ions, such as, for example, sodium, potassium, calcium and magnesium ions. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the compounds used in the present invention contain a carboxy group or other acidic group, it may be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine and triethanolamine.

For oral administration, the metabolite compounds can be formulated readily by combining the active compound(s) with pharmaceutically acceptable carriers well known in the art. Such carriers enable the compounds of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media and various non-toxic organic solvents. Generally, the compounds of the invention will be included at concentration levels ranging from about 0.5%, about 5%, about 10%, about 20%, or about 30% to about 50%, about 60%, about 70%, about 80% or about 90% by weight of the total composition of oral dosage forms, in an amount sufficient to provide a desired unit of dosage.

Aqueous suspensions may contain a nitrobenzamide metabolite compound with pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, and the like.

In some embodiments, oils or non-aqueous solvents may be required to bring the metabolite compounds into solution, due to, for example, the presence of large lipophilic moieties. Alternatively, emulsions, suspensions, or other preparations, for example, liposomal preparations, may be used. With respect to liposomal preparations, any known methods for preparing liposomes for treatment of a condition may be used. See, for example, Bangham et al., J. Mol. Biol, 23: 238-252 (1965) and Szoka et al., Proc. Natl Acad. Sci 75: 4194-4198 (1978), incorporated herein by reference. Ligands may also be attached to the liposomes to direct these compositions to particular sites of action. Compounds of this invention may also be integrated into foodstuffs, e.g, cream cheese, butter, salad dressing, or ice cream to facilitate solubilization, administration, and/or compliance in certain patient populations.

Pharmaceutical preparations for oral use may be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; flavoring elements, cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents may be added, such as the cross-linked polyvinyl pyrrolidone, agar, or alginic acid or a salt thereof such as sodium alginate. The compounds may also be formulated as a sustained release preparation.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for administration.

For injection, the inhibitors of the present invention may be formulated in aqueous solutions, preferably in physiologically compatible buffers such as Hank's solution, Ringer's solution, or physiological saline buffer. Such compositions may also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton Pa. These compounds may also be formulated for transmucosal administration, buccal administration, for administration by inhalation, for parental administration, for transdermal administration, and rectal administration.

In addition to the formulations described previously, the metabolite compounds may also be formulated as a depot preparation. Such long acting formulations may be administered by implantation or transcutaneous delivery (for example subcutaneously or intramuscularly), intramuscular injection or use of a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions suitable for use in the present invention include compositions wherein the active ingredients are present in an effective amount, i.e., in an amount effective to achieve therapeutic and/or prophylactic benefit in at least one of the cancers described herein. The actual amount effective for a particular application will depend on the condition or conditions being treated, the condition of the subject, the formulation, and the route of administration, as well as other factors known to those of skill in the art. Determination of an effective amount of a nitrobenzamide metabolite compound is well within the capabilities of those skilled in the art, in light of the disclosure herein, and will be determined using routine optimization techniques.

EXAMPLES

Example 1

Identification of Benzamide Metabolites

Plasma samples were obtained from dog, rat and mouse studies, in which animals were administered 4-iodo-3-nitrobenzamide (BA). Plasma and tumor samples were prepared for HPLC injection by precipitating plasma (50 µl) with 3× volumes (150 µl) of acetonitrile. Tissue samples were prepared for HPLC injection by adding 1 µl of acetonitrile per mg of tissue, then homogenizing with an electric homogenizer. Following centrifugation, 150 µl of each supernatant was evaporated to dryness, reconstituted in 50 µl of 0.2% formic acid in water and analyzed by chromatography and mass spectrometry techniques (LC/MS/MS conditions). LC/MS/MS conditions are: HPLC (Shimadzu VP System); Mobile Phase: 0.2% formic acid in water (A) and 0.18% formic acid in methanol (B); Column: 1×50 mm Thermo BetaBasic C18 column; Injection volume: 25 µL; Gradient: 0-60% B in 30 minutes; Flow Rate: 100 µL/min; Mass Spectrometer: Applied Biosystems/MDS SCIEX Q-STAR; Interface: IonSpray split at ¹⁄₁₀; Parent Ion Scan: TOF Positive from 200-900 amu; Product Ion Scan: TOF Product Ion from 60-900 amu of most intense Ion in Parent Ion Scan; TOF calibration: Externally calibrated using Renin Substrate. Results of metabolite identification from dog and mouse plasma are depicted in Tables 1-3, as follows:

TABLE 1

Summary of BA metabolite identification by LC/MS/MS from canine plasma

| Name | Compound or Metabolite | Retention Time (min) | Approximate ng/ml [a] |
|---|---|---|---|
| Parent (292.9 m/z) | BSI-201 | 14.4 | 1.9 |
| M1 (405 m/z) | +112 amu | 8.1 | 8.6 |
| M2 (472 m/z) | +179 amu | 8.8 | 75 |
| M3 (213 m/z) | −80 amu | 13.4 | 44 |
| M4 (263 m/z) | −29 amu | 16.8 | 12 |
| M5 (334 m/z) | +41 amu | 19.4 | 5.0 |
| M6 (569 m/z) | +276 amu | 19.7 | 2.5 |
| M7 (413 m/z) | +121 amu | 21.0 | 20 |

[a] Approximate ng/ml equivalents were measured using BSI-201 in the 1 µg/ml spike sample as a reference standard.

For clarity, the names in Tables 1 above correspond to compounds disclosed above as follows (name:compound): M2:MS472, M3:MS213 and M4:MS263.

TABLE 2

Summary of BA metabolite identification by LC/MS/MS from murine plasma

| Name | Compound or Metabolite | Retention Time (min) | Approximate ng/ml [a] |
|---|---|---|---|
| Parent (292.9 m/z) | BSI-201 | 14.4 | 3.7 |
| M1 (278 m/z) | −14 amu | 8.1 | 61 |
| M2 (276 m/z) | −16 amu | 8.6 | 3.2 |
| M3 (472 m/z) | +179 amu | 8.9 | 375 |
| M4 (634 m/z) | +341 amu | 9.5 | 31 |
| M5 (262 m/z) | −30 amu | 10.2 | 200 |
| M6 (328 m/z) | +35 amu | 11.3 | 100 |

TABLE 2-continued

Summary of BA metabolite identification by LC/MS/MS from murine plasma

| Name | Compound or Metabolite | Retention Time (min) | Approximate ng/ml [a] |
|---|---|---|---|
| M7 (213 m/z) | −80 amu | 13.5 | 44 |
| M8 (263 m/z) | −29 amu | 16.8 | 56 |

[a] Approximate ng/ml equivalents were measured using BSI-201 in the 1 µg/ml spike sample as a reference standard.

For clarity, the names in Tables 2 above correspond to compounds disclosed herein as follows (name:compound): M3:MS472, M6:MS328, M7:MS213 and M8:MS263.

TABLE 3

Summary of BA metabolite identification by LC/MS/MS from canine plasma and red blood cells

| Name | Compound or Metabolite | Retention Time (min) | Approximate µg/ml[a] Plasma | Approximate µg/ml[a] RBC |
|---|---|---|---|---|
| Parent (292.9 m/z) | BSI-201 | 14.2 | 2.1 | 1.6 |
| M1 (645 m/z) | +352 amu | 7.0 | ND | 0.8 |
| M2 (472 m/z) | +179 amu | 8.8 | 2.3 | 0.02 |
| M2 (601 m/z) | +308 amu | 8.9 | 0.8 | 0.4 |

[a] Approximate µg/ml equivalents were measured using the 270 nm UV peak area of BSI-201 in the 5 µg/ml spike sample as a reference standard.

For clarity, the names in Tables 3 above correspond to compounds disclosed herein as follows (name:compound): M2:MS472 and the second M2:MS601.

Example 2

In Vitro Studies—Cytotoxicity Assays

Different types of cancer cell lines of different origin or primary cells may be seeded ($5 \times 10^4$) on 48 wells plate, or ($2 \times 10^4$) on 96 wells plate. The cells may be cultured in the appropriate medium. Cultures can be maintained in a 37° C. incubator in a humidified atmosphere of 95% $O_2$/5% $CO_2$. After the cells are seeded (24 hours), medium is removed and replaced with culture medium in the presence of various concentrations of INO2BA or INH2BP, in the presence or not of 200 µM BSO. After 6 days of incubation at 37° C., cell viability is measured using the Cell Titer-Blue, Cell Viability Assay (Promega) (See O'Brien, J. et al. (2000) Investigation of the Alamar Blue (resazurin) fluorescent dye for the assessment of mammalian cell cytotoxicity. Eur. J. Biochem. 267, 5421-26 and Gonzalez, R. J. and Tarloff, J. B. (2001) Evaluation of hepatic subcellular fractions for Alamar Blue and MTT reductase). This assay incorporates a fluorometric/colorometric growth indicator based on detection by vital dye reduction. Cytotoxicity is measured by growth inhibition.

Cytotoxicity may also be assessed by counting the number of viable cells. Cells were harvested by washing the monolayer with PBS, followed by a brief incubation in 0.25% trypsin and 0.02% EDTA. The cells are then collected, washed twice by centrifugation and resuspended in PBS. Cell number and viability is determined by staining a small volume of cell suspension with a 0.2% trypan blue saline solution and examining the cells in a hemocytometer. See Kerley-Hamilton et al. (2005) p53-dominant transcriptional response to cisplatin in testicular germ cell tumor-derived human embryonal carcinoma and Cheol et al. (2005) Induction of apoptosis and inhibition of cyclooxygenase-2 expression by N-methyl-N'-nitro-N-nitrosoguanidine in human leukemia cells.

Example 3

Cell Proliferation Measured with BrdU-ELISA

The cells may be incubated in the presence of various concentrations of the test substance (drugs) in a black 96-well MultiPlate (tissue culture grade; flat, clear bottom) at a final volume of 100 µl/well in a humidified atmosphere at 37° C. 10 µl/well BrdU labeling solution was added if the cells were cultured in 100 µl/well (final concentration: 10 µM BrdU) and the cells are reincubated for additional 2 to 24 hours at 37° C. (if the cells were cultured in 200 µl/well, 20 µl/well BrdU labeling solution was added). The MP is centrifuged at 300×g for 10 min and the labeling medium was removed with suction using a canulla. The cells are dried using a hair-dryer for about 15 min or, alternatively, at 60° C. for 1 h. 200 ul/well FixDenat is added to the cells and incubated for 30 min at 15-25° C. FixDenat solution is removed thoroughly by flicking off and tapping. 100 µl/well Anti-BrdU-POD working solution is added and incubated for approx. 90 min at 15-25° C. Alternatively, this incubation period can be varied between 30-120 min, depending on individual requirements. Antibody conjugate is removed by flicking off and wells were rinsed three times with 200-300 µl/well washing solution. Washing solution is removed by tapping. Then 100 µl/well substrate solution is added to each well. The light emission of the samples can be measured in a microplate luminometer with photomultiplier.

Example 4

In Vivo Implantation and Tumor Growth 100 female NU/NU-nuBR mice (Charles River, 5-6 wks) can be implanted with 0.72 mg 17β-estradiol (human) pellets, ear tagged using clips and weighed 24-48 hours prior to tumor cell implantation. Tumor cells, BT474, ($2 \times 10^7$ cells/mouse) are injected into the subscapular mammary fat pad (0.2 ml volume). Caliper measurements begin on day 21 and three times weekly thereafter (Mon, Wed, Fri). Animals are segregated according to the presence and absence of tumor and then by tumor volume. Animals are weighed twice weekly beginning the $3^{rd}$ week post implantation (Mon and Fri.). Drug treatment is started when tumor sizes were 150-250 $mm^3$ (L*W*H). Drug and vehicle administration is BID by gavage (BP+BSO) and SID by IP (BA) for five days. There is a two day rest period before the next cycle begins. Animals may receive three cycles (5 days each) unless there was unexpected toxicity. Body weight loss that exceeded 15% of initial values or display of certain symptoms may be used as criteria for animal euthanasia. Drug is administered by gavage and IP in volume of 5 ml/kg. Drug and vehicle are stored at 4° C. in foil-covered bottle.

| | | Study Design | | | |
|---|---|---|---|---|---|
| Group | Implant conditions | Cells implanted | # Mice | # Tumors needed | Treatment (BID) |
| 1 | sc | $2 \times 10^7$ | 20 | 10 | none |
| 2 | sc | $2 \times 10^7$ | 20 | 10 | Vehicle (10% DMSO in saline) |
| 3 | sc | $2 \times 10^7$ | 20 | 10 | BP + BSO (175 mg/kg + 220 mg/kg) P.O. |
| 4 | sc | $2 \times 10^7$ | 20 | 10 | BA (5 g/kg) I.P. |
| 5 | sc | $2 \times 10^7$ | 20 | 10 | Combo* (30 mg/kg) I.P. and P.O. |

*combination of BP + BSO and BA

Example 4

Xenograft Studies

The effects of the metabolite compounds can be evaluated on ovarian human cancer cells (OVCAR) xenografts in nude mice.

Female NU/NU 37-BU-04-BAC mice (Charles River, 5-6 weeks) are ear tagged using clips and weighed 24-48 hours prior to tumor cell implantation. Tumor cells Ovcar3 (5×01 cells/mouse) are implanted subcutaneously into the subscapular mammary fat pad of female nude mice hosts. Caliper measurement begin on day 7 post tumor cells implantation and 2 times weekly thereafter (Mon and Fri). Animals are segregated according to the presence or absence of tumor and then tumor volume. Animals are weighed once a week. Drug treatment starts when sizes were 0.4-0.5 cm in largest diameter. 4-Iodo-3-nitrobenzamide (BA) (in 50 µL of 100% DMSO/mouse and vehicle (50 µL of 100% DMSO/mouse) are injected by IP twice per day for five days. There is a two day rest period before the next cycle begins.

| | | STUDY DESIGN | |
|---|---|---|---|
| Group | Implant conditions | Cells implanted | TREATMENT |
| 1 | SC | $5 \times 10^6$ | Vehicle × 2 (50 µl of 100% DMSO/mouse) |
| 2 | SC | $5 \times 10^6$ | BA 25 mg/kg × 2/day (in 50 µl of 100% DMSO/mouse) |
| 3 | SC | $5 \times 10^6$ | BA 50 mg/kg × 2/day (in 50 µl of 100% DMSO/mouse) |
| 4 | SC | $5 \times 10^6$ | Nothing (Control) |

Example 5

Evaluating the Efficacy of a Metabolite Compound

General Methods

MDA MB 231 human mammary cancer cells may be injected subcutaneously into the right flank of female nude mice. For Task 1, BP may be administered for 5 consecutive days prior to tumor cell implantation, and drug administration continued 5 days a week for 4-8 weeks thereafter. For Task 2, cancer cells are injected when the tumors reached a mean tumor volume of 50-60 mm³, and mice are divided into groups of eight and treated with corn oil:PEG 400 (control), BP, or CTX (MDA MB 231 positive control). Tumor volumes are monitored for 90 days (for MDA MB 231) after the beginning of treatment.

Cell Lines

MDA MB 231 is a human mammary cancer cell line that was established in 1973 from a pleural effusion of a patient who had been treated with 5-FU, doxorubicin, methotrexate, and CTX in the 3 months before the cell line was initiated. This line is estrogen receptor negative and has been used in screening anticancer drugs that are not targeted as hormone antagonists. MDA MB 231 was grown in Dulbecco's modified Eagle medium (DMEM) with 1.5 g $NaHCO_3$/L, 10% fetal bovine serum (FBS), and 2 mM L-glutamine and was kept at 37° C. in a humidified 5% $CO_2$/air incubator. Antibiotics were not added to the medium.

Animal Tumor Model

Mice

Female CB.17 SCID mice (Charles River) were 8-11 weeks old, and had a body weight (BW) range of 12.6-23.0 g on D1 of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated ALPHA-dri® bed-o-cobs® Laboratory Animal Bedding in static microisolators on a 12-hour light cycle at 21-22° C. (70-72° F.) and 40-60% humidity in the laboratory accredited by Association for Assessment and Accreditation of Laboratory (AAALAC) International, which assures compliance with accepted standards for the care and use of laboratory animals.

Tumor Implantation

The human OVCAR-3 (NIH-OVCAR-3) ovarian adenocarcinoma utilized in the study was maintained in athymic nude mice by serial engraftment. A tumor fragment (1 mm³) was implanted subcutaneously (s.c.) into the right flank of each test mouse. Tumors were monitored twice weekly and then daily as their volumes approached 80-120 mm³. On D1 of the study, animals were sorted into treatment groups with tumor sizes of 63-221 mm³ and group mean tumor sizes of ~105 mm³.

Tumor size, in mm³, was calculated from:

$$\text{Tumor Volume} = \frac{w^2 \times l}{2}$$

Tumor weight may be estimated with the assumption that 1 mg is equivalent to 1 mm³ of tumor volume.

Treatment

Mice were sorted into nine groups (n=10) and treated in accordance with the protocol. Oral group received BA orally (p.o.) twice daily from D1 p.m. until D68 a.m. (b.i.d. (twice daily) to end). Alzet model osmotic pumps were implanted on Days 1, 15, and 29. The pumps were pre-warmed for ~1 hour at 37° C., and then implanted s.c. in the left flanks of isofluorane anesthetized mice. Each pump delivered a total dose of 25 mg/kg/week of BA over 14 days.

Endpoint

Tumors were calipered twice weekly for the duration of the study. Each animal was euthanized when its neoplasm reached the predetermined endpoint size (1,000 mm³). The time to endpoint (TTE) for each mouse was calculated by the following equation:

$$TTE = \frac{\log_{10}(\text{endpoint volume}) - b}{m}$$

where TTE is expressed in days, endpoint volume is in mm³, b is the intercept, and m is the slope of the line obtained by linear regression of a log-transformed tumor growth data set.

The data set is comprised of the first observation that exceeded the study endpoint volume and the three consecutive observations that immediately preceded the attainment of the endpoint volume. The calculated TTE is usually less than the day on which an animal is euthanized for tumor size. Animals that do not reach the endpoint are euthanized at the end of the study, and assigned a TTE value equal to the last day (68 days). Treatment efficacy was determined from tumor growth delay (TGD), which is defined as the increase in the median TTE for a treatment group compared to the control group: TGD=T−C, expressed in days, or as a percentage of the median TTE of the control group:

$$\% TGD = \frac{T - C}{C} \times 100$$

where:
T=median TTE for a treatment group,
C=median TTE for control Group 1.

The results of these studies are shown in FIG. 4.

Swiss NCr nude (nu/nu) female mice, age 4-5 weeks, are commercially available from Taconic (Germantown, N.Y.). The animals are housed three per cage in sterile filter-topped cages in a barrier clean room purchased from Bio Bubble, Inc. (Fort Collins, Colo.). Upon arrival, they are quarantined for four working days before use. Temperature was maintained at 72±5° F. and relative humidity at 35-70%, and a 12-hr light/dark cycle was used. The mice are fed sterile, autoclavable, certified Purina rodent chow ad libitum. Drinking water is acidified and autoclaved, and the source water is recirculated, deionized, UV-treated, and 5 µm filtered.

After the animals are released from quarantine, the mice are injected subcutaneously in the right flank with 1 or 5×10⁶ MDA MB 231 cells (0.1-ml injection volume). The mice for Task 1 received pretreatment for 5 days before cell injection. Tumor dimensions and body weight are measured twice weekly. Vernier calipers are used to measure tumors in three planes, and tumor volume (V) is calculated as follows: V=π (x×y×z)/6, where x, y, and z are the tumor measurements minus skin thickness. At the end of the experiment, the mice are sacrificed by $CO_2$ inhalation followed by cervical dislocation.

Pharmaceuticals

MS472 can be made up in corn oil:PEG 400 (2:1, V/V) at concentrations of 30 mg/ml and 100 mg/ml. The drug may be a suspension at these concentrations. Positive control drugs are made up on phosphate buffered saline (PBS) and CTX at 15 mg/ml. Both drugs can be filter-sterilized (0.2-µm filter) before use.

Treatment Protocol

For Task 1, mice to be implanted with MDA MB 231 tumor cells can be pretreated for 5 days with MS472 (300 or 1000 mg/kg), and following subcutaneous injection of the cell suspension, drug treatment is continued 5 days a week (Monday through Friday) for a minimum of 4 weeks.

For Task 2, after the tumor volumes reach a predetermined size (mean tumor volume 50-60 mm3), mice are divided into treatment groups of eight mice each. All treatments of BP are administered five times per week (Monday through Friday) for at least 4 weeks. CTX is administered intraperitoneally one time only at a dose of 150 mg/kg. All BP treatments are administered orally; the dosage was 1000 or 2000 mg/kg for those implanted with MDA MB 231 cells. For each task, all treatments would begin on the same day.

The tumors would be measured twice weekly for at least 9 weeks (MDA MB 231) after the first treatment. The mean tumor volume for each group is calculated for each time point. Comparisons between groups at specific times are made using an unpaired, two-tailed t-test, and the results are analyzed using analysis of variance (ANOVA). For Task 2, individual tumor volumes (V) are expressed as a fraction of the tumor volume on Day 0, the first day of treatment (V0). For each group, the mean of the ratio V/V0 is plotted as a function of time after treatment. Response to treatment is measured in two ways, depending on the tumor response to treatment. The tumor volume doubling time (VDT) and volume quadrupling time (VQT) is determined for each tumor by linear regressions on the plot of time as a function of log (tumor volume) in groups where there is a response to treatment. Tumor growth delay for each treatment group is determined and comparisons between groups are analyzed using ANOVA.

Systemic toxicity is assessed from reductions in body weight after treatment. The mice are sacrificed at the end of the follow-up period, or earlier in their tumor volumes reached 1600 mm³ or the tumors ulcerated.

Statistical Analysis

Statistical analysis can be performed using InStat (Graphpad Software, San Diego, Calif.).

Tumor Growth

MDA MB 231 tumors may be measurable within 3 weeks of tumor cell injection and usually grow more slowly, with a doubling time of 7 days. Values may be calculated from the control group. Mean tumor volumes and body weights at the start of treatment can be shown under the formats depicted in Table 4 for Task 1 and Table 5 for Task 2.

TABLE 4

MOUSE PARAMETERS AT THE START OF TREATMENT - TASK 1

| Treatment Group | Tumor Volume (mm³ ± SEM*) | Mouse Weight (g ± SEM*) |
| --- | --- | --- |
| PBS (control) MDA MB 231 | 0 | 24.0 ± 0.8 |
| 300 mg/kg | 0 | 24.6 ± 0.9 |
| 1000 mg/kg | 0 | 23.6 ± 07 |

*SEM = Standard error of the mean.

TABLE 5

MOUSE PARAMETERS AT THE START OF TREATMENT - TASK 2

| Treatment Group | Tumor Volume ($mm^3$ ± SEM*) | Mouse Weight (g ± SEM*) |
|---|---|---|
| MDA MB 231 | | |
| Corn oil (control) | 19.1 ± 5.1 | 24.4 ± 0.54 |
| 1000 mg/kg | 24.4 ± 5.8 | 24.5 ± 0.7 |
| 2000 mg/kg | 23.5 ± 5.8 | 23.0 ± 0.8 |
| CTX, 150 mg/kg | 24.0 ± 4.4 | 23.8 ± 0.4 |

*SEM = Standard error of the mean

The above examples are in no way intended to limit the scope of the instant invention. Further, it can be appreciated to one of ordinary skill in the art that many changes and modifications can be made thereto without departing from the spirit or scope of the appended claims, and such changes and modifications are contemplated within the scope of the instant invention.

Example 6

Cell Cycle Analysis

HCT116 and Hela cells were obtained from ATCC. For DNA content analysis, $2\times10^5$ cells were washed twice with PBS and fixed in 70% ethanol. Cells were treated with 100 units/mL RNase A for 20 minutes at 37° C., resuspended in cold PBS containing Alexa Fluor® 405 fluorescent stain (Invitrogen) according to the manufacturer's protocol. Cells were analyzed by flow cytometry. FIG. 1 illustrates (FACS dot plots and histograms) cell-cycle analysis in HTC116 cells treated with PARP-1 inhibitor (4-iodo-3-nitrobenzamide or "BA") for 19 hours. BA treatment caused an increase in the number of cells in the G1 phase (48.6%) as compared to control (18.6%) with a concomitant decrease of S phase cell cycle.

For DNA replication analysis, 2×105 cells were incubated with 50 µmol/L bromodeoxyuridine (BrdUrd) for 30 minutes. Cells were fixed in 70% ethanol and BrdUrd incorporation was determined by flow cytometric analysis using an anti-BrdUrd-FITC antibody (Becton Dickinson, Franklin Lakes, N.J.) according to the manufacturer's protocol. To assess the degree of G2/M checkpoint, mitotic cells were detected by flow cytometry using the mitosis-specific antibody GF-7. Fixed cells were incubated for 30 minutes with GF7-phycoerythrin (PE) antibody (BD Biosciences Pharmingen), washed with PBS and analyzed by flow cytometry. FIG. 2 compares the results obtained with BA, BNO (4-iodo-3-nitrosobenzamide) and BNHOH (4-iodo-3-hydroxyaminobenzamide) at 24 hr. incubation; FIG. 3 shows the results for BA, BNO and BNHOH at 72 hr.

Image analysis and microscopy. Cells grown on coverslips were fixed with 4% paraformaldehyde in PBS for 10 minutes and permeabilized in 70% ethanol. After washing, the coverslips were mounted on slides in 50% PBS/50% glycerol. Images were analyzed by microscopy.

MDR1 Expression FACS Assay.

KB-V1 is a vinblastine resistant clone of KB-3-1 human carcinoma cell line (Fojo, A. T., J Whang-Peng, M. M. Gottesman, and I. Pastan. 1985. *Amplification of DNA sequences in human multidrugresistant KB carcinoma cells. Proc. Natl. Acad. Sci. USA* 82:7661-7665., Shen, D.-W., C. Cardarelli, J lwang, M. Cornwell, N. Richert, S. Ishii, I. Pastan, and M. M. Gottesman. 1986. *Multiple drug-resistant human KB carcinoma cells independently selected for high-level resistance to colchicine, Adriamycin, or vinblastine show changes in expression of specific proteins. J. Biol. Chem.* 261:7762-7770). Cells were propagated in Eagle minimal essential medium with 10% fetal bovine serum.

For MDR1 staining cells were harvested by tripsinization, washed in Iscove's Modified Dulbecco's Medium supplemented with 5% FBS and then resuspended in of IMDM/5% FBS containing anti-Mdr1 antibody UIC2. After incubation with the primary antibody cells were washed and then incubated with a secondary antibody conjugated to phycoerythrin (PE) antibody (BD Biosciences Pharmingen). The antibody-treated cells were washed and then analyzed on a FACSCalibur® instrument (Becton Dickinson). Controls used in the FACS analysis were cells that had not been incubated with antibody, cells that had been incubated with an isotype control antibody. Triplicate samples were assayed, and their histograms were analyzed. The median fluorescence was plotted on a log scale. FIGS. 6A and 6B show the level of MDR1 in KB 3-1 and KB V-1 cells, respectively: Thus the FACS histograms demonstrate the overexpression of MDR1 in KB V-1 cells. Overexpression of MDR1 is associated with multidrug resistance.

Colony-Forming Assay

Cells were trypsinized, counted, and diluted to a final concentration of $10^6$ cells/ml. Colony-forming assays were performed by plating an appropriate number of cells into culture dishes in triplicates and treated with 0-100 µM of a compound. After 14 days, cells were fixed and stained with 1% crystal violet, and colonies were counted. FIG. 5C shows the results of this experiment in KB 3-1 and KB V-1 cells. As can be seen in FIG. 5C, BA reduces the number of cell colonies in a dose-dependant manner for both MDR1 overexpressing and MDR1 normal cells. As MDR1 overexpression is associated with multidrug resistance, this result suggests that BA will be effective against multidrug resistant tumors.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. An isolated compound of the structural Formula (IIa):

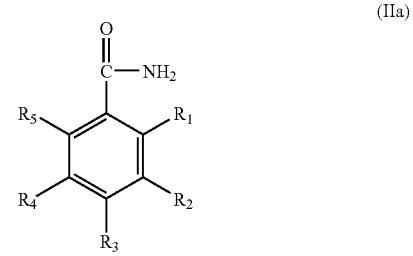

(IIa)

wherein at least one of $R_1$, $R_2$, $R_3$, $R_4$, and $R_5$ substituents is always a sulfur-containing substituent and where $R_1$, $R_2$, $R_3$, $R_4$, and $R_5$ are independently selected from the group consisting of hydrogen, hydroxy, amino, nitro, iodo, bromo, fluoro, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, and wherein the sulfur-containing substituent is selected from the group consisting of:

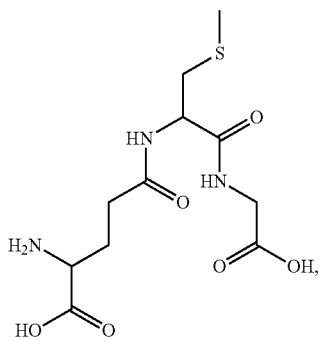
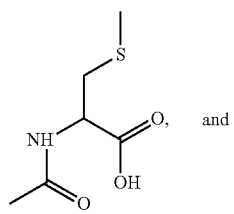 and
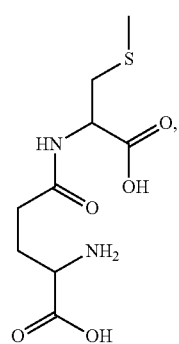
or a pharmaceutically acceptable salt thereof.
2. An isolated compound selected from the group consisting of:
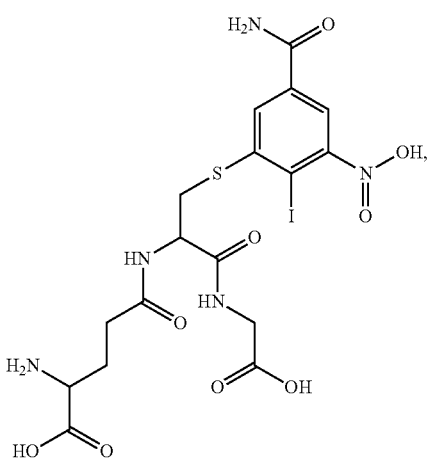
MS601
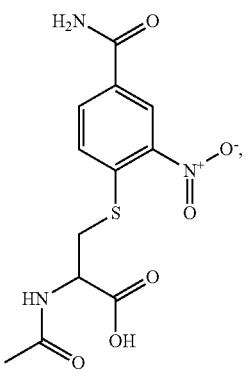
MS328
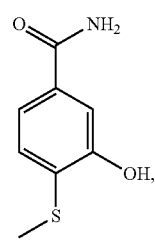
MS183
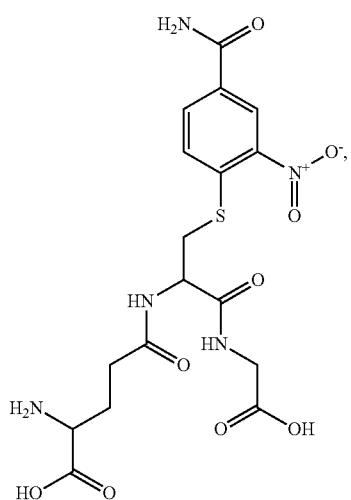
MS472
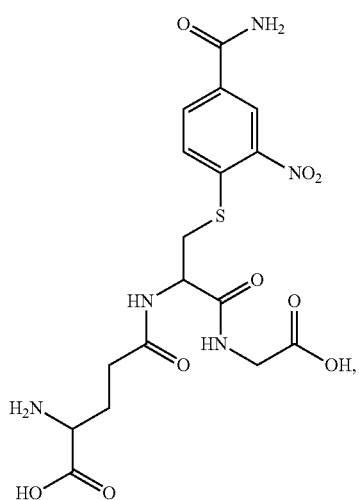
MS471

-continued

MS414

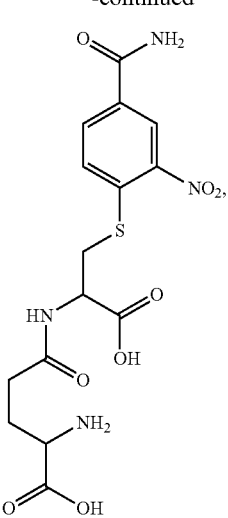

or a salt thereof, and
a compound of formula MS213

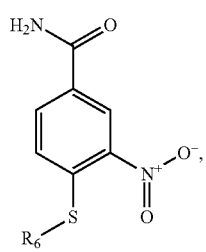

wherein $R_6$ is selected from the group consisting of alkoxy ($C_1$-$C_8$), isoquinolinones, thiazole, oxazole, oxadiazole, and thiophene, or a salt thereof.

3. The isolated compound of claim 2, wherein said compound is in the form of a pharmaceutically acceptable salt thereof.

4. An isolated compound of the formula MS 213:

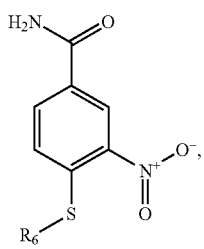

MS213 wherein $R_6$ is selected from the group consisting of alkoxy ($C_1$-$C_8$), isoquinolinones, thiazole, oxazole, oxadiazole, and thiophene, or a pharmaceutically acceptable salt thereof.

* * * * *

Disclaimer

8,143,447, B2 — Jerome Moore, Issaquah, WA (US); Bruce Keyt, Hillsborough, CA (US); John Burnier, Pacifica, CA (US); Barry M. Sherman, Hillsborough, CA (US); Max Totrov, San Diego, CA (US); Valeria S. Ossovskaya, San Francisco, CA (US), TREATMENT OF CANCER. Patented date March 27, 2012. Disclaimer filed December 19, 2013 by the Assignee, BiPar Sciences, Inc.

Hereby enter this disclaimer to the entire term of said patent.

*(Official Gazette, April 1, 2014)*